US011993657B2

(12) United States Patent
Tsurushita et al.

(10) Patent No.: US 11,993,657 B2
(45) Date of Patent: May 28, 2024

(54) BIFUNCTIONAL MOLECULES FOR TREATMENT OF IMMUNE DISORDERS

(71) Applicant: JN BIOSCIENCES LLC, Mountain View, CA (US)

(72) Inventors: Naoya Tsurushita, Palo Alto, CA (US); J. Yun Tso, Menlo Park, CA (US)

(73) Assignee: JN BIOSCIENCES LLC, Mountain View, CA (US)

( * ) Notice: Subject to any disclaimer, the term of this patent is extended or adjusted under 35 U.S.C. 154(b) by 0 days.

(21) Appl. No.: 17/694,570

(22) Filed: Mar. 14, 2022

(65) Prior Publication Data

US 2022/0306753 A1 Sep. 29, 2022

Related U.S. Application Data

(60) Provisional application No. 63/161,713, filed on Mar. 16, 2021.

(51) Int. Cl.
| | | |
|---|---|---|
| C07K 16/28 | (2006.01) | |
| A61K 47/68 | (2017.01) | |
| A61P 37/06 | (2006.01) | |

(52) U.S. Cl.
CPC ...... *C07K 16/2866* (2013.01); *A61K 47/6811* (2017.08); *A61K 47/6849* (2017.08); *A61K 47/6889* (2017.08); *A61P 37/06* (2018.01)

(58) Field of Classification Search
None
See application file for complete search history.

(56) References Cited

U.S. PATENT DOCUMENTS

| | | | |
|---|---|---|---|
| 7,794,718 B2 * | 9/2010 | Karrer | A61P 37/00 424/134.1 |
| 9,028,830 B2 * | 5/2015 | Tso | C07K 16/2866 530/387.9 |
| 9,382,319 B2 | 7/2016 | Tso et al. | |
| 10,287,321 B2 * | 5/2019 | Cobbold | A61P 25/28 |
| 2006/0165706 A1 | 7/2006 | Carreno et al. | |
| 2011/0250213 A1 | 10/2011 | Tso et al. | |
| 2016/0340422 A1 | 11/2016 | Chen et al. | |
| 2017/0073430 A1 | 3/2017 | Boontanrart et al. | |
| 2017/0096470 A1 | 4/2017 | Ghayur et al. | |

FOREIGN PATENT DOCUMENTS

WO WO 2022/197610 A1 9/2022

OTHER PUBLICATIONS

Lloyd et al., Protein Engineering, Design & Selection 22:159-168 (Year: 2009).*
Edwards et al., J Mol Biol 334(1): 103-118 (Year: 2003).*
Goenka et al., J Immunology 206(5): 1102-1113 (Year: 2021).*
Anthony, et al., "Emerging roles for IL-15 in the activation and function of T-cells during immune stimulation," Research and Reports in Biology, 6, 25-37, (Feb. 2015).
Anthony, et al., "Identification of a receptor required for the anti-inflammatory activity of IVIG," PNAS, vol. 105, No. 50, pp. 19571-19578, (Dec. 2008).
Baumeister, et al., "Coinhibitory Pathways in Immunotherapy fo Cancer," Annu. Rev. Immunol. 34: 539-73, (Feb. 2016).
Bruckner, et al., "Sweet SIGNs: IgG glycosylation leads the way in IVIG-mediated resolution of inflammation," International Immunology, vol. 29, No. 11, pp. 499-509, (Oct. 2017).
Crow, et al., "The neonatal Fc receptor (FcRn) is not requied for IVIg or anti-CD44 monoclonal antibody-mediated amelioration of murine immune thrombocytopenia," Blood, vol. 118, No. 24, 6403-6406, (Dec. 2011).
Curtsinger, et al., "Inflammatory Cytokines as a Third Signal for T Cell Activation," Curr Opin Immunol, 22(3): 333-340, (Jun. 2010).
Czajkowsky, et al., "Developing the IVIG biomimetic, Hexa-Fc, for drug and vaccine applications," Scientific Reports, 5: 9526, (Apr. 2015).
Dudek, et al., "Auto-aggressive CXCR6+ CD8T cells cause liver immune pathologoy in NASH," Nature, pp. 1-31, (Mar. 2021).
Esensten, et al., "CD28 costimulation: from mechanism to therapy," Immunity, 44(5): 973-988, (May 2016).
Fehniger, "Mystery Solved: IL-15," J Immunol, 202: 3125-2126, doi: 10.4049/jimmunol.1900419, (2019).
Fransen, et al., "Tissue-resident memory T cells invade the brain parenchyma in multiple sclerosis white matter lesions," Brain, 143; 1714-1730, (May 2020).
Gallo, et al., "Prevention of acute rejection after rescue with Belatacept by association of low-dose Tacrolimus maintenance in medically complex kidney transplant recipients with early or late graft dysfunction," PLoS ONE, 15(10): e0240335, (Oct. 2020).
Goenka, et al., "CTLA4-lg-Based Bifunctional Costimulation Inhibitor Blocks CD28 and ICOS Signaling to Prevent T Cell Prining and Effector Function," J Immunol, 206: 1102-1113, (Jan. 2021).
Gutcher, et al., "APC-derived cytokines and T cell polarization in autoimmune inflammation," J Clin Invest., 117(5): 1119-1127, (May 2007).
Hurton, et al., "Tethered IL-15 augments antitumor activity and promotes a stem-cell memory subset in tumor-specific T cells," PNAS, e7788-E7797, (Nov. 2016).
Kamiya, et al., "A new in vitro model of polymyositis reveass CD8+ T cell invasion into muscle cells and its cytotoxic role," Rheumatology, 59:224-232, (2020).

(Continued)

*Primary Examiner* — Phuong Huynh
(74) *Attorney, Agent, or Firm* — Alston & Bird LLP

(57) ABSTRACT

The invention provides bifunctional molecules including an antibody specifically binding to CD122 and an extracellular domain of CTLA-4. The bifunctional molecules specifically bind to CD122 and CTLA-4 ligands, CD80 and CD86 and inhibit their function in immune activation. The bifunctional molecules can inhibit interaction of CD122 with its ligands IL-2 and IL-15 and inhibit interaction of CD80 and CD86 with their counter-receptor, CD28. These bifunctional molecules can suppress Signals 2 and 3 of immune responses as a single therapeutic agent for treatment of immune disorders.

25 Claims, 13 Drawing Sheets

Specification includes a Sequence Listing.

(56) References Cited

OTHER PUBLICATIONS

Kaneko, et al., "Anti-Inflammatory Activity of Immunoglobulin G Resulting from Fc Sialylation," Science, vol. 313, pp. 670-673, (Aug. 2006).
Kiessling, et al., "The FcRn inhibitor rozanolixizumab reduces human serum lgG concentration: A randomized phase 1 study," Sci. Transl. Med., 9, eaan1208, corrected Dec, 6, 2017, (Nov. 2017).
Larsen, et al., "Rational Development of LEA29Y (belatacept), a High-Affinity Variant of CTLA4-lg with Potent Immunosuppressive Properties," American Journal of Transplantation, 5: 443-453, (2005).
Mahoney, et al., "Combination cancer immunotherapy and new immunomodulatory targets," Nature Reviews, Drug Discovery, vol. 14, pp. 561-584 (Aug. 2015).
Mathews, et al., "CD122 signaling in CD8+ memory T cells drives costimulation-independent rejection," J Clin Invest, doi.org/0.0072/JCI95914, (2018).
Mitrevski, et al., "Immunomodulatory Effects of Intravenous Immunoglobulin—Assembling a Jigsaw Puzzle," International Trends in Immunity, vol. 2, No. 2, (Apr. 2014).
Moreland, et al., "Abatacept," Nature Reviews, Drug Discovery, vol. 5, pp. 185-186, (Mar. 2006).
Nemeth, et al., "Crohn's Disease and Ulcerative Colitis Show Unique Cytokine Profiles," Cureus, 9(4): e1177, doi: 10.7759/cureus.1177, (Apr. 2017).
Nitschke, "CD22 and Siglec-G regulate inhibitaion of B-cell signaling by sialic acid ligand binding and control B-cell tolerance," Glycobiology, vol. 24, No. 9, pp. 807-817, (Jul. 2014).
Nixon, et al., "Fully human monoclonal antibody inibitor of the neonatal Fc receptor reduce circulating lgG in non-human primates," Frontiers in Immunology, vol. 6, Article 176, (Apr. 2015).
Oshima, et al., "ASP2408 and ASP2409, novel CTLA4-lg variants with CD86-selective ligand binding activity and improved immunosuppressive potency, created by directed evolution," Protein Engineering, Design & Selection, vol. 29, No. 5, pp. 159-167, (Mar. 2016).
Patel, et al., "Neonatal Fc Receptor Blockade by Fc Engineering Ameliorates Arthritis in Murine Model," J Immunol, 187: 1015-1022, (Jun. 2011).
Perez, et al., "Belatacept in Solid Organ Transplant: Review of Current Literature Across Transplant Types," Transplantation, vol. 102, No. 9, pp. 1440-1452, (Sep. 2018).
Rath, et al., "Regulation of immune responses by the neonatal Fc receptor and its therapeutic implications," Frontiers in Immunology, vol. 5, Article 664, (Jan. 2015).
Richmond, et al., "Antibody blockade of IL-15 signaling has the potential to durably reverse vitiligo," Sci. Transl. Med., 10, eaam7710, (Jul. 2018).
Siete, et al., "Intravenous Immunoglobulin and B Cells, When the Product Regulates the Producer," Arthritis & Rehumatology, vol. 67, No. 3, pp. 575-603, (Mar. 2015).
Spirig, et al., "rlgG1 Fc Hexamer Inhibits Antibody-Mediated Autoimune Disease visa Effects on Complement and FcyRs," The Journal of Immunology, 200: 2542-2553, (2018).
Tam, et al., "Corrlations between pharmackokinetics of lgG antibodies in primates vs. FcRn-transgenic mice reveal a rodent model with predictive capabilities," mAbs, 5:3, 397-405, (May/Jun. 2013).
Topham, et al., "Tissue-Resident Memory CD8+ T Cells: from Phenotype to Function," Frontiers in Immunology, vol. 8, Article 515, (Mar. 2018).
Torphy, et al., "Newly Emerging Immune Checkpoints: Promises for Future Cancer Therapy," Int. J. Mol. Sci, 18, 2642, doi:10.3390/ijms18122642, (Dec. 2017).
Ulrichts, et al., "Neonatal Fc receptor antagonist efgartigimod safely and sustainably reduces lgGs in humans," J Clin Invest., 128(10): 4372-4386, (Oct. 2018).
Ward-Kavanagh, et al., "The TNF Receptor Superfamily in Costimulating and Coinhibitory Responses," Immunity, 44(5): 1005-1019, (May 2016).
Washburn, et al., "Controlled tetra-Fc sialylation of IVIg results in a drug candidate with consistent enhanced anti-inflammatory activity," PNAS, E1297-E1306, (Mar. 2015).
Xing, et al., "Alopecia areata is driven by cytotoxic T lymphocytes and is reversed by JAK inhibition," Nat Med., 20(9): 1043-1049, (Sep. 2014).
Yang, et al., "Immunomodulatory Effects of IL-2 and IL-15; Implications for Cancer Immunotherapy," 12, 3586, doi:10.3390/cancers12123586, (Nov. 2020).
Yokoyama, et al., "Transgenic Mice that Overexpress Human IL-15 in Enterocytes Recapitulate Both B and T Cell-Mediated Pathologic Manifestations of Celiac Disease," J Clin Immunol, 31:1038-1044, (Sep. 2011).
Yu, et al., "The number of CD8+ T cells and NKT cells increases in the aqueous humor of patients with Behcet's uveitis," Clin Exp Immunol, 137:437-443, (May 2004).
PCT/US2022/020194 International Search Report and Written Opinion dated Aug. 19, 2022.
PCT/US2022/020194 International Preliminary Report on Patentability dated Sep. 12, 2023.

\* cited by examiner

Figs. 1A, B

Figs. 6A, B, C
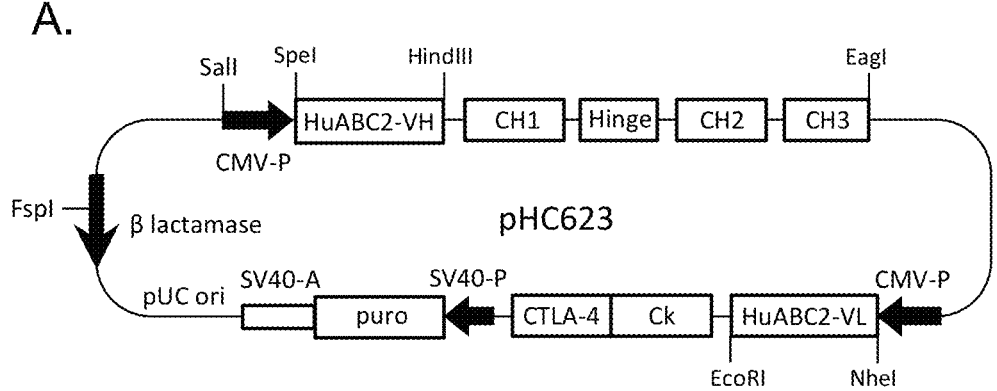
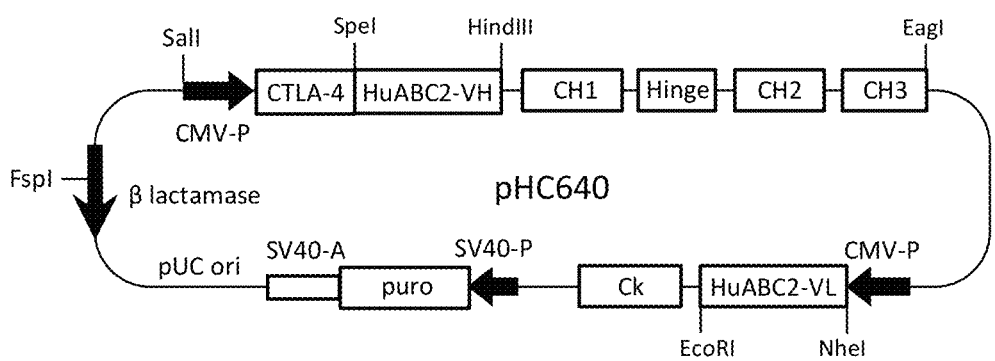
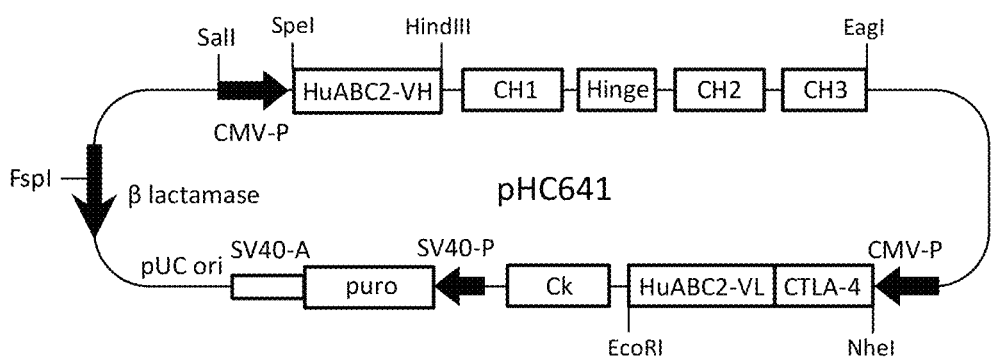

Figs. 7A, B, C
A.
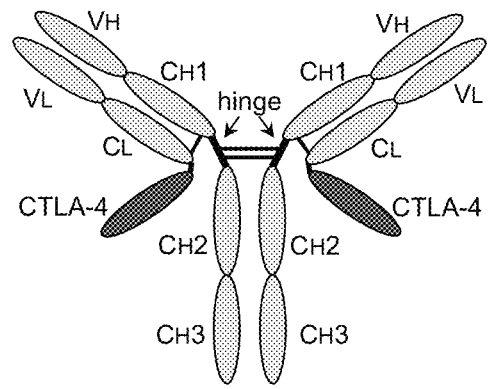
B.
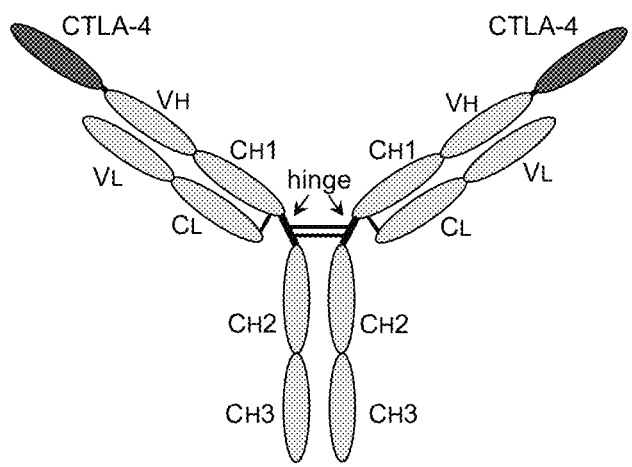
C.
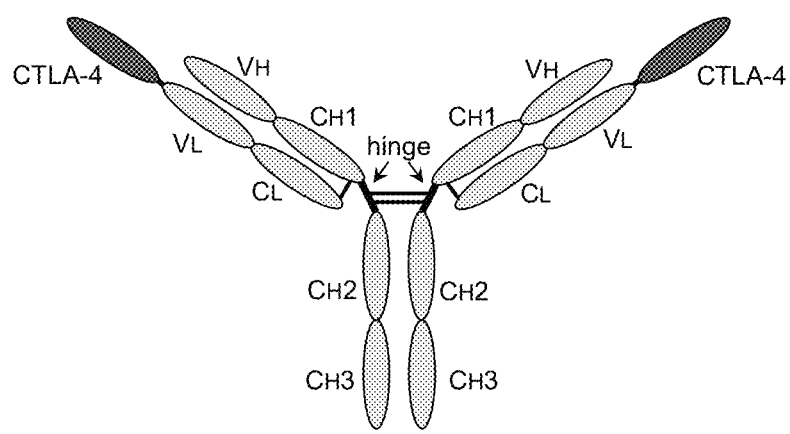

Figs. 8A, B, C
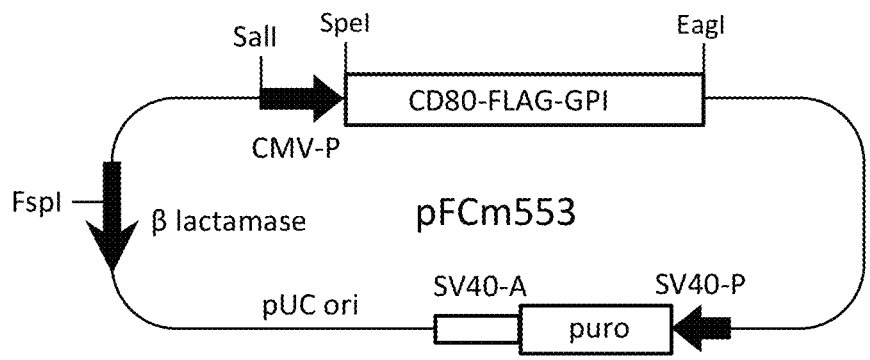
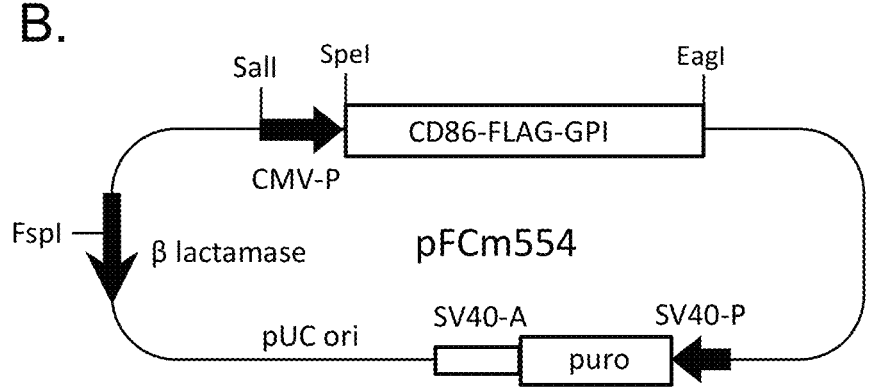
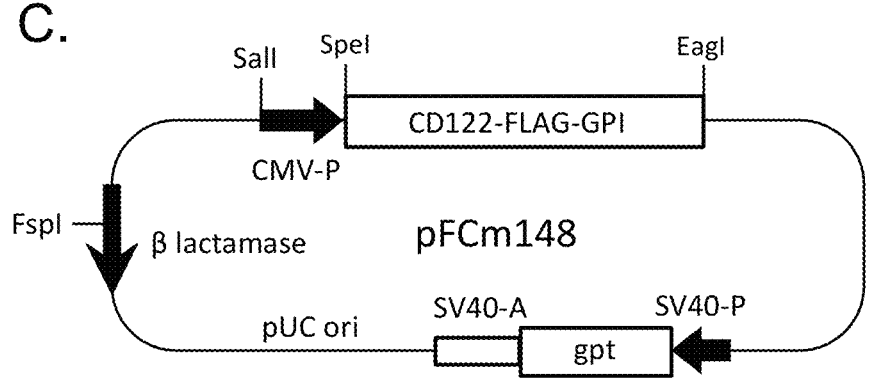

Figs. 9A, B, C
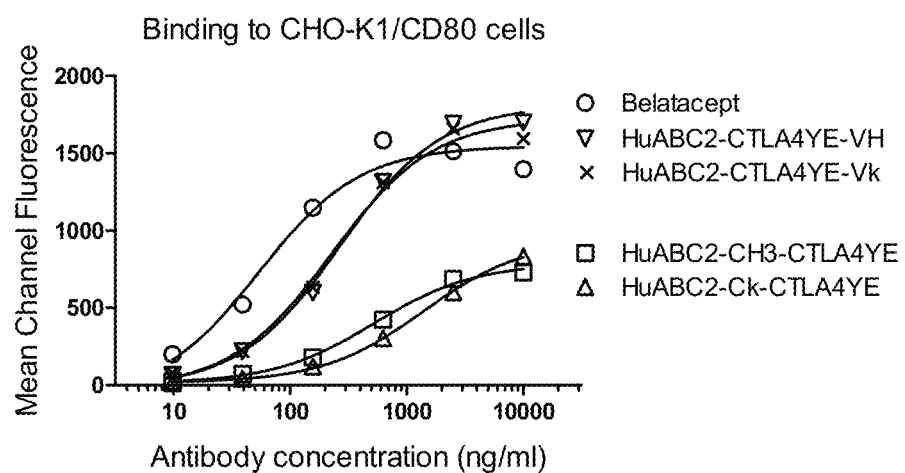
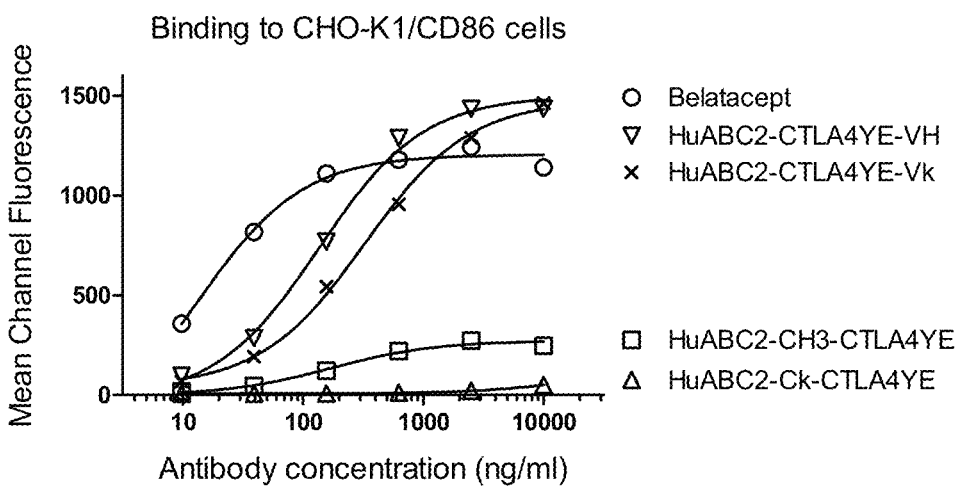
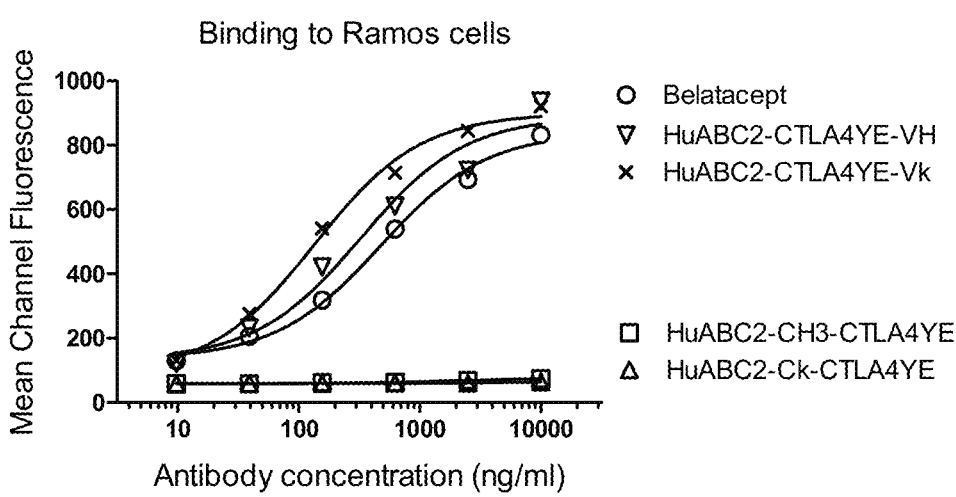

Figs. 13A, B
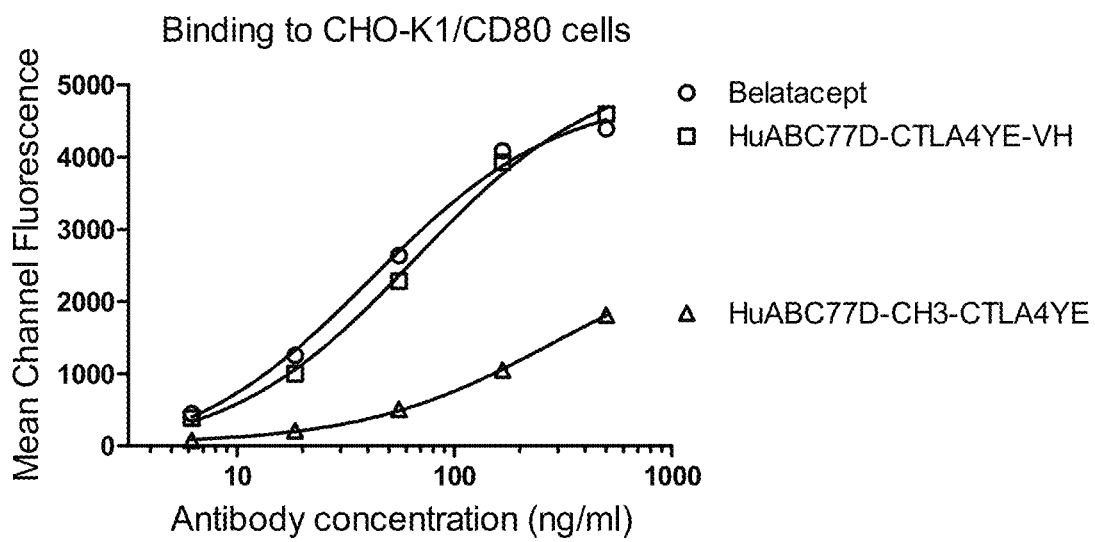
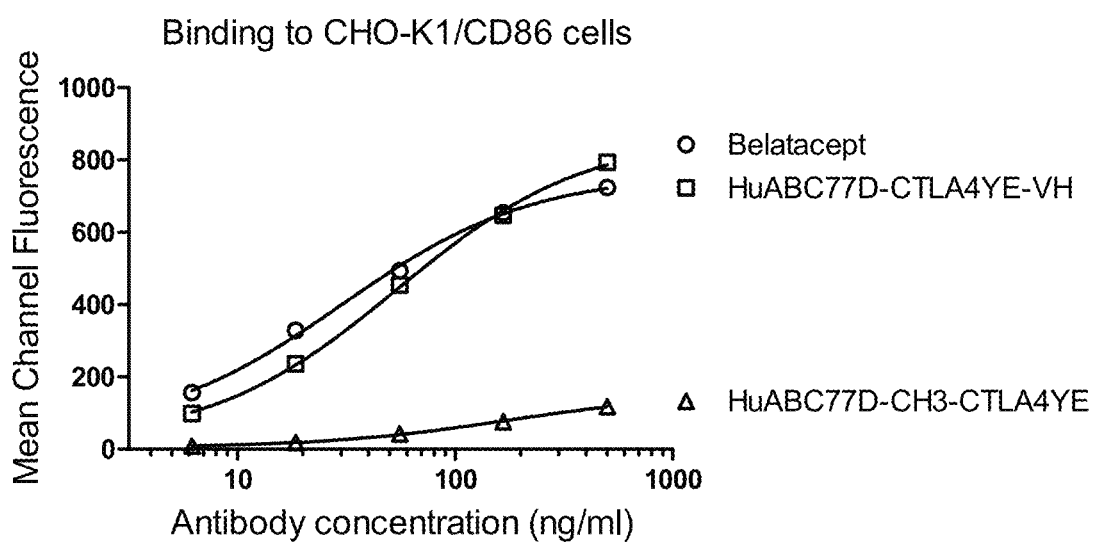

SEQUENCE LISTING

<160> NUMBER OF SEQ ID NOS: 71

<210> SEQ ID NO 1
<211> LENGTH: 140
<212> TYPE: PRT
<213> ORGANISM: Artificial sequence
<220> FEATURE:
<223> OTHER INFORMATION: Synthesized

<400> SEQUENCE: 1

```
Met Lys Leu Trp Leu Asn Trp Val Phe Leu Leu Thr Leu Leu His Gly
1               5                   10                  15

Ile Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asp Phe Tyr Met Glu Trp Val Arg Gln Ala Pro Gly Lys Gly Leu
    50                  55                  60

Glu Trp Ile Ala Ala Ser Arg Asn Lys Ala Asn Asp Tyr Thr Thr Glu
65                  70                  75                  80

Tyr Ser Ala Ser Val Lys Gly Arg Phe Ile Val Ser Arg Asp Asp Ser
                85                  90                  95

Lys Asn Ser Leu Tyr Leu Gln Met Asn Ser Leu Lys Thr Glu Asp Thr
            100                 105                 110

Ala Val Tyr Tyr Cys Ala Arg Ser Tyr Tyr Arg Tyr Asp Gly Met Asp
        115                 120                 125

Tyr Trp Gly Gln Gly Thr Thr Val Thr Val Ser Ser
    130                 135                 140
```

<210> SEQ ID NO 2
<211> LENGTH: 128
<212> TYPE: PRT
<213> ORGANISM: Artificial sequence
<220> FEATURE:
<223> OTHER INFORMATION: Synthesized

<400> SEQUENCE: 2

```
Met Asp Phe Gln Val Gln Ile Phe Ser Phe Leu Leu Ile Ser Ala Ser
1               5                   10                  15

Val Ile Val Ser Arg Gly Glu Ile Val Leu Thr Gln Ser Pro Ala Thr
            20                  25                  30
```

Leu Ser Leu Ser Pro Gly Glu Arg Ala Thr Leu Ser Cys Ser Ala Ile
    35                  40                  45

Ser Ser Val Ser Tyr Met Tyr Trp Tyr Gln Gln Lys Pro Gly Gln Ala
50                  55                  60

Pro Arg Leu Leu Ile Tyr Asp Thr Ser Asn Leu Val Ser Gly Val Pro
65                  70                  75                  80

Ala Arg Phe Ser Gly Ser Gly Ser Gly Thr Asp Tyr Thr Leu Thr Ile
                85                  90                  95

Ser Ser Leu Glu Pro Glu Asp Phe Ala Val Tyr Tyr Cys Gln Gln Trp
            100                 105                 110

Asn Thr Tyr Pro Tyr Thr Phe Gly Gly Gly Thr Lys Val Glu Ile Lys
        115                 120                 125

<210> SEQ ID NO 3
<211> LENGTH: 98
<212> TYPE: PRT
<213> ORGANISM: Homo sapiens

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 4
<211> LENGTH: 15
<212> TYPE: PRT
<213> ORGANISM: Homo sapiens

<400> SEQUENCE: 4

Glu Pro Lys Ser Cys Asp Lys Thr His Thr Cys Pro Pro Cys Pro
1               5                   10                  15

<210> SEQ ID NO 5
<211> LENGTH: 110
<212> TYPE: PRT
<213> ORGANISM: Homo sapiens

<400> SEQUENCE: 5

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 6
<211> LENGTH: 107
<212> TYPE: PRT
<213> ORGANISM: Homo sapiens

<400> SEQUENCE: 6

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 7
<211> LENGTH: 106
<212> TYPE: PRT
<213> ORGANISM: Homo sapiens

<400> SEQUENCE: 7

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 8
<211> LENGTH: 451
<212> TYPE: PRT
<213> ORGANISM: Artificial sequence
<220> FEATURE:
<223> OTHER INFORMATION: Synthesized

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Phe

```
                    20                  25                  30
Tyr Met Glu Trp Val Arg Gln Ala Pro Gly Lys Gly Leu Glu Trp Ile
                35                  40                  45
Ala Ala Ser Arg Asn Lys Ala Asn Asp Tyr Thr Thr Glu Tyr Ser Ala
 50                  55                  60
Ser Val Lys Gly Arg Phe Ile Val Ser Arg Asp Asp Ser Lys Asn Ser
 65                  70                  75                  80
Leu Tyr Leu Gln Met Asn Ser Leu Lys Thr Glu Asp Thr Ala Val Tyr
                85                  90                  95
Tyr Cys Ala Arg Ser Tyr Tyr Arg Tyr Asp Gly Met Asp Tyr Trp Gly
                100                 105                 110
Gln Gly Thr Thr Val Thr Val Ser Ser Ala Ser Thr Lys Gly Pro Ser
                115                 120                 125
Val Phe Pro Leu Ala Pro Ser Ser Lys Ser Thr Ser Gly Gly Thr Ala
                130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
                195                 200                 205
Lys Pro Ser Asn Thr Lys Val Asp Lys Val Glu Pro Lys Ser Cys
                210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
                275                 280                 285
His Asn Ala Lys Thr Lys Pro Arg Glu Glu Gln Tyr Asn Ser Thr Tyr
                290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Asp Glu Leu Thr Lys Asn Gln Val Ser
                355                 360                 365
Leu Thr Cys Leu Val Lys Gly Phe Tyr Pro Ser Asp Ile Ala Val Glu
                370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
                435                 440                 445
```

```
Pro Gly Lys
    450

<210> SEQ ID NO 9
<211> LENGTH: 213
<212> TYPE: PRT
<213> ORGANISM: Artificial sequence
<220> FEATURE:
<223> OTHER INFORMATION: Synthesized

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Ser Ala Ile Ser Ser Val Ser Tyr Met
            20                  25                  30

Tyr Trp Tyr Gln Gln Lys Pro Gly Gln Ala Pro Arg Leu Leu Ile Tyr
        35                  40                  45

Asp Thr Ser Asn Leu Val Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Asn Thr Tyr Pro Tyr Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 10
<211> LENGTH: 124
<212> TYPE: PRT
<213> ORGANISM: Homo sapiens

<400> SEQUENCE: 10

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80
```

-continued

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 11
<211> LENGTH: 7
<212> TYPE: PRT
<213> ORGANISM: Artificial sequence
<220> FEATURE:
<223> OTHER INFORMATION: Synthesized

<400> SEQUENCE: 11

Ser Gly Gly Gly Gly Ser Gly
1               5

<210> SEQ ID NO 12
<211> LENGTH: 237
<212> TYPE: PRT
<213> ORGANISM: Artificial sequence
<220> FEATURE:
<223> OTHER INFORMATION: Synthesized

<400> SEQUENCE: 12

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Ser Gly Gly Gly Gly Ser
            100                 105                 110

Gly Met His Val Ala Gln Pro Ala Val Val Leu Ala Ser Ser Arg Gly
        115                 120                 125

Ile Ala Ser Phe Val Cys Glu Tyr Ala Ser Pro Gly Lys Ala Thr Glu
    130                 135                 140

Val Arg Val Thr Val Leu Arg Gln Ala Asp Ser Gln Val Thr Glu Val
145                 150                 155                 160

Cys Ala Ala Thr Tyr Met Met Gly Asn Glu Leu Thr Phe Leu Asp Asp
                165                 170                 175

Ser Ile Cys Thr Gly Thr Ser Ser Gly Asn Gln Val Asn Leu Thr Ile
            180                 185                 190

Gln Gly Leu Arg Ala Met Asp Thr Gly Leu Tyr Ile Cys Lys Val Glu
        195                 200                 205

Leu Met Tyr Pro Pro Pro Tyr Tyr Leu Gly Ile Gly Asn Gly Thr Gln
    210                 215                 220

Ile Tyr Val Ile Asp Pro Glu Pro Cys Pro Asp Ser Asp
225                 230                 235

<210> SEQ ID NO 13

<211> LENGTH: 581
<212> TYPE: PRT
<213> ORGANISM: Artificial sequence
<220> FEATURE:
<223> OTHER INFORMATION: Synthesized

<400> SEQUENCE: 13

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Phe
            20                  25                  30

Tyr Met Glu Trp Val Arg Gln Ala Pro Gly Lys Gly Leu Glu Trp Ile
        35                  40                  45

Ala Ala Ser Arg Asn Lys Ala Asn Asp Tyr Thr Thr Glu Tyr Ser Ala
    50                  55                  60

Ser Val Lys Gly Arg Phe Ile Val Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Ser Tyr Tyr Arg Tyr Asp Gly Met Asp Tyr Trp Gly
            100                 105                 110

Gln Gly Thr Thr Val Thr Val Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380
```

```
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Ser Gly Gly Gly Ser Gly Met His Val Ala Gln Pro Ala
450                 455                 460

Val Val Leu Ala Ser Ser Arg Gly Ile Ala Ser Phe Val Cys Glu Tyr
465                 470                 475                 480

Ala Ser Pro Gly Lys Ala Thr Glu Val Arg Val Thr Val Leu Arg Gln
            485                 490                 495

Ala Asp Ser Gln Val Thr Glu Val Cys Ala Ala Thr Tyr Met Met Gly
        500                 505                 510

Asn Glu Leu Thr Phe Leu Asp Asp Ser Ile Cys Thr Gly Thr Ser Ser
    515                 520                 525

Gly Asn Gln Val Asn Leu Thr Ile Gln Gly Leu Arg Ala Met Asp Thr
530                 535                 540

Gly Leu Tyr Ile Cys Lys Val Glu Leu Met Tyr Pro Pro Pro Tyr Tyr
545                 550                 555                 560

Leu Gly Ile Gly Asn Gly Thr Gln Ile Tyr Val Ile Asp Pro Glu Pro
            565                 570                 575

Cys Pro Asp Ser Asp
        580

<210> SEQ ID NO 14
<211> LENGTH: 124
<212> TYPE: PRT
<213> ORGANISM: Homo sapiens

<400> SEQUENCE: 14

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Glu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 15
<211> LENGTH: 237
<212> TYPE: PRT
<213> ORGANISM: Artificial sequence
<220> FEATURE:
<223> OTHER INFORMATION: Synthesized
```

<400> SEQUENCE: 15

```
Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Ser Gly Gly Gly Gly Ser
            100                 105                 110

Gly Met His Val Ala Gln Pro Ala Val Val Leu Ala Ser Ser Arg Gly
        115                 120                 125

Ile Ala Ser Phe Val Cys Glu Tyr Ala Ser Pro Gly Lys Tyr Thr Glu
130                 135                 140

Val Arg Val Thr Val Leu Arg Gln Ala Asp Ser Gln Val Thr Glu Val
145                 150                 155                 160

Cys Ala Ala Thr Tyr Met Met Gly Asn Glu Leu Thr Phe Leu Asp Asp
                165                 170                 175

Ser Ile Cys Thr Gly Thr Ser Ser Gly Asn Gln Val Asn Leu Thr Ile
            180                 185                 190

Gln Gly Leu Arg Ala Met Asp Thr Gly Leu Tyr Ile Cys Lys Val Glu
        195                 200                 205

Leu Met Tyr Pro Pro Pro Tyr Tyr Glu Gly Ile Gly Asn Gly Thr Gln
210                 215                 220

Ile Tyr Val Ile Asp Pro Glu Pro Cys Pro Asp Ser Asp
225                 230                 235
```

<210> SEQ ID NO 16
<211> LENGTH: 581
<212> TYPE: PRT
<213> ORGANISM: Artificial sequence
<220> FEATURE:
<223> OTHER INFORMATION: Synthesized

<400> SEQUENCE: 16

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Phe
            20                  25                  30

Tyr Met Glu Trp Val Arg Gln Ala Pro Gly Lys Gly Leu Glu Trp Ile
        35                  40                  45

Ala Ala Ser Arg Asn Lys Ala Asn Asp Tyr Thr Thr Glu Tyr Ser Ala
    50                  55                  60

Ser Val Lys Gly Arg Phe Ile Val Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Ser Tyr Tyr Arg Tyr Asp Gly Met Asp Tyr Trp Gly
            100                 105                 110
```

-continued

```
Gln Gly Thr Thr Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
        130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Ala Ala Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Ser Gly Gly Gly Ser Gly Met His Val Ala Gln Pro Ala
    450                 455                 460
Val Val Leu Ala Ser Ser Arg Gly Ile Ala Ser Phe Val Cys Glu Tyr
465                 470                 475                 480
Ala Ser Pro Gly Lys Tyr Thr Glu Val Arg Val Thr Val Leu Arg Gln
                485                 490                 495
Ala Asp Ser Gln Val Thr Glu Val Cys Ala Ala Thr Tyr Met Met Gly
            500                 505                 510
Asn Glu Leu Thr Phe Leu Asp Asp Ser Ile Cys Thr Gly Thr Ser Ser
        515                 520                 525
Gly Asn Gln Val Asn Leu Thr Ile Gln Gly Leu Arg Ala Met Asp Thr
```

```
                    530                 535                 540
Gly Leu Tyr Ile Cys Lys Val Glu Leu Met Tyr Pro Pro Pro Tyr Tyr
545                 550                 555                 560

Glu Gly Ile Gly Asn Gly Thr Gln Ile Tyr Val Ile Asp Pro Glu Pro
                565                 570                 575

Cys Pro Asp Ser Asp
            580
```

<210> SEQ ID NO 17
<211> LENGTH: 5
<212> TYPE: PRT
<213> ORGANISM: Artificial sequence
<220> FEATURE:
<223> OTHER INFORMATION: Synthesized

<400> SEQUENCE: 17

```
Asp Phe Tyr Met Glu
1               5
```

<210> SEQ ID NO 18
<211> LENGTH: 19
<212> TYPE: PRT
<213> ORGANISM: Artificial sequence
<220> FEATURE:
<223> OTHER INFORMATION: Synthesized

<400> SEQUENCE: 18

```
Ala Ser Arg Asn Lys Ala Asn Asp Tyr Thr Thr Glu Tyr Ser Ala Ser
1               5                   10                  15

Val Lys Gly
```

<210> SEQ ID NO 19
<211> LENGTH: 10
<212> TYPE: PRT
<213> ORGANISM: Artificial sequence
<220> FEATURE:
<223> OTHER INFORMATION: Synthesized

<400> SEQUENCE: 19

```
Ser Tyr Tyr Arg Tyr Asp Gly Met Asp Tyr
1               5                   10
```

<210> SEQ ID NO 20
<211> LENGTH: 10
<212> TYPE: PRT
<213> ORGANISM: Artificial sequence
<220> FEATURE:
<223> OTHER INFORMATION: Synthesized

<400> SEQUENCE: 20

```
Ser Ala Ile Ser Ser Val Ser Tyr Met Tyr
1               5                   10
```

<210> SEQ ID NO 21
<211> LENGTH: 7
<212> TYPE: PRT
<213> ORGANISM: Artificial sequence
<220> FEATURE:
<223> OTHER INFORMATION: Synthesized

<400> SEQUENCE: 21

```
Asp Thr Ser Asn Leu Val Ser
1               5
```

```
<210> SEQ ID NO 22
<211> LENGTH: 9
<212> TYPE: PRT
<213> ORGANISM: Artificial sequence
<220> FEATURE:
<223> OTHER INFORMATION: Synthesized

<400> SEQUENCE: 22

Gln Gln Trp Asn Thr Tyr Pro Tyr Thr
1               5

<210> SEQ ID NO 23
<211> LENGTH: 7
<212> TYPE: PRT
<213> ORGANISM: Artificial sequence
<220> FEATURE:
<223> OTHER INFORMATION: Synthesized

<400> SEQUENCE: 23

Asn Asp Asn His Trp Trp Asn
1               5

<210> SEQ ID NO 24
<211> LENGTH: 16
<212> TYPE: PRT
<213> ORGANISM: Artificial sequence
<220> FEATURE:
<223> OTHER INFORMATION: Synthesized

<400> SEQUENCE: 24

Tyr Ile Asp Ser Ser Gly Ser Ser Asp Asn Asn Pro Ser Leu Lys Ser
1               5                   10                  15

<210> SEQ ID NO 25
<211> LENGTH: 11
<212> TYPE: PRT
<213> ORGANISM: Artificial sequence
<220> FEATURE:
<223> OTHER INFORMATION: Synthesized

<400> SEQUENCE: 25

Gly Gly Gly Arg Asp Tyr Tyr Gly Met Asp Tyr
1               5                   10

<210> SEQ ID NO 26
<211> LENGTH: 15
<212> TYPE: PRT
<213> ORGANISM: Artificial sequence
<220> FEATURE:
<223> OTHER INFORMATION: Synthesized

<400> SEQUENCE: 26

Arg Ala Ser Gln Ser Val Ser Thr Ser Ser Tyr Ser Tyr Val His
1               5                   10                  15

<210> SEQ ID NO 27
<211> LENGTH: 7
<212> TYPE: PRT
<213> ORGANISM: Artificial sequence
<220> FEATURE:
<223> OTHER INFORMATION: Synthesized

<400> SEQUENCE: 27

Tyr Ala Ser Asn Leu Glu Ser
1               5

<210> SEQ ID NO 28
```

```
<211> LENGTH: 9
<212> TYPE: PRT
<213> ORGANISM: Artificial sequence
<220> FEATURE:
<223> OTHER INFORMATION: Synthesized

<400> SEQUENCE: 28

Gln His Ser Trp Asp Ile Pro Phe Thr
1               5

<210> SEQ ID NO 29
<211> LENGTH: 121
<212> TYPE: PRT
<213> ORGANISM: Artificial sequence
<220> FEATURE:
<223> OTHER INFORMATION: Synthesized

<400> SEQUENCE: 29

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Asn Asp
            20                  25                  30

Asn His Trp Trp Asn Trp Ile Arg Gln His Pro Gly Lys Gly Leu Glu
        35                  40                  45

Trp Met Gly Tyr Ile Asp Ser Ser Gly Ser Ser Asp Asn Asn Pro Ser
    50                  55                  60

Leu Lys Ser Gln Ile Thr Ile Ser Arg Asp Thr Ser Lys Asn Gln Leu
65                  70                  75                  80

Ser Leu Lys Leu Ser Ser Val Thr Ala Ala Asp Thr Ala Val Tyr Tyr
                85                  90                  95

Cys Ala Arg Gly Gly Gly Arg Asp Tyr Tyr Gly Met Asp Tyr Trp Gly
            100                 105                 110

Gln Gly Thr Thr Val Thr Val Ser Ser
        115                 120

<210> SEQ ID NO 30
<211> LENGTH: 111
<212> TYPE: PRT
<213> ORGANISM: Artificial sequence
<220> FEATURE:
<223> OTHER INFORMATION: Synthesized

<400> SEQUENCE: 30

Asp Ile Val Met Thr Gln Ser Pro Asp Ser Leu Gly Val Ser Leu Gly
1               5                   10                  15

Glu Arg Ala Thr Ile Asn Cys Arg Ala Ser Gln Ser Val Ser Thr Ser
            20                  25                  30

Ser Tyr Ser Tyr Val His Trp Tyr Gln Gln Lys Pro Gly Gln Pro Pro
        35                  40                  45

Lys Leu Leu Ile Lys Tyr Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Asp Ile Pro Phe Thr Phe Gly Gln Gly Thr Lys Leu Glu Ile Lys
            100                 105                 110

<210> SEQ ID NO 31
<211> LENGTH: 525
```

<212> TYPE: PRT
<213> ORGANISM: Homo sapiens

<400> SEQUENCE: 31

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser His Tyr Phe Glu Arg His Leu Glu Phe Glu Ala Arg
130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr Ile Pro Trp Leu Gly His Leu Leu Val Gly
    210                 215                 220

Leu Ser Gly Ala Phe Gly Phe Ile Ile Leu Val Tyr Leu Leu Ile Asn
225                 230                 235                 240

Cys Arg Asn Thr Gly Pro Trp Leu Lys Lys Val Leu Lys Cys Asn Thr
                245                 250                 255

Pro Asp Pro Ser Lys Phe Phe Ser Gln Leu Ser Ser Glu His Gly Gly
            260                 265                 270

Asp Val Gln Lys Trp Leu Ser Ser Pro Phe Pro Ser Ser Ser Phe Ser
        275                 280                 285

Pro Gly Gly Leu Ala Pro Glu Ile Ser Pro Leu Glu Val Leu Glu Arg
    290                 295                 300

Asp Lys Val Thr Gln Leu Leu Leu Gln Gln Asp Lys Val Pro Glu Pro
305                 310                 315                 320

Ala Ser Leu Ser Ser Asn His Ser Leu Thr Ser Cys Phe Thr Asn Gln
                325                 330                 335

Gly Tyr Phe Phe Phe His Leu Pro Asp Ala Leu Glu Ile Glu Ala Cys
            340                 345                 350

Gln Val Tyr Phe Thr Tyr Asp Pro Tyr Ser Glu Glu Asp Pro Asp Glu
        355                 360                 365

Gly Val Ala Gly Ala Pro Thr Gly Ser Ser Pro Gln Pro Leu Gln Pro
    370                 375                 380

Leu Ser Gly Glu Asp Asp Ala Tyr Cys Thr Phe Pro Ser Arg Asp Asp
385                 390                 395                 400

```
Leu Leu Leu Phe Ser Pro Ser Leu Gly Gly Pro Ser Pro Pro Ser
                405                 410                 415

Thr Ala Pro Gly Gly Ser Gly Ala Gly Glu Arg Met Pro Pro Ser
            420                 425                 430

Leu Gln Glu Arg Val Pro Arg Asp Trp Asp Pro Gln Pro Leu Gly Pro
        435                 440                 445

Pro Thr Pro Gly Val Pro Asp Leu Val Asp Phe Gln Pro Pro Glu
    450                 455                 460

Leu Val Leu Arg Glu Ala Gly Glu Val Pro Asp Ala Gly Pro Arg
465                 470                 475                 480

Glu Gly Val Ser Phe Pro Trp Ser Arg Pro Gly Gln Gly Glu Phe
                485                 490                 495

Arg Ala Leu Asn Ala Arg Leu Pro Leu Asn Thr Asp Ala Tyr Leu Ser
            500                 505                 510

Leu Gln Glu Leu Gln Gly Gln Asp Pro Thr His Leu Val
        515                 520                 525

<210> SEQ ID NO 32
<211> LENGTH: 238
<212> TYPE: PRT
<213> ORGANISM: Artificial sequence
<220> FEATURE:
<223> OTHER INFORMATION: Synthesized

<400> SEQUENCE: 32

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys Ser Gly Gly Gly Gly
            100                 105                 110

Ser Gly Met His Val Ala Gln Pro Ala Val Val Leu Ala Ser Ser Arg
        115                 120                 125

Gly Ile Ala Ser Phe Val Cys Glu Tyr Ala Ser Pro Gly Lys Tyr Thr
    130                 135                 140

Glu Val Arg Val Thr Val Leu Arg Gln Ala Asp Ser Gln Val Thr Glu
145                 150                 155                 160

Val Cys Ala Ala Thr Tyr Met Met Gly Asn Glu Leu Thr Phe Leu Asp
                165                 170                 175

Asp Ser Ile Cys Thr Gly Thr Ser Ser Gly Asn Gln Val Asn Leu Thr
            180                 185                 190

Ile Gln Gly Leu Arg Ala Met Asp Thr Gly Leu Tyr Ile Cys Lys Val
        195                 200                 205

Glu Leu Met Tyr Pro Pro Pro Tyr Tyr Glu Gly Ile Gly Asn Gly Thr
    210                 215                 220

Gln Ile Tyr Val Ile Asp Pro Glu Pro Cys Pro Asp Ser Asp
225                 230                 235
```

<210> SEQ ID NO 33
<211> LENGTH: 451
<212> TYPE: PRT
<213> ORGANISM: Artificial sequence
<220> FEATURE:
<223> OTHER INFORMATION: Synthesized

<400> SEQUENCE: 33

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Phe
            20                  25                  30

Tyr Met Glu Trp Val Arg Gln Ala Pro Gly Lys Gly Leu Glu Trp Ile
        35                  40                  45

Ala Ala Ser Arg Asn Lys Ala Asn Asp Tyr Thr Thr Glu Tyr Ser Ala
    50                  55                  60

Ser Val Lys Gly Arg Phe Ile Val Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Ser Tyr Tyr Arg Tyr Asp Gly Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365
```

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 34
<211> LENGTH: 344
<212> TYPE: PRT
<213> ORGANISM: Artificial sequence
<220> FEATURE:
<223> OTHER INFORMATION: Synthesized

<400> SEQUENCE: 34

Glu Ile Val Leu Thr Gln Ser Pro Ala Thr Leu Ser Leu Ser Pro Gly
1               5                   10                  15

Glu Arg Ala Thr Leu Ser Cys Ser Ala Ile Ser Ser Val Ser Tyr Met
            20                  25                  30

Tyr Trp Tyr Gln Gln Lys Pro Gly Gln Ala Pro Arg Leu Leu Ile Tyr
        35                  40                  45

Asp Thr Ser Asn Leu Val Ser Gly Val Pro Ala Arg Phe Ser Gly Ser
    50                  55                  60

Gly Ser Gly Thr Asp Tyr Thr Leu Thr Ile Ser Leu Glu Pro Glu
65                  70                  75                  80

Asp Phe Ala Val Tyr Tyr Cys Gln Gln Trp Asn Thr Tyr Pro Tyr Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Ser Gly Gly Gly Ser Gly Met His Val Ala
    210                 215                 220

Gln Pro Ala Val Val Leu Ala Ser Ser Arg Gly Ile Ala Ser Phe Val
225                 230                 235                 240

Cys Glu Tyr Ala Ser Pro Gly Lys Tyr Thr Glu Val Arg Val Thr Val
                245                 250                 255

Leu Arg Gln Ala Asp Ser Gln Val Thr Glu Val Cys Ala Ala Thr Tyr
            260                 265                 270

```
Met Met Gly Asn Glu Leu Thr Phe Leu Asp Asp Ser Ile Cys Thr Gly
            275                 280                 285

Thr Ser Ser Gly Asn Gln Val Asn Leu Thr Ile Gln Gly Leu Arg Ala
        290                 295                 300

Met Asp Thr Gly Leu Tyr Ile Cys Lys Val Glu Leu Met Tyr Pro Pro
305                 310                 315                 320

Pro Tyr Tyr Glu Gly Ile Gly Asn Gly Thr Gln Ile Tyr Val Ile Asp
                325                 330                 335

Pro Glu Pro Cys Pro Asp Ser Asp
            340

<210> SEQ ID NO 35
<211> LENGTH: 19
<212> TYPE: PRT
<213> ORGANISM: Artificial sequence
<220> FEATURE:
<223> OTHER INFORMATION: Synthesized

<400> SEQUENCE: 35

Met Gly Trp Ser Trp Ile Phe Phe Phe Leu Leu Ser Gly Thr Ala Ser
1               5                   10                  15

Val Leu Ser

<210> SEQ ID NO 36
<211> LENGTH: 11
<212> TYPE: PRT
<213> ORGANISM: Artificial sequence
<220> FEATURE:
<223> OTHER INFORMATION: Synthesized

<400> SEQUENCE: 36

Ser Gly Gly Gly Gly Ser Gly Gly Gly Gly Ser
1               5                   10

<210> SEQ ID NO 37
<211> LENGTH: 121
<212> TYPE: PRT
<213> ORGANISM: Artificial sequence
<220> FEATURE:
<223> OTHER INFORMATION: Synthesized

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Phe
            20                  25                  30

Tyr Met Glu Trp Val Arg Gln Ala Pro Gly Lys Gly Leu Glu Trp Ile
        35                  40                  45

Ala Ala Ser Arg Asn Lys Ala Asn Asp Tyr Thr Thr Glu Tyr Ser Ala
    50                  55                  60

Ser Val Lys Gly Arg Phe Ile Val Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Ser Tyr Tyr Arg Tyr Asp Gly Met Asp Tyr Trp Gly
            100                 105                 110

Gln Gly Thr Thr Val Thr Val Ser Ser
        115                 120
```

```
<210> SEQ ID NO 38
<211> LENGTH: 275
<212> TYPE: PRT
<213> ORGANISM: Artificial sequence
<220> FEATURE:
<223> OTHER INFORMATION: Synthesized

<400> SEQUENCE: 38

Met Gly Trp Ser Trp Ile Phe Phe Phe Leu Leu Ser Gly Thr Ala Ser
1               5                   10                  15

Val Leu Ser Met His Val Ala Gln Pro Ala Val Val Leu Ala Ser Ser
            20                  25                  30

Arg Gly Ile Ala Ser Phe Val Cys Glu Tyr Ala Ser Pro Gly Lys Tyr
        35                  40                  45

Thr Glu Val Arg Val Thr Val Leu Arg Gln Ala Asp Ser Gln Val Thr
    50                  55                  60

Glu Val Cys Ala Ala Thr Tyr Met Met Gly Asn Glu Leu Thr Phe Leu
65                  70                  75                  80

Asp Asp Ser Ile Cys Thr Gly Thr Ser Ser Gly Asn Gln Val Asn Leu
                85                  90                  95

Thr Ile Gln Gly Leu Arg Ala Met Asp Thr Gly Leu Tyr Ile Cys Lys
            100                 105                 110

Val Glu Leu Met Tyr Pro Pro Pro Tyr Tyr Glu Gly Ile Gly Asn Gly
        115                 120                 125

Thr Gln Ile Tyr Val Ile Asp Pro Glu Pro Cys Pro Asp Ser Asp Ser
    130                 135                 140

Gly Gly Gly Gly Ser Gly Gly Gly Ser Glu Val Gln Leu Val Glu
145                 150                 155                 160

Ser Gly Gly Gly Leu Val Gln Pro Gly Gly Ser Leu Arg Leu Ser Cys
                165                 170                 175

Ala Ala Ser Gly Phe Thr Phe Ser Asp Phe Tyr Met Glu Trp Val Arg
            180                 185                 190

Gln Ala Pro Gly Lys Gly Leu Glu Trp Ile Ala Ala Ser Arg Asn Lys
        195                 200                 205

Ala Asn Asp Tyr Thr Thr Glu Tyr Ser Ala Ser Val Lys Gly Arg Phe
    210                 215                 220

Ile Val Ser Arg Asp Asp Ser Lys Asn Ser Leu Tyr Leu Gln Met Asn
225                 230                 235                 240

Ser Leu Lys Thr Glu Asp Thr Ala Val Tyr Tyr Cys Ala Arg Ser Tyr
                245                 250                 255

Tyr Arg Tyr Asp Gly Met Asp Val Trp Gly Gln Gly Thr Thr Val Thr
            260                 265                 270

Val Ser Ser
        275

<210> SEQ ID NO 39
<211> LENGTH: 586
<212> TYPE: PRT
<213> ORGANISM: Artificial sequence
<220> FEATURE:
<223> OTHER INFORMATION: Synthesized

<400> SEQUENCE: 39

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
            20                  25                  30
```

```
Arg Val Thr Val Leu Arg Gln Ala Asp Ser Gln Val Thr Glu Val Cys
             35                  40                  45

Ala Ala Thr Tyr Met Met Gly Asn Glu Leu Thr Phe Leu Asp Asp Ser
 50                      55                  60

Ile Cys Thr Gly Thr Ser Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Glu Gly Ile Gly Asn Gly Thr Gln Ile
             100                 105                 110

Tyr Val Ile Asp Pro Glu Pro Cys Pro Asp Ser Asp Ser Gly Gly Gly
             115                 120                 125

Gly Ser Gly Gly Gly Gly Ser Glu Val Gln Leu Val Glu Ser Gly Gly
130                 135                 140

Gly Leu Val Gln Pro Gly Gly Ser Leu Arg Leu Ser Cys Ala Ala Ser
145                 150                 155                 160

Gly Phe Thr Phe Ser Asp Phe Tyr Met Glu Trp Val Arg Gln Ala Pro
                165                 170                 175

Gly Lys Gly Leu Glu Trp Ile Ala Ala Ser Arg Asn Lys Ala Asn Asp
            180                 185                 190

Tyr Thr Thr Glu Tyr Ser Ala Ser Val Lys Gly Arg Phe Ile Val Ser
            195                 200                 205

Arg Asp Asp Ser Lys Asn Ser Leu Tyr Leu Gln Met Asn Ser Leu Lys
    210                 215                 220

Thr Glu Asp Thr Ala Val Tyr Tyr Cys Ala Arg Ser Tyr Tyr Arg Tyr
225                 230                 235                 240

Asp Gly Met Asp Tyr Trp Gly Gln Gly Thr Thr Val Thr Val Ser Ser
                245                 250                 255

Ala Ser Thr Lys Gly Pro Ser Val Phe Pro Leu Ala Pro Ser Ser Lys
            260                 265                 270

Ser Thr Ser Gly Gly Thr Ala Ala Leu Gly Cys Leu Val Lys Asp Tyr
            275                 280                 285

Phe Pro Glu Pro Val Thr Val Ser Trp Asn Ser Gly Ala Leu Thr Ser
    290                 295                 300

Gly Val His Thr Phe Pro Ala Val Leu Gln Ser Ser Gly Leu Tyr Ser
305                 310                 315                 320

Leu Ser Ser Val Val Thr Val Pro Ser Ser Ser Leu Gly Thr Gln Thr
                325                 330                 335

Tyr Ile Cys Asn Val Asn His Lys Pro Ser Asn Thr Lys Val Asp Lys
            340                 345                 350

Lys Val Glu Pro Lys Ser Cys Asp Lys Thr His Thr Cys Pro Pro Cys
            355                 360                 365

Pro Ala Pro Glu Ala Ala Gly Gly Pro Ser Val Phe Leu Phe Pro Pro
    370                 375                 380

Lys Pro Lys Asp Thr Leu Met Ile Ser Arg Thr Pro Glu Val Thr Cys
385                 390                 395                 400

Val Val Val Asp Val Ser His Glu Asp Pro Glu Val Lys Phe Asn Trp
                405                 410                 415

Tyr Val Asp Gly Val Glu Val His Asn Ala Lys Thr Lys Pro Arg Glu
            420                 425                 430

Glu Gln Tyr Asn Ser Thr Tyr Arg Val Val Ser Val Leu Thr Val Leu
            435                 440                 445

His Gln Asp Trp Leu Asn Gly Lys Glu Tyr Lys Cys Lys Val Ser Asn
```

```
                450                 455                 460
Lys Ala Leu Pro Ala Pro Ile Glu Lys Thr Ile Ser Lys Ala Lys Gly
465                 470                 475                 480

Gln Pro Arg Glu Pro Gln Val Tyr Thr Leu Pro Pro Ser Arg Asp Glu
                485                 490                 495

Leu Thr Lys Asn Gln Val Ser Leu Thr Cys Leu Val Lys Gly Phe Tyr
                500                 505                 510

Pro Ser Asp Ile Ala Val Glu Trp Glu Ser Asn Gly Gln Pro Glu Asn
                515                 520                 525

Asn Tyr Lys Thr Thr Pro Pro Val Leu Asp Ser Asp Gly Ser Phe Phe
                530                 535                 540

Leu Tyr Ser Lys Leu Thr Val Asp Lys Ser Arg Trp Gln Gln Gly Asn
545                 550                 555                 560

Val Phe Ser Cys Ser Val Met His Glu Ala Leu His Asn His Tyr Thr
                565                 570                 575

Gln Lys Ser Leu Ser Leu Ser Pro Gly Lys
                580                 585

<210> SEQ ID NO 40
<211> LENGTH: 106
<212> TYPE: PRT
<213> ORGANISM: Artificial sequence
<220> FEATURE:
<223> OTHER INFORMATION: Synthesized

<400> SEQUENCE: 40

Glu Ile Val Leu Thr Gln Ser Pro Ala Thr Leu Ser Leu Ser Pro Gly
1               5                   10                  15

Glu Arg Ala Thr Leu Ser Cys Ser Ala Ile Ser Ser Val Ser Tyr Met
                20                  25                  30

Tyr Trp Tyr Gln Gln Lys Pro Gly Gln Ala Pro Arg Leu Leu Ile Tyr
            35                  40                  45

Asp Thr Ser Asn Leu Val Ser Gly Val Pro Ala Arg Phe Ser Gly Ser
        50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Asn Thr Tyr Pro Tyr Thr
                85                  90                  95

Phe Gly Gly Gly Thr Lys Val Glu Ile Lys
            100                 105

<210> SEQ ID NO 41
<211> LENGTH: 241
<212> TYPE: PRT
<213> ORGANISM: Artificial sequence
<220> FEATURE:
<223> OTHER INFORMATION: Synthesized

<400> SEQUENCE: 41

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60
```

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Tyr Tyr Glu Gly Ile Gly Asn Gly Thr Gln Ile
                100                 105                 110

Tyr Val Ile Asp Pro Glu Pro Cys Pro Asp Ser Asp Ser Gly Gly Gly
            115                 120                 125

Gly Ser Gly Gly Gly Gly Ser Glu Ile Val Leu Thr Gln Ser Pro Ala
130                 135                 140

Thr Leu Ser Leu Ser Pro Gly Glu Arg Ala Thr Leu Ser Cys Ser Ala
145                 150                 155                 160

Ile Ser Ser Val Ser Tyr Met Tyr Trp Tyr Gln Gln Lys Pro Gly Gln
                165                 170                 175

Ala Pro Arg Leu Leu Ile Tyr Asp Thr Ser Asn Leu Val Ser Gly Val
            180                 185                 190

Pro Ala Arg Phe Ser Gly Ser Gly Ser Gly Thr Asp Tyr Thr Leu Thr
            195                 200                 205

Ile Ser Ser Leu Glu Pro Glu Asp Phe Ala Val Tyr Tyr Cys Gln Gln
210                 215                 220

Trp Asn Thr Tyr Pro Tyr Thr Phe Gly Gly Gly Thr Lys Val Glu Ile
225                 230                 235                 240

Lys

<210> SEQ ID NO 42
<211> LENGTH: 348
<212> TYPE: PRT
<213> ORGANISM: Artificial sequence
<220> FEATURE:
<223> OTHER INFORMATION: Synthesized

<400> SEQUENCE: 42

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Glu Gly Ile Gly Asn Gly Thr Gln Ile
                100                 105                 110

Tyr Val Ile Asp Pro Glu Pro Cys Pro Asp Ser Asp Ser Gly Gly Gly
            115                 120                 125

Gly Ser Gly Gly Gly Gly Ser Glu Ile Val Leu Thr Gln Ser Pro Ala
130                 135                 140

Thr Leu Ser Leu Ser Pro Gly Glu Arg Ala Thr Leu Ser Cys Ser Ala
145                 150                 155                 160

Ile Ser Ser Val Ser Tyr Met Tyr Trp Tyr Gln Gln Lys Pro Gly Gln
                165                 170                 175

Ala Pro Arg Leu Leu Ile Tyr Asp Thr Ser Asn Leu Val Ser Gly Val

```
            180                 185                 190
Pro Ala Arg Phe Ser Gly Ser Gly Ser Gly Thr Asp Tyr Thr Leu Thr
                195                 200                 205

Ile Ser Ser Leu Glu Pro Glu Asp Phe Ala Val Tyr Tyr Cys Gln Gln
            210                 215                 220

Trp Asn Thr Tyr Pro Tyr Thr Phe Gly Gly Gly Thr Lys Val Glu Ile
225                 230                 235                 240

Lys Arg Thr Val Ala Ala Pro Ser Val Phe Ile Phe Pro Pro Ser Asp
                245                 250                 255

Glu Gln Leu Lys Ser Gly Thr Ala Ser Val Val Cys Leu Leu Asn Asn
            260                 265                 270

Phe Tyr Pro Arg Glu Ala Lys Val Gln Trp Lys Val Asp Asn Ala Leu
            275                 280                 285

Gln Ser Gly Asn Ser Gln Glu Ser Val Thr Glu Gln Asp Ser Lys Asp
            290                 295                 300

Ser Thr Tyr Ser Leu Ser Ser Thr Leu Thr Leu Ser Lys Ala Asp Tyr
305                 310                 315                 320

Glu Lys His Lys Val Tyr Ala Cys Glu Val Thr His Gln Gly Leu Ser
                325                 330                 335

Ser Pro Val Thr Lys Ser Phe Asn Arg Gly Glu Cys
            340                 345

<210> SEQ ID NO 43
<211> LENGTH: 208
<212> TYPE: PRT
<213> ORGANISM: Homo sapiens

<400> SEQUENCE: 43

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205
```

<210> SEQ ID NO 44
<211> LENGTH: 8
<212> TYPE: PRT
<213> ORGANISM: Artificial sequence
<220> FEATURE:
<223> OTHER INFORMATION: Synthesized

<400> SEQUENCE: 44

```
Asp Tyr Lys Asp Asp Asp Asp Lys
1               5
```

<210> SEQ ID NO 45
<211> LENGTH: 37
<212> TYPE: PRT
<213> ORGANISM: Artificial sequence
<220> FEATURE:
<223> OTHER INFORMATION: Synthesized

<400> SEQUENCE: 45

```
Pro Asn Lys Gly Ser Gly Thr Thr Ser Gly Thr Thr Arg Leu Leu Ser
1               5                   10                  15

Gly His Thr Cys Phe Thr Leu Thr Gly Leu Leu Gly Thr Leu Val Thr
            20                  25                  30

Met Gly Leu Leu Thr
        35
```

<210> SEQ ID NO 46
<211> LENGTH: 260
<212> TYPE: PRT
<213> ORGANISM: Artificial sequence
<220> FEATURE:
<223> OTHER INFORMATION: Synthesized

<400> SEQUENCE: 46

```
Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
```

```
                195                 200                 205
Thr Gly Gly Asp Tyr Lys Asp Asp Asp Lys Gly Gly Pro
    210                 215                 220

Asn Lys Gly Ser Gly Thr Thr Ser Gly Thr Thr Arg Leu Leu Ser Gly
225                 230                 235                 240

His Thr Cys Phe Thr Leu Thr Gly Leu Leu Gly Thr Leu Val Thr Met
                245                 250                 255

Gly Leu Leu Thr
            260

<210> SEQ ID NO 47
<211> LENGTH: 220
<212> TYPE: PRT
<213> ORGANISM: Homo sapiens

<400> SEQUENCE: 47

Leu Lys Ile Gln Ala Tyr Phe Asn Glu Thr Ala Asp Leu Pro Cys Gln
1               5                   10                  15

Phe Ala Asn Ser Gln Asn Gln Ser Leu Ser Glu Leu Val Val Phe Trp
            20                  25                  30

Gln Asp Gln Glu Asn Leu Val Leu Asn Glu Val Tyr Leu Gly Lys Glu
        35                  40                  45

Lys Phe Asp Ser Val His Ser Lys Tyr Met Gly Arg Thr Ser Phe Asp
50                  55                  60

Ser Asp Ser Trp Thr Leu Arg Leu His Asn Leu Gln Ile Lys Asp Lys
65                  70                  75                  80

Gly Leu Tyr Gln Cys Ile Ile His His Lys Lys Pro Thr Gly Met Ile
                85                  90                  95

Arg Ile His Gln Met Asn Ser Glu Leu Ser Val Leu Ala Asn Phe Ser
            100                 105                 110

Gln Pro Glu Ile Val Pro Ile Ser Asn Ile Thr Glu Asn Val Tyr Ile
        115                 120                 125

Asn Leu Thr Cys Ser Ser Ile His Gly Tyr Pro Glu Pro Lys Lys Met
130                 135                 140

Ser Val Leu Leu Arg Thr Lys Asn Ser Thr Ile Glu Tyr Asp Gly Ile
145                 150                 155                 160

Met Gln Lys Ser Gln Asp Asn Val Thr Glu Leu Tyr Asp Val Ser Ile
                165                 170                 175

Ser Leu Ser Val Ser Phe Pro Asp Val Thr Ser Asn Met Thr Ile Phe
            180                 185                 190

Cys Ile Leu Glu Thr Asp Lys Thr Arg Leu Leu Ser Ser Pro Phe Ser
        195                 200                 205

Ile Glu Leu Glu Asp Pro Gln Pro Pro Pro Asp His
210                 215                 220

<210> SEQ ID NO 48
<211> LENGTH: 272
<212> TYPE: PRT
<213> ORGANISM: Artificial sequence
<220> FEATURE:
<223> OTHER INFORMATION: Synthesized

<400> SEQUENCE: 48

Leu Lys Ile Gln Ala Tyr Phe Asn Glu Thr Ala Asp Leu Pro Cys Gln
1               5                   10                  15

Phe Ala Asn Ser Gln Asn Gln Ser Leu Ser Glu Leu Val Val Phe Trp
            20                  25                  30
```

```
Gln Asp Gln Glu Asn Leu Val Leu Asn Glu Val Tyr Leu Gly Lys Glu
            35                  40                  45

Lys Phe Asp Ser Val His Ser Lys Tyr Met Gly Arg Thr Ser Phe Asp
         50                  55                  60

Ser Asp Ser Trp Thr Leu Arg Leu His Asn Leu Gln Ile Lys Asp Lys
 65                  70                  75                  80

Gly Leu Tyr Gln Cys Ile Ile His His Lys Lys Pro Thr Gly Met Ile
                 85                  90                  95

Arg Ile His Gln Met Asn Ser Glu Leu Ser Val Leu Ala Asn Phe Ser
            100                 105                 110

Gln Pro Glu Ile Val Pro Ile Ser Asn Ile Thr Glu Asn Val Tyr Ile
        115                 120                 125

Asn Leu Thr Cys Ser Ser Ile His Gly Tyr Pro Glu Pro Lys Lys Met
    130                 135                 140

Ser Val Leu Leu Arg Thr Lys Asn Ser Thr Ile Glu Tyr Asp Gly Ile
145                 150                 155                 160

Met Gln Lys Ser Gln Asp Asn Val Thr Glu Leu Tyr Asp Val Ser Ile
                165                 170                 175

Ser Leu Ser Val Ser Phe Pro Asp Val Thr Ser Asn Met Thr Ile Phe
            180                 185                 190

Cys Ile Leu Glu Thr Asp Lys Thr Arg Leu Leu Ser Ser Pro Phe Ser
        195                 200                 205

Ile Glu Leu Glu Asp Pro Gln Pro Pro Pro Asp His Thr Gly Gly Gly
    210                 215                 220

Asp Tyr Lys Asp Asp Asp Asp Lys Gly Gly Pro Asn Lys Gly Ser
225                 230                 235                 240

Gly Thr Thr Ser Gly Thr Thr Arg Leu Leu Ser Gly His Thr Cys Phe
                245                 250                 255

Thr Leu Thr Gly Leu Leu Gly Thr Leu Val Thr Met Gly Leu Leu Thr
            260                 265                 270

<210> SEQ ID NO 49
<211> LENGTH: 357
<212> TYPE: PRT
<213> ORGANISM: Artificial sequence
<220> FEATURE:
<223> OTHER INFORMATION: Synthesized

<400> SEQUENCE: 49

Met His Val Ala Gln Pro Ala Val Val Leu Ala Ser Ser Arg Gly Ile
  1               5                  10                  15

Ala Ser Phe Val Cys Glu Tyr Ala Ser Pro Gly Lys Tyr Thr Glu Val
             20                  25                  30

Arg Val Thr Val Leu Arg Gln Ala Asp Ser Gln Val Thr Glu Val Cys
         35                  40                  45

Ala Ala Thr Tyr Met Met Gly Asn Glu Leu Thr Phe Leu Asp Asp Ser
     50                  55                  60

Ile Cys Thr Gly Thr Ser Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp Gln Glu Pro Lys
        115                 120                 125
```

```
Ser Ser Asp Lys Thr His Thr Ser Pro Pro Ser Pro Ala Pro Glu Leu
    130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 50
<211> LENGTH: 16
<212> TYPE: PRT
<213> ORGANISM: Artificial sequence
<220> FEATURE:
<223> OTHER INFORMATION: Synthesized

<400> SEQUENCE: 50

Ser Gly Gly Gly Gly Ser Gly Gly Gly Gly Ser Gly Gly Gly Gly Ser
1               5                   10                  15

<210> SEQ ID NO 51
<211> LENGTH: 214
<212> TYPE: PRT
<213> ORGANISM: Homo sapiens

<400> SEQUENCE: 51

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Arg Trp Asn Gln Thr Cys
        35                  40                  45

Glu Leu Leu Pro Val Ser Gln Ala Ser Trp Ala Cys Asn Leu Ile Leu
    50                  55                  60
```

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr
    210

<210> SEQ ID NO 52
<211> LENGTH: 266
<212> TYPE: PRT
<213> ORGANISM: Artificial sequence
<220> FEATURE:
<223> OTHER INFORMATION: Synthesized

<400> SEQUENCE: 52

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
                20                  25                  30

Cys Gln Val His Ala Trp Pro Asp Arg Arg Arg Trp Asn Gln Thr Cys
            35                  40                  45

Glu Leu Leu Pro Val Ser Gln Ala Ser Trp Ala Cys Asn Leu Ile Leu
        50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

```
Ala Leu Gly Lys Asp Thr Thr Gly Gly Asp Tyr Lys Asp Asp Asp
    210             215                 220
Asp Lys Gly Gly Gly Pro Asn Lys Gly Ser Gly Thr Thr Ser Gly Thr
225             230                 235                 240
Thr Arg Leu Leu Ser Gly His Thr Cys Phe Thr Leu Thr Gly Leu Leu
            245                 250                 255
Gly Thr Leu Val Thr Met Gly Leu Leu Thr
            260                 265
```

<210> SEQ ID NO 53
<211> LENGTH: 451
<212> TYPE: PRT
<213> ORGANISM: Artificial sequence
<220> FEATURE:
<223> OTHER INFORMATION: Synthesized

<400> SEQUENCE: 53

```
Gln Val Gln Leu Gln Glu Ser Gly Pro Gly Leu Val Lys Pro Ser Gln
1               5                   10                  15
Thr Leu Ser Leu Thr Cys Thr Val Ser Gly Tyr Ser Ile Thr Asn Asp
            20                  25                  30
Asn His Trp Trp Asn Trp Ile Arg Gln His Pro Gly Lys Gly Leu Glu
        35                  40                  45
Trp Met Gly Tyr Ile Asp Ser Ser Gly Ser Ser Asp Asn Asn Pro Ser
    50                  55                  60
Leu Lys Ser Gln Ile Thr Ile Ser Arg Asp Thr Ser Lys Asn Gln Leu
65                  70                  75                  80
Ser Leu Lys Leu Ser Ser Val Thr Ala Ala Asp Thr Ala Val Tyr Tyr
                85                  90                  95
Cys Ala Arg Gly Gly Gly Arg Asp Tyr Tyr Gly Met Asp Tyr Trp Gly
            100                 105                 110
Gln Gly Thr Thr Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
```

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 54
<211> LENGTH: 218
<212> TYPE: PRT
<213> ORGANISM: Artificial sequence
<220> FEATURE:
<223> OTHER INFORMATION: Synthesized

<400> SEQUENCE: 54

Asp Ile Val Met Thr Gln Ser Pro Asp Ser Leu Gly Val Ser Leu Gly
1               5                   10                  15

Glu Arg Ala Thr Ile Asn Cys Arg Ala Ser Gln Ser Val Ser Thr Ser
            20                  25                  30

Ser Tyr Ser Tyr Val His Trp Tyr Gln Gln Lys Pro Gly Gln Pro Pro
        35                  40                  45

Lys Leu Leu Ile Lys Tyr Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Asp Ile Pro Phe Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205
```

Val Thr Lys Ser Phe Asn Arg Gly Glu Cys
    210                 215

<210> SEQ ID NO 55
<211> LENGTH: 275
<212> TYPE: PRT
<213> ORGANISM: Artificial sequence
<220> FEATURE:
<223> OTHER INFORMATION: Synthesized

<400> SEQUENCE: 55

Met Gly Trp Ser Trp Ile Phe Phe Phe Leu Leu Ser Gly Thr Ala Ser
1               5                   10                  15

Val Leu Ser Met His Val Ala Gln Pro Ala Val Val Leu Ala Ser Ser
            20                  25                  30

Arg Gly Ile Ala Ser Phe Val Cys Glu Tyr Ala Ser Pro Gly Lys Tyr
        35                  40                  45

Thr Glu Val Arg Val Thr Val Leu Arg Gln Ala Asp Ser Gln Val Thr
    50                  55                  60

Glu Val Cys Ala Ala Thr Tyr Met Met Gly Asn Glu Leu Thr Phe Leu
65                  70                  75                  80

Asp Asp Ser Ile Cys Thr Gly Thr Ser Ser Gly Asn Gln Val Asn Leu
                85                  90                  95

Thr Ile Gln Gly Leu Arg Ala Met Asp Thr Gly Leu Tyr Ile Cys Lys
            100                 105                 110

Val Glu Leu Met Tyr Pro Pro Pro Tyr Tyr Glu Gly Ile Gly Asn Gly
        115                 120                 125

Thr Gln Ile Tyr Val Ile Asp Pro Glu Pro Cys Pro Asp Ser Asp Ser
    130                 135                 140

Gly Gly Gly Gly Ser Gly Gly Gly Ser Gln Val Gln Leu Gln Glu
145                 150                 155                 160

Ser Gly Pro Gly Leu Val Lys Pro Ser Gln Thr Leu Ser Leu Thr Cys
                165                 170                 175

Thr Val Ser Gly Tyr Ser Ile Thr Asn Asp His Trp Trp Asn Trp
            180                 185                 190

Ile Arg Gln His Pro Gly Lys Gly Leu Glu Trp Met Gly Tyr Ile Asp
        195                 200                 205

Ser Ser Gly Ser Ser Asp Asn Asn Pro Ser Leu Lys Ser Gln Ile Thr
    210                 215                 220

Ile Ser Arg Asp Thr Ser Lys Asn Gln Leu Ser Leu Lys Leu Ser Ser
225                 230                 235                 240

Val Thr Ala Ala Asp Thr Ala Val Tyr Tyr Cys Ala Arg Gly Gly Gly
                245                 250                 255

Arg Asp Tyr Tyr Gly Met Asp Tyr Trp Gly Gln Gly Thr Thr Val Thr
            260                 265                 270

Val Ser Ser
        275

<210> SEQ ID NO 56
<211> LENGTH: 586
<212> TYPE: PRT
<213> ORGANISM: Artificial sequence
<220> FEATURE:
<223> OTHER INFORMATION: Synthesized

<400> SEQUENCE: 56

Met His Val Ala Gln Pro Ala Val Val Leu Ala Ser Ser Arg Gly Ile
1               5                   10                  15

-continued

```
Ala Ser Phe Val Cys Glu Tyr Ala Ser Pro Gly Lys Tyr Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Glu Gly Ile Gly Asn Gly Thr Gln Ile
                100                 105                 110

Tyr Val Ile Asp Pro Glu Pro Cys Pro Asp Ser Asp Gly Gly Gly
            115                 120                 125

Gly Ser Gly Gly Gly Gly Ser Gln Val Gln Leu Gln Glu Ser Gly Pro
130                 135                 140

Gly Leu Val Lys Pro Ser Gln Thr Leu Ser Leu Thr Cys Thr Val Ser
145                 150                 155                 160

Gly Tyr Ser Ile Thr Asn Asp Asn His Trp Trp Asn Trp Ile Arg Gln
                165                 170                 175

His Pro Gly Lys Gly Leu Glu Trp Met Gly Tyr Ile Asp Ser Ser Gly
                180                 185                 190

Ser Ser Asp Asn Asn Pro Ser Leu Lys Ser Gln Ile Thr Ile Ser Arg
                195                 200                 205

Asp Thr Ser Lys Asn Gln Leu Ser Leu Lys Leu Ser Ser Val Thr Ala
                210                 215                 220

Ala Asp Thr Ala Val Tyr Tyr Cys Ala Arg Gly Gly Gly Arg Asp Tyr
225                 230                 235                 240

Tyr Gly Met Asp Tyr Trp Gly Gln Gly Thr Thr Val Thr Val Ser Ser
                245                 250                 255

Ala Ser Thr Lys Gly Pro Ser Val Phe Pro Leu Ala Pro Ser Ser Lys
                260                 265                 270

Ser Thr Ser Gly Gly Thr Ala Ala Leu Gly Cys Leu Val Lys Asp Tyr
                275                 280                 285

Phe Pro Glu Pro Val Thr Val Ser Trp Asn Ser Gly Ala Leu Thr Ser
290                 295                 300

Gly Val His Thr Phe Pro Ala Val Leu Gln Ser Ser Gly Leu Tyr Ser
305                 310                 315                 320

Leu Ser Ser Val Val Thr Val Pro Ser Ser Ser Leu Gly Thr Gln Thr
                325                 330                 335

Tyr Ile Cys Asn Val Asn His Lys Pro Ser Asn Thr Lys Val Asp Lys
                340                 345                 350

Lys Val Glu Pro Lys Ser Cys Asp Lys Thr His Thr Cys Pro Pro Cys
                355                 360                 365

Pro Ala Pro Glu Leu Leu Gly Gly Pro Ser Val Phe Leu Phe Pro Pro
                370                 375                 380

Lys Pro Lys Asp Thr Leu Met Ile Ser Arg Thr Pro Glu Val Thr Cys
385                 390                 395                 400

Val Val Val Asp Val Ser His Glu Asp Pro Glu Val Lys Phe Asn Trp
                405                 410                 415

Tyr Val Asp Gly Val Glu Val His Asn Ala Lys Thr Lys Pro Arg Glu
                420                 425                 430
```

```
Glu Gln Tyr Asn Ser Thr Tyr Arg Val Val Ser Val Leu Thr Val Leu
            435                 440                 445

His Gln Asp Trp Leu Asn Gly Lys Glu Tyr Lys Cys Lys Val Ser Asn
450                 455                 460

Lys Ala Leu Pro Ala Pro Ile Glu Lys Thr Ile Ser Lys Ala Lys Gly
465                 470                 475                 480

Gln Pro Arg Glu Pro Gln Val Tyr Thr Leu Pro Pro Ser Arg Asp Glu
                485                 490                 495

Leu Thr Lys Asn Gln Val Ser Leu Thr Cys Leu Val Lys Gly Phe Tyr
                500                 505                 510

Pro Ser Asp Ile Ala Val Glu Trp Glu Ser Asn Gly Gln Pro Glu Asn
                515                 520                 525

Asn Tyr Lys Thr Thr Pro Pro Val Leu Asp Ser Asp Gly Ser Phe Phe
                530                 535                 540

Leu Tyr Ser Lys Leu Thr Val Asp Lys Ser Arg Trp Gln Gln Gly Asn
545                 550                 555                 560

Val Phe Ser Cys Ser Val Met His Glu Ala Leu His Asn His Tyr Thr
                565                 570                 575

Gln Lys Ser Leu Ser Leu Ser Pro Gly Lys
                580                 585

<210> SEQ ID NO 57
<211> LENGTH: 581
<212> TYPE: PRT
<213> ORGANISM: Artificial sequence
<220> FEATURE:
<223> OTHER INFORMATION: Synthesized

<400> SEQUENCE: 57

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Asn Asp
            20                  25                  30

Asn His Trp Trp Asn Trp Ile Arg Gln His Pro Gly Lys Gly Leu Glu
        35                  40                  45

Trp Met Gly Tyr Ile Asp Ser Ser Gly Ser Ser Asp Asn Asn Pro Ser
    50                  55                  60

Leu Lys Ser Gln Ile Thr Ile Ser Arg Asp Thr Ser Lys Asn Gln Leu
65                  70                  75                  80

Ser Leu Lys Leu Ser Ser Val Thr Ala Ala Asp Thr Ala Val Tyr Tyr
                85                  90                  95

Cys Ala Arg Gly Gly Gly Arg Asp Tyr Tyr Gly Met Asp Tyr Trp Gly
                100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205
```

```
Lys Pro Ser Asn Thr Lys Val Asp Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Ser Gly Gly Gly Ser Gly Met His Val Ala Gln Pro Ala
    450                 455                 460
Val Val Leu Ala Ser Ser Arg Gly Ile Ala Ser Phe Val Cys Glu Tyr
465                 470                 475                 480
Ala Ser Pro Gly Lys Tyr Thr Glu Val Arg Val Thr Val Leu Arg Gln
                485                 490                 495
Ala Asp Ser Gln Val Thr Glu Val Cys Ala Ala Thr Tyr Met Met Gly
            500                 505                 510
Asn Glu Leu Thr Phe Leu Asp Asp Ser Ile Cys Thr Gly Thr Ser Ser
        515                 520                 525
Gly Asn Gln Val Asn Leu Thr Ile Gln Gly Leu Arg Ala Met Asp Thr
    530                 535                 540
Gly Leu Tyr Ile Cys Lys Val Glu Leu Met Tyr Pro Pro Pro Tyr Tyr
545                 550                 555                 560
Glu Gly Ile Gly Asn Gly Thr Gln Ile Tyr Val Ile Asp Pro Glu Pro
                565                 570                 575
Cys Pro Asp Ser Asp
            580

<210> SEQ ID NO 58
<211> LENGTH: 138
<212> TYPE: PRT
<213> ORGANISM: Artificial sequence
<220> FEATURE:
<223> OTHER INFORMATION: Synthesized
```

<400> SEQUENCE: 58

Met Asp Phe Gly Leu Ile Phe Phe Ile Val Ala Leu Leu Lys Gly Val
1               5                   10                  15

Gln Cys Glu Val Gln Leu Val Glu Ser Gly Gly Gly Leu Val Gln Pro
            20                  25                  30

Gly Gly Ser Leu Arg Leu Ser Cys Ala Ala Ser Gly Phe Asp Phe Ser
        35                  40                  45

Arg Tyr Trp Met Ser Trp Val Arg Gln Ala Pro Gly Lys Gly Leu Glu
    50                  55                  60

Trp Ile Gly Glu Ile Asn Pro Asp Ser Ser Thr Ile Asn Tyr Ala Pro
65                  70                  75                  80

Ser Leu Lys Asp Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg His Asp Tyr Asp Glu Gly Ile Tyr Phe Asp Tyr Trp
        115                 120                 125

Gly Gln Gly Thr Thr Val Thr Val Ser Ser
    130                 135

<210> SEQ ID NO 59
<211> LENGTH: 5
<212> TYPE: PRT
<213> ORGANISM: Artificial sequence
<220> FEATURE:
<223> OTHER INFORMATION: Synthesized

<400> SEQUENCE: 59

Arg Tyr Trp Met Ser
1               5

<210> SEQ ID NO 60
<211> LENGTH: 17
<212> TYPE: PRT
<213> ORGANISM: Artificial sequence
<220> FEATURE:
<223> OTHER INFORMATION: Synthesized

<400> SEQUENCE: 60

Glu Ile Asn Pro Asp Ser Ser Thr Ile Asn Tyr Ala Pro Ser Leu Lys
1               5                   10                  15

Asp

<210> SEQ ID NO 61
<211> LENGTH: 11
<212> TYPE: PRT
<213> ORGANISM: Artificial sequence
<220> FEATURE:
<223> OTHER INFORMATION: Synthesized

<400> SEQUENCE: 61

His Asp Tyr Asp Glu Gly Ile Tyr Phe Asp Tyr
1               5                   10

<210> SEQ ID NO 62
<211> LENGTH: 128
<212> TYPE: PRT
<213> ORGANISM: Artificial sequence
<220> FEATURE:
<223> OTHER INFORMATION: Synthesized

```
<400> SEQUENCE: 62

Met Asp Phe Gln Val Gln Ile Phe Ser Phe Leu Leu Ile Ser Ala Ser
1               5                   10                  15

Val Ile Ile Ser Arg Gly Asp Ile Gln Met Thr Gln Ser Pro Ser Ser
            20                  25                  30

Leu Ser Ala Ser Val Gly Asp Arg Val Thr Ile Thr Cys Ser Ala Ser
        35                  40                  45

Ser Arg Val Ile Tyr Met His Trp Tyr Gln Gln Lys Pro Gly Lys Ala
    50                  55                  60

Pro Lys Arg Trp Ile Tyr Asp Thr Ser Lys Leu Ala Ser Gly Val Pro
65                  70                  75                  80

Ser Arg Phe Ser Gly Ser Gly Ser Gly Thr Glu Phe Thr Leu Thr Ile
                85                  90                  95

Ser Ser Leu Gln Pro Glu Asp Phe Ala Thr Tyr Tyr Cys Gln Gln Trp
            100                 105                 110

Ser Ser Asn Pro Pro Thr Phe Gly Gly Gly Thr Lys Val Glu Ile Lys
        115                 120                 125

<210> SEQ ID NO 63
<211> LENGTH: 10
<212> TYPE: PRT
<213> ORGANISM: Artificial sequence
<220> FEATURE:
<223> OTHER INFORMATION: Synthesized

<400> SEQUENCE: 63

Ser Ala Ser Ser Arg Val Ile Tyr Met His
1               5                   10

<210> SEQ ID NO 64
<211> LENGTH: 7
<212> TYPE: PRT
<213> ORGANISM: Artificial sequence
<220> FEATURE:
<223> OTHER INFORMATION: Synthesized

<400> SEQUENCE: 64

Asp Thr Ser Lys Leu Ala Ser
1               5

<210> SEQ ID NO 65
<211> LENGTH: 9
<212> TYPE: PRT
<213> ORGANISM: Artificial sequence
<220> FEATURE:
<223> OTHER INFORMATION: Synthesized

<400> SEQUENCE: 65

Gln Gln Trp Ser Ser Asn Pro Pro Thr
1               5

<210> SEQ ID NO 66
<211> LENGTH: 450
<212> TYPE: PRT
<213> ORGANISM: Artificial sequence
<220> FEATURE:
<223> OTHER INFORMATION: Synthesized

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
```

```
                20                  25                  30
Trp Met Ser Trp Val Arg Gln Ala Pro Gly Lys Gly Leu Glu Trp Ile
            35                  40                  45
Gly Glu Ile Asn Pro Asp Ser Ser Thr Ile Asn Tyr Ala Pro Ser Leu
50                  55                  60
Lys Asp Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg His Asp Tyr Asp Glu Gly Ile Tyr Phe Asp Tyr Trp Gly Gln
            100                 105                 110
Gly Thr Thr Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
            210                 215                 220
Lys Thr His Thr Cys Pro Pro Cys Pro Ala Pro Glu Ala Ala Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
```

Gly Lys
    450

<210> SEQ ID NO 67
<211> LENGTH: 213
<212> TYPE: PRT
<213> ORGANISM: Artificial sequence
<220> FEATURE:
<223> OTHER INFORMATION: Synthesized

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ile Tyr Met
            20                  25                  30

His Trp Tyr Gln Gln Lys Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Pro Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 68
<211> LENGTH: 120
<212> TYPE: PRT
<213> ORGANISM: Artificial sequence
<220> FEATURE:
<223> OTHER INFORMATION: Synthesized

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Arg Phe Thr Ile Ser Arg Asp Asn Ala Lys Asn Ser Leu Tyr

```
65                  70                  75                  80
Leu Gln Met Asn Ser Leu Arg Ala Glu Asp Thr Ala Val Tyr Tyr Cys
                85                  90                  95

Ala Arg His Asp Tyr Asp Glu Gly Ile Tyr Phe Asp Tyr Trp Gly Gln
            100                 105                 110

Gly Thr Thr Val Thr Val Ser Ser
        115                 120

<210> SEQ ID NO 69
<211> LENGTH: 255
<212> TYPE: PRT
<213> ORGANISM: Artificial sequence
<220> FEATURE:
<223> OTHER INFORMATION: Synthesized

<400> SEQUENCE: 69

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp Ser Gly Gly Gly
        115                 120                 125

Gly Ser Gly Gly Gly Gly Ser Glu Val Gln Leu Val Glu Ser Gly Gly
    130                 135                 140

Gly Leu Val Gln Pro Gly Gly Ser Leu Arg Leu Ser Cys Ala Ala Ser
145                 150                 155                 160

Gly Phe Asp Phe Ser Arg Tyr Trp Met Ser Trp Val Arg Gln Ala Pro
                165                 170                 175

Gly Lys Gly Leu Glu Trp Ile Gly Glu Ile Asn Pro Asp Ser Ser Thr
            180                 185                 190

Ile Asn Tyr Ala Pro Ser Leu Lys Asp Arg Phe Thr Ile Ser Arg Asp
        195                 200                 205

Asn Ala Lys Asn Ser Leu Tyr Leu Gln Met Asn Ser Leu Arg Ala Glu
    210                 215                 220

Asp Thr Ala Val Tyr Tyr Cys Ala Arg His Asp Tyr Asp Glu Gly Ile
225                 230                 235                 240

Tyr Phe Asp Tyr Trp Gly Gln Gly Thr Thr Val Thr Val Ser Ser
                245                 250                 255

<210> SEQ ID NO 70
<211> LENGTH: 585
<212> TYPE: PRT
<213> ORGANISM: Artificial sequence
<220> FEATURE:
<223> OTHER INFORMATION: Synthesized

<400> SEQUENCE: 70
```

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65              70                  75                  80

Gly Leu Arg Ala Met Asp Thr Gly Leu Tyr Ile Cys Lys Val Glu Leu
                85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp Ser Gly Gly Gly
        115                 120                 125

Gly Ser Gly Gly Gly Ser Glu Val Gln Leu Val Glu Ser Gly Gly
130                 135                 140

Gly Leu Val Gln Pro Gly Gly Ser Leu Arg Leu Ser Cys Ala Ala Ser
145                 150                 155                 160

Gly Phe Asp Phe Ser Arg Tyr Trp Met Ser Trp Val Arg Gln Ala Pro
                165                 170                 175

Gly Lys Gly Leu Glu Trp Ile Gly Glu Ile Asn Pro Asp Ser Ser Thr
            180                 185                 190

Ile Asn Tyr Ala Pro Ser Leu Lys Asp Arg Phe Thr Ile Ser Arg Asp
        195                 200                 205

Asn Ala Lys Asn Ser Leu Tyr Leu Gln Met Asn Ser Leu Arg Ala Glu
    210                 215                 220

Asp Thr Ala Val Tyr Tyr Cys Ala Arg His Asp Tyr Asp Glu Gly Ile
225                 230                 235                 240

Tyr Phe Asp Tyr Trp Gly Gln Gly Thr Thr Val Thr Val Ser Ser Ala
                245                 250                 255

Ser Thr Lys Gly Pro Ser Val Phe Pro Leu Ala Pro Ser Ser Lys Ser
            260                 265                 270

Thr Ser Gly Gly Thr Ala Ala Leu Gly Cys Leu Val Lys Asp Tyr Phe
        275                 280                 285

Pro Glu Pro Val Thr Val Ser Trp Asn Ser Gly Ala Leu Thr Ser Gly
    290                 295                 300

Val His Thr Phe Pro Ala Val Leu Gln Ser Ser Gly Leu Tyr Ser Leu
305                 310                 315                 320

Ser Ser Val Val Thr Val Pro Ser Ser Ser Leu Gly Thr Gln Thr Tyr
                325                 330                 335

Ile Cys Asn Val Asn His Lys Pro Ser Asn Thr Lys Val Asp Lys Lys
            340                 345                 350

Val Glu Pro Lys Ser Cys Asp Lys Thr His Thr Cys Pro Pro Cys Pro
        355                 360                 365

Ala Pro Glu Ala Ala Gly Gly Pro Ser Val Phe Leu Phe Pro Pro Lys
    370                 375                 380

Pro Lys Asp Thr Leu Met Ile Ser Arg Thr Pro Glu Val Thr Cys Val
385                 390                 395                 400

Val Val Asp Val Ser His Glu Asp Pro Glu Val Lys Phe Asn Trp Tyr
                405                 410                 415

Val Asp Gly Val Glu Val His Asn Ala Lys Thr Lys Pro Arg Glu Glu
```

```
            420                 425                 430
Gln Tyr Asn Ser Thr Tyr Arg Val Val Ser Val Leu Thr Val Leu His
            435                 440                 445

Gln Asp Trp Leu Asn Gly Lys Glu Tyr Lys Cys Lys Val Ser Asn Lys
            450                 455                 460

Ala Leu Pro Ala Pro Ile Glu Lys Thr Ile Ser Lys Ala Lys Gly Gln
465                 470                 475                 480

Pro Arg Glu Pro Gln Val Tyr Thr Leu Pro Pro Ser Arg Asp Glu Leu
                485                 490                 495

Thr Lys Asn Gln Val Ser Leu Thr Cys Leu Val Lys Gly Phe Tyr Pro
            500                 505                 510

Ser Asp Ile Ala Val Glu Trp Glu Ser Asn Gly Gln Pro Glu Asn Asn
            515                 520                 525

Tyr Lys Thr Thr Pro Pro Val Leu Asp Ser Asp Gly Ser Phe Phe Leu
            530                 535                 540

Tyr Ser Lys Leu Thr Val Asp Lys Ser Arg Trp Gln Gln Gly Asn Val
545                 550                 555                 560

Phe Ser Cys Ser Val Met His Glu Ala Leu His Asn His Tyr Thr Gln
                565                 570                 575

Lys Ser Leu Ser Leu Ser Pro Gly Lys
            580                 585

<210> SEQ ID NO 71
<211> LENGTH: 580
<212> TYPE: PRT
<213> ORGANISM: Artificial sequence
<220> FEATURE:
<223> OTHER INFORMATION: Synthesized

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
                20                  25                  30

Trp Met Ser Trp Val Arg Gln Ala Pro Gly Lys Gly Leu Glu Trp Ile
            35                  40                  45

Gly Glu Ile Asn Pro Asp Ser Ser Thr Ile Asn Tyr Ala Pro Ser Leu
        50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Asp Tyr Asp Glu Gly Ile Tyr Phe Asp Tyr Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
```

-continued

```
            195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Ala Ala Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Ser Gly Gly Gly Ser Gly Met His Val Ala Gln Pro Ala Val
450                 455                 460
Val Leu Ala Ser Ser Arg Gly Ile Ala Ser Phe Val Cys Glu Tyr Ala
465                 470                 475                 480
Ser Pro Gly Lys Tyr Thr Glu Val Arg Val Thr Val Leu Arg Gln Ala
                485                 490                 495
Asp Ser Gln Val Thr Glu Val Cys Ala Ala Thr Tyr Met Met Gly Asn
            500                 505                 510
Glu Leu Thr Phe Leu Asp Asp Ser Ile Cys Thr Gly Thr Ser Ser Gly
        515                 520                 525
Asn Gln Val Asn Leu Thr Ile Gln Gly Leu Arg Ala Met Asp Thr Gly
530                 535                 540
Leu Tyr Ile Cys Lys Val Glu Leu Met Tyr Pro Pro Pro Tyr Tyr Glu
545                 550                 555                 560
Gly Ile Gly Asn Gly Thr Gln Ile Tyr Val Ile Asp Pro Glu Pro Cys
                565                 570                 575
Pro Asp Ser Asp
            580
```

BIFUNCTIONAL MOLECULES FOR TREATMENT OF IMMUNE DISORDERS

CROSS-REFERENCE TO RELATED APPLICATION

The application claims the benefit of U.S. 63/161,713, filed Mar. 16, 2021, incorporated by reference in its entirety for all purposes.

SEQUENCE LISTING

The application includes sequences in a txt filed named 574211SEQLIST of 118 k bytes, created Mar. 1, 2022, incorporated by reference.

BACKGROUND

Antigen-specific immune response is a complex biological process that is controlled by multiple layers of positive and negative regulators. T cells are initially stimulated through the T cell receptor (TCR) by the recognition of their cognate peptide antigen presented by major histocompatibility complex (MHC; also called HLA for human proteins) molecules on antigen-presenting cells (APCs). The initial interaction between TCR and MHC (or HLA) for T cell activation is referred to as Signal 1. Optimal T cell activation requires a second signal provided by costimulatory molecules such as CD28 and ICOS that belong to the CD28 superfamily (Signal 2). The immune system is further regulated positively by other costimulatory molecules such as CD40, OX40, GITR, CD27, HVEM and 4-1BB that belong to the TNF receptor superfamily and negatively regulated by checkpoint molecules such as PD-1, TIGIT, TIM-3, LAG-3, BTLA, VISTA, CD96 and CD112R. These costimulatory and checkpoint molecules are expressed in a cell type- and development stage-dependent manner to delicately control immune responses in the body. For reviews, see Pardoll, Nat. Rev. Cancer, 12:252-264, 2012; Mahoney et al., Nat. Rev. Drug Discov. 14:561-584, 2015; Shin et al., Curr. Opin. Immunol. 33:23-35, 2015; Marquez-Rodas et al. Ann. Transl. Med. 3:267, 2015; Mercier et al., Front. Immunol. 6:418, 2015; Topalian et al., Cancer Cell 27: 450-461, 2015; Baumeister et al., Annu. Rev. Immunol. 34:539-573, 2016; Ward-Kavanagh et al., Immunity 44:1005-1019, 2016; Torphy et al., Int. J. Mol. Sci. 18:2642, 2017.

CTLA-4 (cytotoxic T-lymphocyte-associated protein 4; also called CD152) is a negative regulator of immune responses. CTLA-4 binds to CD80 (also called B7-1) and CD86 (also called B7-2) expressed on the surface of APCs, interferes in the interaction of CD80 and CD86 with CD28 expressed on T cells, and blocks CD28-mediated costimulation of T cells. Abatacept is a recombinant protein comprising an extracellular domain of human CTLA-4 fused to the Fc region of human gamma-1 heavy chain (CTLA4-Ig). Abatacept was approved for marketing in the U.S. for treatment of adult rheumatoid arthritis, polyarticular juvenile idiopathic arthritis, and adult psoriatic arthritis. Belatacept, a successor of abatacept, is also a CTLA4-Ig fusion protein, which carries two amino acid substitutions in the CTLA-4 region, one from an alanine residue to a tyrosine residue at position 29 (A29Y) and another from a leucine residue to a glutamate residue at position 104 (L104E), to enhance the binding to CD80 and CD86 (Larsen et al., Am. J. Transplant. 5:443-453, 2005; Oshima et al., Protein Eng. Des. Sel. 29:159-167, 2016). Belatacept was approved for marketing in the U.S. for prevention of renal allograft rejection. For reviews of abatacept and belatacept, see Moreland et al., Nat. Rev. Drug Disc. 5:185-186, 2006; Esensten et al., Immunity 44:973-988, 2016; Perez et al., Transplantation 102:1440-1452, 2008; Gallo et al., PLoS ONE 15:e0240335, 2020.

A variety of secreted proteins, such as cytokines and chemokines, are additionally involved in regulation of immune responses by promoting activation, differentiation, proliferation, maintenance, and suppression of certain subsets of immune cells. The action of cytokines on T cells is often referred to as Signal 3, which is the third mechanism required for activation, differentiation, and proliferation of T cells (Gutcher et al., J. Clin. Invest. 117:1119-1127, 2007; Curtsinger et al., Curr. Opin. Immunol. 22:333-340, 2010; Hurton et al., Proc. Natl. Acad. Sci. 113:E7788-E7797, 2016).

Interleukin-15 (IL-15) is a proinflammatory cytokine that is required for activation, proliferation, and maintenance of natural killer (NK) cells and CD8+ memory T cells. IL-15 is secreted mainly by APCs and captured at a high affinity by IL-15 receptor alpha subunit (also called CD215) expressed on the surface of the same or nearby cell. The IL-15/CD215 complex on the cell surface is then presented to the IL-15 receptor comprising CD122 (beta chain subunit of IL-2 and IL-15 receptors) and CD132 (common gamma chain) molecules on the surface of another cell and triggers intracellular signal transduction for induction of cellular functions (trans-presentation of IL-15). For reviews, see Waldmann et al., Annu. Rev. Immunol. 17:19-49, 1999; Stonier et al., Immunol. Lett. 127:85-92, 2010; Anthony et al., Research and Reports in Biology, 6:25-37, 2015; Fehniger, J. Immunol. 202:3125-3126, 2019; Yang et al., Cancers 12:3586, 2020.

Recent studies have shown that a variety of autoimmune diseases are caused by self-reacting CD8+ memory T cells, some of them residing in tissues (tissue-resident memory T cells; Topham et al., Front. Immunol. 9: Article 515, 2018). It has been reported that anti-CD122 monoclonal antibodies that block the interaction between IL-15 and CD122 (thus IL-15 receptor) is therapeutically efficacious in mouse models of vitiligo (Richmond et al., Sci. Trans. Med. 10:eaam7710, 2018), alopecia areata (Xing et al., Nat. Med. 20:1043-1049, 2014), type 1 diabetes (Chen et al., Proc. Natl. Acad. Sci. 110:13534-13539, 2013; Yuan et al. JCI Insight 3:e96600, 2018), celiac disease (Yokoyama et al., Proc. Natl. Acad. Sci. 106:15849-15854, 2009), non-alcoholic steatohepatitis (NASH) (Dudek et al., Nature 592:444-449, 2021) and skin allograft rejection (Mathews et al., J. Clin. Invest. 128:4557-4572, 2018). The role of CD8+ memory T cells is also implicated in pathogenesis of multiple sclerosis (Fransen et al., Brain 143:1714-1730, 2020), polymyositis (Kamiya et al., Rheumatol. 59:224-232, 2020), allergic dermatitis (Gadsbøll et al., J. Invest. Dermatol. 140:806-815, 2020), primary biliary cirrhosis (Yang et al., J. Immunol. 186:1259-1267, 2011), Behçet's disease (Yu et al., Clin. Exp. Immunol. 137:437-443, 2004), and ulcerative colitis (Nemeth et al., Cureus 9:e1177, 2017; Boland et al., Sci. Immunol. 5:eabb4432, 2020).

SUMMARY OF THE CLAIMED INVENTION

The invention provides a bifunctional molecule comprising an antibody that binds to CD122 and inhibits its interaction with IL-2 and IL-15, wherein the antibody is linked at an N- or C-terminus to an extracellular domain of CTLA-4.

Optionally the antibody comprises a heavy chain comprising a mature heavy chain variable region linked to a heavy chain constant region linked at its C-terminus to the extracellular domain of CTLA-4, and a light chain comprising a mature light chain variable region linked to a light chain constant region. Optionally, the antibody is linked to the extracellular domain of CTLA-4 via the C-terminus of the heavy chain constant region or the C-terminus of the light chain constant region. Optionally, the antibody is linked to the extracellular domain of CTLA-4 via the N-terminus of the mature heavy chain variable region or the N-terminus of the mature light chain variable region. Optionally, the heavy or light chain is linked to the extracellular domain of CTLA-4 via a polypeptide linker. Optionally, the polypeptide linker comprises the amino acid sequence of SEQ ID NO:11, 36 or 50. Optionally, the bifunctional molecule is in the form of a heterodimer comprising two copies of the heavy chain and two copies of the light chain. Optionally, the antibody comprises three heavy chain CDRs comprising SEQ ID NOS:17-19 respectively and three light chain CDRs comprising SEQ ID NOS:20-22 respectively. Optionally, the antibody comprises a mature heavy chain variable region comprising SEQ ID NO:37 and a light chain variable region comprising SEQ ID NO:40. Optionally, the heavy chain comprises SEQ ID NO: 8 provided the C-terminal lysine can be omitted, and the light chain comprises SEQ ID NO:9. Optionally, the mature heavy chain is linked to the CTLA-4 extracellular domain as a chain comprising SEQ ID NO:13 or 16 and the mature light chain comprises SEQ ID NO:9. Optionally, the mature light chain is linked to the CTLA-4 extracellular domain as a chain comprising SEQ ID NO:34 and the mature heavy chain comprises SEQ ID NO:8 or 33 provided the C-terminal lysine can be omitted. Optionally, the mature heavy chain is linked to the CTLA-4 extracellular domain as a chain comprising SEQ ID NO:39 provided the C-terminal lysine can be omitted, and the mature light chain comprises SEQ ID NO:9. Optionally the mature light chain is linked to the CTLA-4 extracellular domain as a chain comprising SEQ ID NO:42, and the mature heavy chain comprises SEQ ID NO:8 or 33 provided the C-terminal lysine can be omitted.

Optionally, the antibody comprises three heavy chain CDRs comprising SEQ ID NOS:23-25 respectively, and three light chain CDRs comprising SEQ ID NOS:26-28 respectively. Optionally, the antibody comprises a mature heavy chain variable region comprising SEQ ID NO:29 and a mature light chain variable region comprising SEQ ID NO:30. Optionally, the mature heavy chain comprises SEQ ID NO:53 provided the C-terminal lysine can be omitted and the mature light chain comprises SEQ ID NO:54. Optionally, the mature heavy chain is linked to the CTLA-4 extracellular domain as a chain comprising SEQ ID NO:57 and the mature light chain comprises SEQ ID NO:54. Optionally, the mature heavy chain is linked to the CLTA-4 extracellular domain as a chain comprising SEQ ID NO:56 provided the C-terminal lysine can be omitted, and the mature light chain comprises SEQ ID NO:54.

Optionally, the antibody comprises three heavy chain CDRs comprising SEQ ID NOS: 59-61 respectively and three light chain CDRs comprising SEQ ID NOS:63-65 respectively. Optionally, the mature heavy chain variable region comprises SEQ ID NO:58 and the mature light chain variable region comprises SEQ ID NO:62. Optionally, the mature heavy chain comprises SEQ ID NO:66 provided the C-terminal lysine can be omitted, and the mature light chain comprises SEQ ID NO:67. Optionally, the mature heavy chain is linked to the CTLA-4 extracellular domain as a chain comprising SEQ ID NO:71 and the mature light chain comprises SEQ ID NO:67. Optionally, the mature heavy chain is linked to the CTLA-4 extracellular domain as a chain comprising SEQ ID NO:70 provided the C-terminal lysine can be omitted, and the mature light chain comprises SEQ ID NO:67.

Optionally, the antibody has human IgG1 kappa isotype. Optionally, the heavy chain constant region has one or more mutations to reduce effector function. Optionally, the mutations are L234A and L235A. Optionally, the extracellular domain is of a human CTLA-4. Optionally, the extracellular domain of CTLA-4 comprises SEQ ID NO:10. Optionally, the extracellular domain of CTLA-4 comprises SEQ ID NO:14.

The invention further provides a pharmaceutical composition comprising a bifunctional molecule of any preceding claim and a pharmaceutically acceptable carrier.

The invention further provides a method of treating a subject having an immune disorder, comprising administering an effective regime of a bifunctional molecule of any preceding claim to the subject. Optionally, the immune disorder is any of vitiligo, alopecia areata, type 1 diabetes, celiac disease, non-alcoholic steatohepatitis, skin allograft rejection, multiple sclerosis, polymyositis, allergic dermatitis, primary biliary cirrhosis, Behçet's disease, and ulcerative colitis. Optionally, the immune disorder is graft rejection or graft versus host disease. Optionally, the immune disorder is an autoimmune disease.

The invention further provides an antibody against human CD122, wherein the antibody comprises three heavy chain CDRs comprising SEQ ID NOS: 59-61 respectively and three light chain CDRs comprising SEQ ID NOS. 63-65 respectively. Optionally, the antibody comprises a mature heavy chain variable region comprising SEQ ID NO:58 and a mature light chain variable region comprising SEQ ID NO:62. Optionally, the mature heavy chain comprises SEQ ID NO:66 provided the C-terminal lysine can be omitted, and the mature light chain comprises SEQ ID NO:67.

BRIEF DESCRIPTION OF THE FIGURES

FIGS. 6A, B, C: Schematic structures of the expression vectors pHC623 (A), pHC640 (B), and pHC641 (C).

FIGS. 7A, B, C: Schematic structures of bifunctional molecules HuABC2-Ck-CTLA4YE (A), HuABC2-CTLA4YE-VH (B), and HuABC2-CTLA4YE-Vk (C).

FIGS. 8A, B, C: Schematic structures of the expression vectors pFCm553 (A), pFCm554 (B), and pFCm148 (C).

FIGS. 9A, B, C: Flow cytometry analysis of the binding of bifunctional molecules to CHO-K1/CD80 cells (A), CHO-K1/CD86 cells (B), and Ramos cells (C).

FIGS. 13A, B: Flow cytometry analysis of the binding of bifunctional molecules to CHO-K1/CD80 cells (A), and CHO-K1/CD86 cells (B).

DEFINITIONS

Figure 1:
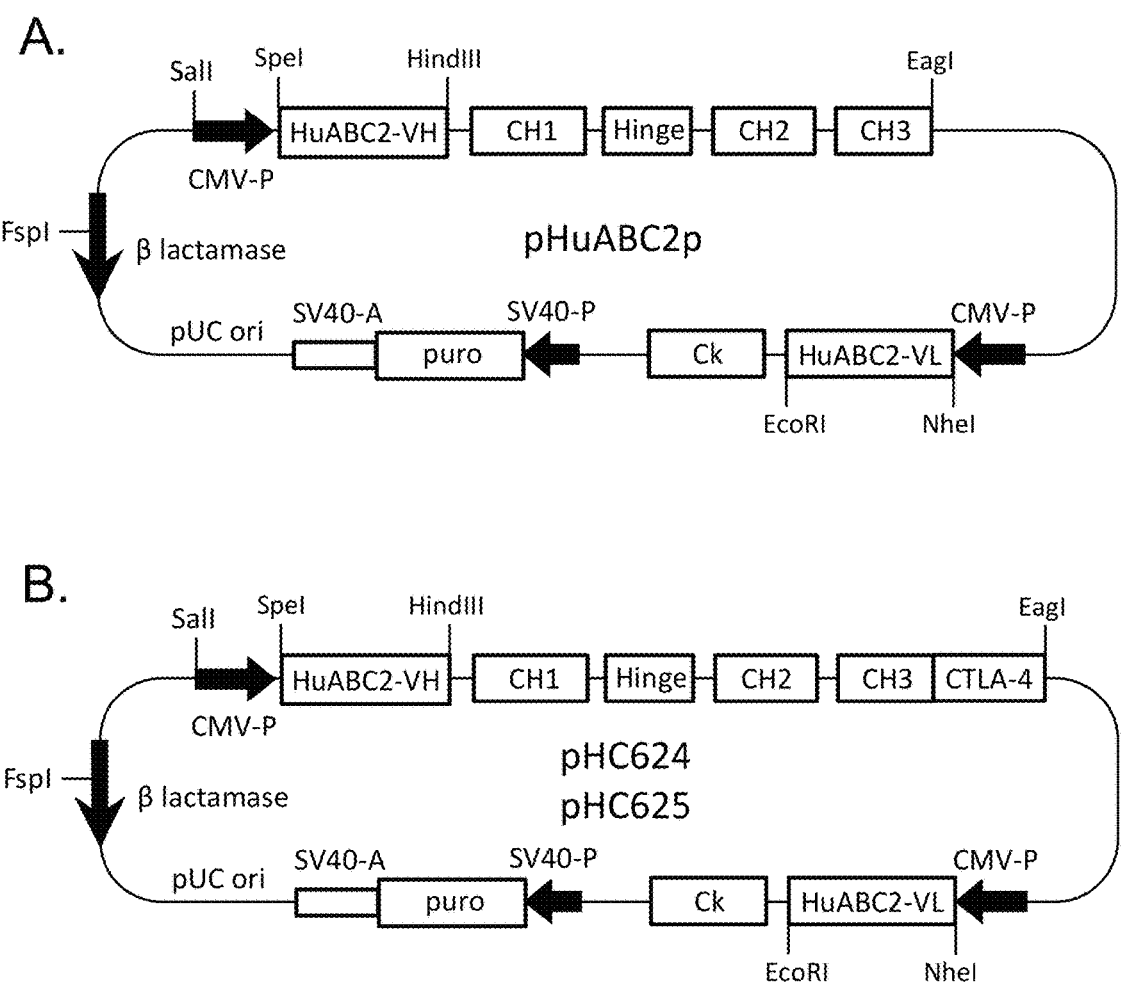
FIGS. 1A, B: Schematic structure of the expression vectors pHuABC2p (A), and pHC624 and pHC625 (B).

Bifunctional molecules or other biological entities are typically provided in isolated form. This means that a biological entity is typically at least 50% w/w pure of interfering proteins and other contaminants arising from its production or purification but does not exclude the possibility that the entity is combined with an excess of pharmaceutically acceptable carrier(s) or other vehicle intended to facilitate its use. Sometimes entities are at least 60, 70, 80, 90, 95 or 99% w/w pure of interfering proteins and contaminants from production or purification. Often an isolated entity the predominant macromolecular species remaining after its purification.

Specific binding of a bifunctional molecule to a target protein, such as CD122, CD80 or CD86 means an affinity of at least $10^6$, $10^7$, $10^8$, $10^9$, or $10^{10}$ M$^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that a molecule binds one and only one target. Bifunctional molecules bind to multiple targets.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. The carboxy-terminal portion of each chain defines a constant region primarily responsible for effector functions.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, Fundamental Immunology (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact antibody has two binding sites, which in a natural antibody are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chain variable regions comprise the domains FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, MD, 1987 and 1991), or Chothia & Lesk, J. Mol. Biol. 196:901-917 (1987); Chothia et al., Nature 342:878-883 (1989). Kabat also provides a widely used numbering convention (Kabat numbering) in which corresponding residues between different heavy chains or between different light chains are assigned the same number.

The term "antibody" includes intact antibodies and binding fragments thereof. Typically, fragments compete with the intact antibody from which they were derived for specific binding to the target including separate heavy chains, light chains Fab, Fab', F(ab')2, F(ab)c, Dabs, nanobodies, and Fv. Fragments can be produced by recombinant DNA techniques, or by enzymatic or chemical separation of intact immunoglobulins.

The term "epitope" refers to a site on an antigen to which an antibody or bifunctional molecule binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., Cancer Res. 50:1495, 1990). A test antibody competes with a reference antibody if an excess of a test antibody (e.g., at least 2×, 5×, 10×, 20× or 100×) inhibits binding of the reference antibody by at least 50% but preferably 75%, 90% or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "subject" includes human and other mammalian subjects that receive either prophylactic or therapeutic treatment. Unless otherwise apparent from the context, it also includes animal models used for testing such treatments.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage. For non-antibody sequences, sequence identity can be determined by aligning sequences using algorithms, such as BESTFIT, FASTA, and TFASTA in the Wisconsin Genetics Software Package Release 7.0, Genetics Computer Group, 575 Science Dr., Madison, Wis.), using default gap parameters, or by inspection, and the best alignment (i.e., resulting in the highest percentage of sequence similarity over a comparison window). Percentage of sequence identity is calculated by comparing two optimally aligned sequences over a window of comparison, determining the number of positions at which the identical residues occurs in both sequences to yield the number of matched positions, dividing the number of matched positions by the total number of matched and mismatched positions not counting gaps in the window of comparison (i.e., the window size), and multiplying the result by 100 to yield the percentage of sequence identity. Unless otherwise indicated the window of comparison between two sequences is defined by the longer of (a) entire length of the shorter of the two sequences being compared, or (b) at least 25 contiguous nucleotides.

When a value is characterized as being within a specified factor of a reference value, the specification should be understood as alternatively disclosing values higher or lower than the reference value within the factor.

Compositions or methods "comprising" one or more recited elements may include other elements not specifically recited. For example, a composition that comprises a bifunctional molecule may contain the bifunctional molecule alone or in combination with other ingredients.

DETAILED DESCRIPTION

I. General

The invention provides bifunctional molecules including an antibody specifically binding to CD122 and an extracellular domain of CTLA-4. The bifunctional molecules specifically bind to CD122 and CTLA-4 ligands, CD80 and CD86 and inhibit their function in immune activation. The bifunctional molecules can inhibit interaction of CD122 with its ligands IL-2 and IL-15 and inhibit interaction of CD80 and CD86 with their counter-receptor, CD28. These bifunctional molecules can suppress Signals 2 and 3 of immune responses as a single therapeutic agent for treatment of immune disorders.

Exemplary anti-CD122 antibodies for inclusion in bifunctional molecules are HuABC2 and HuABC101, which are humanized anti-CD122 IgG1/kappa monoclonal antibodies which bind to CD122 and block the interaction of CD122 with IL-2 and IL-15 (U.S. Pat. No. 9,028,830). Another exemplary anti-CD122 antibody for inclusion in bifunctional molecules is HuABC77, which is a humanized anti-CD122 IgG1/kappa monoclonal antibody which binds to CD122 and blocks the interaction of CD122 with IL-2 and IL-15. The CDRs of HuABC77 are SEQ ID NO:S 59-61 for the heavy chain and SEQ ID NOS: 63-65 for the light chain. HuABC2, which can be regarded as a Signal 3 blocker in the immune system, functions as a suppressor of NK cells and CD8+ memory T cells. HuABC2 was therapeutically efficacious for prevention of renal allograft rejection in non-human primates (Landolfi et al., Abstract No. 185, American Transplant Congress, 2013; Mathews et al. supra).

II. CD122 and Antibodies Thereto

Unless otherwise indicated CD122 means human CD122. An exemplary human CD122 sequence is assigned Swiss Prot accession number P14784. The mature sequence of human CD122 without signal peptide is assigned SEQ ID NO:31. Known natural allelic variants thereof include 10 L V: dbSNP r557770674, 83 S F: dbSNP r52228143, and 391 D E: dbSNP r5228942. The complete human CD122 sequence has 551 amino acids of which amino acids 1-26 are a signal peptide. Approximately residues 27-240 constitute an extracellular domain. Approximately residues 241-265 constitute a transmembrane domain and approximately residues 266-551 constitute a cytoplasmic domain. Antibodies and bifunctional molecules used in the invention bind to epitopes within the extracellular domain of CD122.

CD122 forms receptors in combination with CD132, CD25 and/or IL-15Ra (also called CD215). In brief, the combination of CD122 and CD132 constitutes a receptor with intermediate affinity for IL-2 and IL-15. The combination of CD122, CD132 and CD25 constitutes a receptor with high affinity for IL-2 and the combination of CD122, CD132 and IL-15Ra constitutes a receptor with high affinity for IL-15.

Unless otherwise indicated CD132, CD25 and/or IL-15Ra refer to the human forms of these proteins. An exemplary human sequence for human CD132 is designated Swiss Prot P31785, which is a protein of 369 amino acids of which approximately residues 1-22 are a signal peptide, 23-262 are an extracellular domain, 263-283 are a transmembrane domain and 284-369 are a cytoplasmic domain.

An exemplary human sequence for CD25 is designated Swiss Prot P01589, which is an amino acid sequence of 272 residues of which approximately residues 1-21 are a signal peptide, residues 22-240 are an extracellular domain, residues 241-259 are a transmembrane region and residues 260-272 are a cytoplasmic domain.

An exemplary human sequence for IL-15Ra is designated Swiss Prot Q13261, which is a protein of 267 residues of which approximately 1-30 are a signal peptide, 31-205 are an extracellular domain, 206-228 are a transmembrane region, and 229-267 are a cytoplasmic domain.

Unless otherwise apparent from the context, reference to one of the above receptors means at least the extracellular domain of the protein and usually the complete protein other than a cleavable signal peptide.

The above receptors bind to IL-2 and/or IL-15, the latter of which may be presented in cis or in trans. Unless otherwise apparent from the context, these molecules refer to the human forms of these proteins. An exemplary sequence for human IL-2 is designated Swiss Prot P60568, which is a protein sequence of 153 amino acids of which amino acids 1-20 are a signal peptide. An exemplary sequence for human IL-15 is designated Swiss Prot P40933, which is a protein of 162 amino acids of which amino acids 1-29 are a signal peptide. Unless other apparent from the context, reference to IL-2 or IL-15 means the mature protein from which the signal sequence has been removed.

The invention uses monoclonal antibodies binding to epitopes within the CD122 protein. Antibodies designated ABC2 and ABC101 are two such exemplary mouse antibodies. Both ABC2 and ABC101 specifically bind to human CD122. ABC2 and ABC101 are further characterized by specific binding to cynomolgus CD122 and lack of significant binding to mouse and dog CD122. Binding to CD122 can be demonstrated to CD122 alone and/or any of the receptors incorporating CD122 discussed above. Such monoclonal antibodies are characterized in that as a single agent such a monoclonal antibody has a capacity to substantially inhibit receptors incorporating CD122 from binding to and signaling for cell proliferation in response to both IL-2 and IL-15.

Preferred antibodies and bifunctional molecules incorporating such antibodies inhibit binding of both low and high affinity receptors incorporating CD122 to both IL-2 and IL-15 and can inhibit IL-15 binding both in cis and in trans.

Inhibition may be demonstrated in a binding assay in which a receptor incorporating CD122 is expressed on cells and binds to IL-2 or IL-15 in the presence of an antibody or bifunctional molecule incorporating an antibody being tested. Alternatively, or additionally, inhibition can be demonstrated by expressing a receptor incorporating CD122 on appropriate cells in the presence of IL-2 or IL-15 and assessing an effect of a monoclonal antibody or bifunctional molecule incorporating an antibody on IL-2 or IL-15-mediated proliferation of the cells. Inhibition of IL-15 can be tested in cis or in trans in such formats. Exemplary assay formats for showing inhibition are described in U.S. Pat. No. 9,028,830. Optionally, inhibition of a test antibody or bifunctional molecule can be demonstrated in comparison to an irrelevant control antibody not binding to CD122 or its receptor co-components or to IL-2 and IL-15, or to vehicle lacking any antibody.

Substantial inhibition means an inhibition of at least, 25, 30, 40, 50, or 75%, (e.g., 25-75% or 30-70%) of binding, cell proliferation and/or other functional activity mediated by IL-2 or IL-15. Inhibition is usually demonstrated when the antibody or bifunctional molecule is at no more than 100-fold molar excess (e.g., 2-50 or 2-10 or 2-5 fold molar excess) with respect to the IL-2 or IL-15 ligand. For functional assays, IL-2 or IL-15 is typically present at the minimum level needed to stimulate full functional activity in the absence of antibody or bifunctional molecule under test. Antibodies or bifunctional molecules are usually present at a concentration between 50 nM and 5 µM. Preferred antibodies or bifunctional molecules show inhibition of at least 40% of IL-2 interaction with low or high affinity receptors (or both), and at least 40% for IL-15 presented in cis and in trans. The extent of inhibition can also be quantified by the antibody or bifunctional molecule concentration required for 50% inhibition of proliferation (IC50) mediated by transpresentation of IL-15 to TF-1β cells as described in Examples 2 and 8 of U.S. Pat. No. 9,028,830. An antibody or bifunctional molecule concentration less than 2 µg/ml and preferably less 1 µg/ml, for example about 0.1 to 1 or 0.5 to 1 µg/ml is preferred. Additionally, the antibody or bifunctional molecule concentration required for 50% inhibition of IL-2-mediated TF-1αβ proliferation to cells bearing a high affinity IL-2 receptor as described in Example 8 of U.S. Pat. No. 9,028,830 is preferably less than 100 or 50 µg/ml, for example 10-50 µg/ml.

As is evident from these results the IC50 of an antibody or bifunctional molecule of the invention depends on the nature of the interaction being inhibited. For cells that have the high affinity IL-2 receptor, it is much more difficult for an anti-CD122 antibody or bifunctional molecule to inhibit IL-2 (i.e., higher concentration of the same antibody or bifunctional molecule needed) than to inhibit IL-15 transpresentation. For cells that have only the intermediate affinity IL-2 receptor, it is harder to inhibit (i.e., higher concentration of the same antibody or bifunctional molecule needed) IL-15 trans-presentation than to inhibit soluble IL-2 or IL-15.

Some antibodies bind to the same or overlapping epitope as an antibody designated ABC2 or ABC101. ABC2 and its humanized versions is a monoclonal antibody that binds to CD122 and blocks the interaction of CD122 with IL-2 and IL-15, and functions as an immune suppressor of NK cells and CD8+ memory T cells. ABC2 and its humanized versions can therefore be regarded as a Signal 3 blocker in the immune system.

The sequences of the heavy and light chain CDRs of ABC2 are designated SEQ ID NOS:17-19 and the light chain CDRs as defined by Kabat are designated SEQ ID NOS:20-22. The heavy and light chain CDRs of ABC101 as defined by Kabat are designated SEQ ID NOS:23-25 and 26-28 respectively. Full sequences of mouse and humanized versions are provided in U.S. Pat. No. 9,028,830. Other antibodies having such a binding specificity can be produced by immunizing mice, rats, hamsters, rabbits, or other animal species with CD122 or a portion thereof including the desired epitope, and screening resulting antibodies for binding to CD122, optionally in competition with ABC2 or ABC101. Antibodies identified by such assays can then be screened for ability to inhibit both IL-2 and IL-15 interactions as described in the examples, or otherwise. Antibodies can also be screened against mutagenized forms of the CD122 antigen to identify an antibody showing the same or similar binding profile to collection of mutational changes as ABC2 or ABC101. The mutations can be systematic replacement substitution with alanine (or serine if an alanine is present already) one residue at a time, or more broadly spaced intervals, throughout the extracellular domain of CD122 antibody or through a section thereof in which an epitope is known to reside.

Mutations at residues 42, 43 and 65 of CD122 inhibit specific binding of ABC2 to CD122 (e.g., <10% binding of a positive control anti-FLAG antibody as described as the examples of U.S. Pat. No. 9,028,830). Likewise, mutations at residues 65, 70 and 133 of SEQ ID NO:31 inhibit specific binding of ABC101 to CD122. Because relatively few residues affect binding and the residues are spaced more broadly than a typical linear epitope (e.g., 3-20 contiguous amino acids), these results provide an indication that ABC101 and possibly ABC2 binds to a conformational epitope. Alternatively, one or more of the residues affecting binding may do so allosterically without direct contact with the antibody. The observation that mutagenesis of residue 65 with threonine but not alanine inhibits binding provides an indication that this residue may be affecting binding allosterically. Other antibodies binding to an epitope including one or more of residues 42, 43, 65, 70 and 133 of CD122, and particularly to an epitope including one or more of residues 42, 65 and 133, are likely to share useful inhibitory properties with ABC2 and ABC101. Thus, antibodies whose specific binding is inhibited by mutagenesis of one or more or residues 42, 43 and 65 and particularly residues 42 and 65 of CD122 are likely to share similar properties to ABC2.

Some such antibodies bind to an epitope that includes or consists of residue 42, 43 and/or 65 of CD122. Some such antibodies bind to an epitope that includes or consists of residues 42 and 43 and in which residue 65 affects binding of the antibody allosterically. The epitope can be linear, such as an epitope (e.g., 2-5, 3-5, 3-10, 3-15, 3-20, 5-10, 5-15 or 5-20 contiguous amino acids) including or consisting of 1, 2, or all 3 of the specified amino acids (42, 43 and 65) or be conformational including or consisting of 1, 2, or all 3 of the specified amino acids. Antibodies whose specific binding is inhibited by mutagenesis at 1, 2 or all 3 of residues 65, 70 and 133 of CD122 are likely to show similar inhibitory properties to ABC101. Some such antibodies bind to an epitope that includes or consists of residue 65 or 133 of CD122 or both. Such an epitope can be linear such as an epitope (e.g., 2-5, 3-5, 3-10, 3-15, 3-20, 5-10, 5-15 or 5-20 contiguous amino acids) including or consisting of 1, 2 or all 3 of the specified amino acids (65, 70, and 133) or be conformational including or consisting of 1, 2 or all 3 of the specified amino acids. Some antibodies of the invention specifically bind to CD122 without such binding being substantially inhibited (e.g., binding at least 50% of a positive control antibody as described in the Examples of U.S. Pat. No. 9,028,830) by substitution of residue 39 or 41 of SEQ ID NO:31 with alanine. Any of the above described antibody types includes antibodies that specifically bind to an epitope not including residue 39 or 41 of CD122 or, put another way, whose binding to CD122 is not detectably inhibited by substitution of these residues (binding above 50% of positive control anti-FLAG antibody as described in the examples).

Antibodies binding to an epitope that includes one or more specified residues can be generated by immunizing with a fragment of CD122 that includes these one or more residues. The fragment can for example have no more than 100, 50, 25, 10 or 5 contiguous amino acids from CD122. Such fragments usually have at least 5, 6, 7, 8 or 9 contiguous residues of SEQ ID NO:31. The fragments can be linked to a carrier that helps elicit an antibody response to the fragment and/or be combined with an adjuvant that helps elicit such a response. Alternatively, antibodies binding to a desired residue can be obtained by immunizing with a full-length CD122 (other than signal sequence) or full-length extracellular domain (other than signal sequence) of fibronectin III domain 1 and/or 2. Such antibodies can then be screened for differential binding to hybrids of human and mouse CD122 or differential binding to wildtype CD122 compared with mutants of specified residues. The screen against hybrids of human and mouse CD122 maps antibody binding to certain domains within CD122, such as fibronectin III domain 1 and/or 2. The screen against mutants more precisely defines the binding specificity to allow identification of antibodies whose binding is inhibited by mutagenesis of residues 43, 43, 65, 70 and/or 133 and which are likely to share inhibitor properties of the exemplified antibodies.

Antibodies having the binding specificity of a selected murine antibody (e.g., ABC2 or ABC101) can also be produced using a variant of the phage display method. See Winter, WO 92/20791. This method is particularly suitable for producing human antibodies. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions can for example be obtained from a library of rearranged human heavy chain variable regions. A phage showing strong specific binding for CD122 (e.g., at least $10^8$ and preferably at least $10^9$ $M^{-1}$) is selected. The heavy chain variable region from this phage then serves as a starting material for constructing a further phage library. In this library, each phage displays the same heavy chain variable region (i.e., the region identified from the first display library) and a different light chain variable region. The light chain variable regions can be obtained for example from a library of rearranged human variable light chain regions. Again, phage showing strong specific binding for CD122 are selected. The resulting antibodies usually have the same or similar epitope specificity as the murine starting material.

Other antibodies can be obtained by mutagenesis of cDNA encoding the heavy and light chains of an exemplary antibody, such as ABC2 or ABC101 and their humanized forms. Monoclonal antibodies that are at least 90%, 95% or 99% identical to ABC2 or ABC101 or humanized forms in amino acid sequence of the mature heavy and/or light chain variable regions and maintain its functional properties, and/or which differ from the respective antibody by a small number of functionally inconsequential amino acid substitutions (e.g., conservative substitutions), deletions, or insertions are also included in the invention. Monoclonal antibodies having at least one and preferably all six CDR(s) as defined by Kabat that are 90%, 95%, 99% or 100% identical to corresponding CDRs of ABC2 or ABC101 are also included.

The production of other non-human monoclonal antibodies, e.g., murine, guinea pig, primate, rabbit or rat, against CD122 can be accomplished by, for example, immunizing the animal with CD122 or a fragment thereof, or cells bearing CD122, optionally co-expressed with its co-receptor proteins as discussed above. See Harlow & Lane, *Antibodies, A Laboratory Manual* (CSHP NY, 1988) (incorporated by reference for all purposes). Such an immunogen can be obtained from a natural source, by peptide synthesis or by recombinant expression. Optionally, the immunogen can be administered fused or otherwise complexed with a carrier protein. Optionally, the immunogen can be administered with an adjuvant. Several types of adjuvant can be used as described below. Complete Freund's adjuvant followed by incomplete adjuvant is preferred for immunization of laboratory animals. Rabbits or guinea pigs are typically used for making polyclonal antibodies. Mice are typically used for making monoclonal antibodies. Antibodies are screened for specific binding to CD122. Optionally, antibodies are further screened for binding to a specific region of CD122. Such screening can be accomplished by determining binding of an antibody to a collection of deletion mutants of CD122 and determining which deletion mutants bind to the antibody. Binding can be assessed, for example, by Western blot, FACS or ELISA.

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85, 90, 95 or 100% of corresponding residues defined by Kabat are identical.

Although humanized antibodies often incorporate all six CDRs (preferably as defined by Kabat) from a non-human (e.g., mouse) antibody, they can also be made with less than all CDRs (e.g., at least 3, 4, or 5) CDRs from a non-human antibody (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, J. Mol. Biol. 196:901, 1987), by molecular modeling and/or empirically, or as described in Gonzales et al., Mol. Immunol. 41: 863, 2004. In such humanized antibodies at positions in which one or more donor CDR residues is absent or in which an entire donor CR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

The human acceptor antibody sequences can optionally be selected from among the many known human antibody sequences to provide a high degree of sequence identity (e.g., 65-85% identity) between a human acceptor sequence variable region frameworks and corresponding variable region frameworks of a donor antibody chain.

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a non-human variable region framework residue and a selected human variable region framework residue, the human framework amino acid can be substituted by the equivalent framework amino acid from the non-human antibody when it is reasonably expected that the amino acid:

(1) noncovalently binds antigen directly,
(2) is adjacent to a CDR region,
(3) otherwise interacts with a CDR region (e.g. is within about 6 Å of a CDR region).

Other candidates for substitution are acceptor human framework amino acids that are unusual for a human immunoglobulin at that position. These amino acids can be substituted with amino acids from the equivalent position of the non-human donor antibody or from the equivalent positions of more typical human immunoglobulins. Other candidates for substitution are acceptor human framework amino acids that are unusual for a human immunoglobulin at that position.

An exemplary humanized antibody of the invention is a humanized form of ABC2, characterized by a mature light chain variable region of residues 23 to 128 of SEQ ID NO:2 and a mature heavy chain variable region of residues to 20 to 140 of SEQ ID NO:1 and designated HuABC2. The invention also provides variants of HuABC2. Such variants typically differ from the sequences of HuABC2 by a small number (e.g., typically no more than 1, 2, 3, 5 or 10) of replacements, deletions or insertions. Such differences are usually in the framework but can also occur in the CDRs. For example, only a subset of substitutions at positions H28, H48, H49, H68, H93 and L71 can be made. Many of the framework residues not in contact with the CDRs in the humanized mAb can accommodate substitutions of amino acids from the corresponding positions of the donor mouse mAb or other mouse or human antibodies, and even many potential CDR-contact residues are also amenable to substitution or even amino acids within the CDRs may be altered. One example of a CDR substitution is to substitute a residue in a CDR with the residue occupying the corresponding position of the human acceptor sequence used to supply variable region frameworks.

Often the replacements made in the variant humanized ABC2 sequences are conservative with respect to the replaced HuABC2 amino acids. Preferably, replacements in HuABC2 (whether or not conservative) have no substantial effect on the binding affinity or potency of the humanized mAb, that is, its ability to inhibit interactions between receptors including CD122 and IL-2 and IL-15 (e.g., the potency in some or all of the assays described in the present examples or Background of the variant humanized ABC2 antibody is essentially the same, i.e., within experimental error, as that of HuABC2). Preferably the mature variant light and heavy chain V region sequences are at least 90%, more preferably at least 95%, and most preferably at least 98% identical to the respective HuABC2 mature light and heavy chain V regions. Alternatively, other human antibody acceptor sequences, particularly those with high sequence identity to the variable region framework sequences of ABC2 are also suitable to provide the humanized antibody variable regions framework sequences.

In some variants of HuABC2, at least 1, 2, 3, 4, 5 or all 6 of the positions of acceptor to donor substitutions mentioned in connection with the exemplified antibody (i.e., H28, H48, H49, H68, H93, and L71) are preferably occupied by residues T, I, A, I, A, and Y respectively (the residues occupying the corresponding position of the mouse donor antibody heavy chain). In some variants, position H42 is occupied by a G. If the heavy chain acceptor sequence is other than the sequence encoded by DA430129 cDNA (Gen Bank accession number), or the light chain acceptor sequence is other than the sequence encoded by M29469 cDNA (GenBank accession number), an acceptor to donor substitution may or may not be required for the specified occupancy of a particular variable framework region position depending on whether the residue occupying the specified position is already the same between the acceptor and donor.

Another exemplary humanized antibody of the invention is a humanized form of ABC101, characterized by a mature light chain variable region of SEQ ID NO:30 and a mature heavy chain variable region of SEQ ID NO:29 and designated HuABC101. The invention also provides variants of HuABC101. Such variants typically differ from the sequences of HuABC101 by a small number (e.g., typically no more than 1, 2, 3, 5 or 10) of replacements, deletions or insertions. Such differences are usually in the framework but can also occur in the CDRs. For example, only a subset of substitutions at positions H27, H30, H48, H66, H67, H71 and L49 can be made. Many of the framework residues not in contact with the CDRs in the humanized antibody can accommodate substitutions of amino acids from the corresponding positions of the donor mouse antibody or other mouse or human antibodies, and even many potential CDR-contact residues are also amenable to substitution or even amino acids within the CDRs may be altered. One example of a CDR substitution is to substitute a residue in a CDR with the residue occupying the corresponding position of the human acceptor sequence used to supply variable region frameworks.

Often the replacements made in the variant humanized ABC101 sequences are conservative with respect to the replaced HuABC101 amino acids. Preferably, replacements in HuABC101 (whether or not conservative) have no substantial effect on the binding affinity or potency of the humanized mAb, that is, its ability to inhibit interactions between receptors including CD122 and IL-2 and IL-15 (e.g., the potency in some or all of the assays described herein of the variant humanized ABC101 antibody is essentially the same, i.e., within experimental error, as that of HuABC101). Preferably the mature variant light and heavy chain V region sequences are at least 90%, more preferably at least 95%, and most preferably at least 98% identical to the respective HuABC101 mature light and heavy chain V regions. Alternatively, other human antibody variable region framework acceptor sequences, particularly those with high sequence identity to the variable region framework sequences of ABC101 are also suitable to provide the humanized antibody framework.

In some variants of HuABC101, at least 1, 2, 3, 4, 5, 6 or all 7 of the positions of acceptor to donor substitutions mentioned in connection with the exemplified antibody (i.e., H27, H30, H48, H66, H67, H71 and L49) are preferably occupied by residues Y, T, M, Q, I, R and K respectively (the residues occupying the corresponding position of the mouse donor antibody heavy chain). If the heavy chain acceptor sequence is other than the sequence encoded by DA936142 cDNA (GenBank accession number), or the light chain acceptor sequence is other than the sequence encoded by Z46622 cDNA (GenBank accession number), an acceptor to donor substitution may or may not be required for the specified occupancy of a particular variable framework region position depending on whether the residue occupying the specified position is already the same between the acceptor and donor.

The invention can also use chimeric and veneered forms of non-human antibodies, particularly the ABC2 and ABC101 antibodies of the examples.

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions. Veneered forms of either the ABC2 or ABC101 antibody are included in the invention.

Human antibodies against CD122 are provided by a variety of techniques described below. Some human antibodies are selected by competitive binding experiments, by the phage display method of Winter, above, or otherwise, to have the same epitope specificity as a particular mouse antibody, such as one of the mouse monoclonals described in the examples. Human antibodies can also be screened for a particular epitope specificity by using only a fragment of CD122 as the target antigen, and/or by screening antibodies against a collection of deletion mutants of CD122.

Methods for producing human antibodies include the trioma method of Oestberg et al., *Hybridoma* 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. Nos. 5,877,397, 5,874,299, 5,814,318, 5,789,650, 5,770,429, 5,661,016, 5,633,425, 5,625,126, 5,569,825, 5,545,806, Nature 148, 1547-1553 (1994), *Nature Biotechnology* 14, 826 (1996), Kucherlapati, WO 91/10741 (1991)) and phage display methods (see, e.g., Dower et al., WO 91/17271 and McCafferty et al., WO 92/01047, U.S. Pat. Nos. 5,877,218, 5,871,907, 5,858,657, 5,837,242, 5,733,743 and 5,565,332).

III. Selection of Constant Region

The heavy and light chain variable regions of chimeric, humanized (including veneered), or human antibodies can be linked to at least a portion of a human constant region. The choice of constant region depends, in part, whether antibody-dependent complement and/or cellular mediated cytotoxicity is desired. For example, human isotypes IgG1 and IgG3 have complement-mediated cytotoxicity and human isotypes IgG2 and IgG4 do not. Light chain constant regions can be lambda or kappa. Antibodies can be expressed as tetramers containing two light and two heavy chains, as separate heavy chains, light chains, as Fab, Fab', F(ab')2, and Fv, or as single chain antibodies in which heavy and light chain variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype binds to a non-polymorphic region of a one or more other isotypes. Reference to a human constant region includes a constant region with any natural allotype or any permutation of residues occupying polymorphic positions in natural allotypes.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering) for increasing the half-life of an antibody. Substitution any of positions 234, 235, 236 and/or 237 reduce affinity for Fcγ receptors, particularly FcγRl receptor (see, e.g., U.S. Pat. No. 6,624,821). An exemplary substitution is a double mutation comprising Leu-to-Ala substitutions at positions 234 and 235 (L234A and L235A, respectively) (Hazareh et al., J. Virol. 75: 12161-12168, 2001). Optionally, positions 234, 236 and/or 237 in human IgG2 are substituted with alanine and position 235 with glutamine. (See, e.g., U.S. Pat. No. 5,624,821.)

IV. CTLA-4 Extracellular Domain

CTLA-4 is a negative regulator of immune responses. CTLA-4 specifically binds to CD80 and CD86 expressed on the surface of APCs, inhibits interaction of CD80 and CD86 with CD28 expressed on T cells, and thereby inhibits CD28-mediated co-stimulation of T cells.

An exemplary human form of CTLA-4 has been assigned Swiss Prot P16410. This form has 223 amino acids of which residues 1-35 are a signal peptide, residues 36-161 are an extracellular domain, residues 162-182 are a transmembrane domain and residues 173-223 are a cytoplasmic domain. An exemplary extracellular domain is assigned SEQ ID NO:10 herein, which corresponds to residues 38 to 160 of the Swiss Prot sequence. Reference to the extracellular domain of CTLA-4 includes SEQ ID NO:10 and variants having up to 1, 2, 3, 4, 5, 6, 7, 8, 9 or 10 substitutions, deletions or insertions, and/variants having at least 90, 95, 95 or 99% identity with SEQ ID NO:10. Such variations can be natural or induced, examples of which are provided in the annotation of P16410. Variations can also represent alternative amino acids present in CTLA-4 of other species. CTLA-4 has been subject to systematic mutagenesis to identify substitutions enhancing or inhibiting binding to CD80 and CD86 (Xu et al., J. Immunol. 189:4470-4477, 2012). Examples of high-affinity mutations includes K28H, K28T, A29H, A29T, A29Y, A29W, and T30G. These and other mutations are named by the wild-type amino acid residue on the left, their position in SEQ ID NO:10 in the middle, and an amino acid residue after mutagenesis on the right. Mutations at T at position 51, M at position 53, M at position 54, L at position 58, and L at position 61 also favorably impact binding to one or both ligands. The motif 97MYPPPY102 was intolerant to mutations, especially for interaction with CD80, whereas beneficial mutations that alter the affinity balance for CD80 and CD86 clustered adjacent to this conserved motif (K at position 93, L at position 96, and L at position 104). CTLA-4 mutants with stronger binding to CD80 and CD86 are also reported in Douthwaite et al. (J. Immunol. 198:528-537, 2017) and Oshima et al. (Protein Eng. Des. Sel. 29:159-167, 2016). Preferred variants that enhance binding include A29Y and L104E. These and other mutations are numbered by their position in SEQ ID NO:10 or if present in a sequence with a different number of residues than SEQ ID NO:10, the corresponding position of SEQ ID NO:10 to the position of the mutation in the other sequence when the respective sequences are maximally aligned. Additional flanking amino acids from P16410 may or may not be included at one or both sides of SEQ ID NO:10.

CTLA-4 and its variants show specific binding to CD80 and CD86. An exemplary form of human CD80 also known as B7-1 or BB1 is provided by Swiss-Prot P33681. An exemplary form of human CD86 also known as B7-2 is provided by Swiss-Prot P42081. CD80 and CD86 in turn interact with CD28. An exemplary form of human CD28 is provided by Swiss-Prot P10747.

Belatacept is a recombinant protein comprising the extracellular domain of human CTLA-4 (cytotoxic T-lymphocyte-associated protein 4; also called CD152) fused to the Fc region of human gamma-1 heavy chain (CTLA4-Ig) (SEQ ID NO:49). The CTLA-4 region of belatacept carries two amino acid substitutions, one from an alanine residue to a tyrosine residue at position 29 (A29Y) and another from a leucine residue to a glutamate residue at position 104 (L104E), to enhance the binding to CD80 (also called B7-1) and CD86 (also called B7-2) (Larsen et al., Am. J. Transplant. 5:443-453, 2005; Oshima et al., Protein Eng. Des. Sel. 29:159-167, 2016). Belatacept was approved for marketing in the U.S. for prevention of renal allograft rejection. For reviews of belatacept, see Perez et al., Transplantation 102:1440-1452, 2008; Gallo et al., PLoS ONE 15:e0240335, 2020.

Abatacept, which is a predecessor of belatacept, is also a recombinant protein comprising a wildtype extracellular domain of human CTLA-4 fused to the Fc region of human gamma-1 heavy chain. No amino acid substitutions are introduced in the CTLA-4 region. Abatacept, like belatacept, works as an immune suppresser by blocking the interaction of CD80 and CD86 with CD28. Abatacept was approved for marketing in the U.S. for treatment of adult rheumatoid arthritis, polyarticular juvenile idiopathic arthritis, and adult psoriatic arthritis. For reviews of abatacept, see Moreland et al., Nat. Rev. Drug Disc. 5:185-186, 2006; Esensten et al., Immunity 44:973-988, 2016. Abatacept has been reported effective for inhibiting renal allograft rejection (Badell et al., Am. J. Transplant. 19:2342-2349, 2019). Binding of a CTLA-4 extracellular domain moiety, such as abatacept or belatacept to CD80 and CD86 inhibits immune responses by inhibiting CD28-mediated Signal 2 of the T cell activation pathway.

V. Bifunctional Molecules

Bifunctional molecules of the invention combine an antibody against CD122 as further described above with an extracellular domain of CTLA-4 described above. The extracellular domain of CTLA-4 can be linked to a C-terminus of a heavy chain of the antibody as a fusion protein. Thus, an exemplary bifunctional molecule comprises an antibody heavy chain comprising a mature heavy chain variable region and a heavy chain constant region fused at the C-terminus of the heavy chain constant region to a CTLA-4 extracellular domain plus a light chain comprising a mature light chain variable region and a light chain constant region. An extracellular domain of CTLA-4 can also be linked to a C-terminus of a light chain. Thus, another exemplary bifunctional molecule comprises an antibody heavy chain comprising a mature heavy chain variable region and a heavy chain constant region plus a light chain comprising a mature light chain variable region and a light chain constant region fused at the C-terminus of the light chain constant region to a CTLA-4 extracellular domain. The extracellular domain of CTLA-4 can also be linked to the N-terminus of the heavy or light chain variable region of an antibody. Thus, another exemplary bifunctional molecule comprises an antibody comprising a mature heavy chain variable region and a heavy chain constant region plus a light chain comprising a mature light chain variable region and a light chain constant region linked at the N-terminus of the heavy chain variable region or light chain variable region to the extracellular domain of CTLA-4. Linkage of the heavy or light chain to the CTLA-4 can be direct or indirect, such as via a flexible peptide linker. Flexible peptide linkers can be formed predominantly or exclusively from glycine and serine residues, such as SEQ ID NOS:11, 36 and 50. The heavy and light chains can associate with one another as in a normal antibody. Also two pairs of associated heavy and light chains can dimerize with one another to form a heterodimeric structure analogous to a normal antibody except with a CTLA-4 extracellular domain linked to the N- or C-terminus of the heavy or light chains. The heavy chain constant region can include any or all of the regions present in a normal heavy chain constant region, such as CH1, hinge, CH2 and CH3 optionally with linkage to the extracellular domain of CTLA-4 being through the C-terminus. When the extracellular domain of CTLA-4 is fused to the C-terminus of an antibody heavy chain constant region, the fusion of the CTLA-4 extracellular domain to the C-terminus of a heavy chain constant region is the opposite to that in abatacept or belatacept, where the CTLA-4 extracellular domain is fused to the N-terminus of a heavy chain constant region.

In an exemplary bifunctional molecule based on the HuABC2 antibody, the mature heavy chain is linked to the CTLA-4 extracellular domain as a chain comprising SEQ ID NO:13 or 16 and the mature light chain comprises SEQ ID NO:9. In another such exemplary bifunctional molecule, the mature light chain is linked to the CTLA-4 extracellular domain as a chain comprising SEQ ID NO:34 and the mature heavy chain comprises SEQ ID NO:8 or 33 provided the C-terminal lysine can be omitted. In another such exemplary bifunctional molecule, the mature heavy chain is linked to the CTLA-4 extracellular domain as a chain comprising SEQ ID NO:39 provided the C-terminal lysine can be omitted, and the mature light chain comprises SEQ ID NO:9. In another such exemplary bifunctional molecule, the mature light chain is linked to the CTLA-4 extracellular domain as a chain comprising SEQ ID NO:42, and the mature heavy chain comprises SEQ ID NO:8 or 33 provided the C-terminal lysine can be omitted.

In an exemplary bifunctional molecule based on the HuABC101 antibody, the mature heavy chain is linked to the CTLA-4 extracellular domain as a chain comprising SEQ ID NO:57 and the mature light chain comprises SEQ ID NO:54. In another such exemplary bifunctional molecule, the mature heavy chain is linked to the CLTA-4 extracellular domain as a chain comprising SEQ ID NO:56 provided the C-terminal lysine can be omitted, and the mature light chain comprises SEQ ID NO:54.

In an exemplary bifunctional molecule based on the HuABC77 antibody, the mature heavy chain is linked to the CTLA-4 extracellular domain as a chain comprising SEQ ID NO:71 and the mature light chain comprises SEQ ID NO:67. In another such bifunctional molecule, the mature heavy chain is linked to the CTLA-4 extracellular domain as a chain comprising SEQ ID NO:70 provided the C-terminal lysine can be omitted, and the mature light chain comprises SEQ ID NO:67.

Such bifunctional molecules show specific binding to each of CD122, CD80 and CD86, inhibiting CD122 from interacting with ligands IL-2 and IL-15 and inhibiting CD80 and CD86 from interacting with CD28. Optionally, the binding affinity of a bifunctional molecule for CD122 is the same within experimental error or within a factor of 5, 3, or 2 of that of the anti-CD122 antibody incorporated into a bifunctional molecule. Optionally, the inhibition of CD122 binding to IL-2 or IL-15 by a bifunctional molecule is the same within experimental error or within a factor of 5, 3, or 2 of that of the anti-CD122 antibody incorporated into the bifunctional molecule alone. Optionally, the binding affinity of a bifunctional molecule for CD80 and CD86 is the same within experimental error or within a factor of 5, 3 or 2 of that of an extracellular domain of CTLA-4 incorporated into the bifunctional molecule linked to a heavy chain constant region (as for, example, in abatacept or belatacept). Optionally, the inhibition of CD80 and/or CD86 binding to CD28 by the bifunctional molecule is the same within experimental error or within a factor of 5, 3 or 2 of that of the extracellular domain of CTLA-4 linked to a constant or variable region incorporated into the bifunctional molecule. Optionally, a bifunctional molecule shows greater inhibition of immune response or greater efficacy in treating an immune disorder than either its antibody or extracellular domain components can achieve individually for equimolar doses. Optionally, a bifunctional molecule shows at least additive and preferably a synergistic increase in inhibition or efficacy compared with its antibody or extracellular domain components individually. Optionally a bifunctional molecule shows greater inhibition or efficacy compared with co-administration of its component antibody and extracellular domain in equimolar ratio as separate molecules comparing an equal number of moles of each agent. In comparisons involving an extracellular domain not part of a bifunctional molecule, the extracellular domain can be used alone or fused to an IgG constant region at either its N or C-terminal. Optionally, a bifunctional molecule shows greater inhibition or efficacy compared with co-administration of its component anti-CD122 antibody and either abatacept or belatacept, the comparison being performed with an equimolar amount of each agent.

VI. Expression of Bifunctional Molecules

Bifunctional molecules of the invention are typically produced by recombinant expression using techniques analogous to expression of antibodies. Nucleic acids encoding the heavy chain linked to a CTLA-4 extracellular domain and a light chain or nucleic acids encoding a heavy chain and the light chain linked to a CTLA-4 extracellular domain are expressed to produce the encoded polypeptides, which associate to form a bifunctional molecule. Recombinant nucleic acid constructs typically include an expression control sequence operably linked to coding sequences of these chains, chains, including naturally associated or heterologous promoter regions. Preferably, the expression control sequences are eukaryotic promoter systems in a vector or vectors capable of transforming or transfecting eukaryotic host cells. Once the vector or vectors has been incorporated into the appropriate host, the host is maintained under conditions suitable for high level expression of the nucleotide sequences, and the collection and purification of the bifunctional molecules.

Mammalian cells are a preferred host for expressing nucleotide segments encoding immunoglobulins or fragments thereof. See Winnacker, From Genes to Clones, (VCH Publishers, N Y, 1987). A number of suitable host cell lines capable of secreting intact heterologous proteins have been developed in the art, and include CHO cell lines, various COS cell lines, HeLa cells, HEK293 cells, L cells, and non-antibody-producing myelomas including Sp2/0 and NS0. Preferably, the cells are nonhuman. Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., J. Immunol. 148:1149 (1992).

Once expressed, bifunctional molecules can be purified according to standard procedures of the art, including HPLC purification, column chromatography, gel electrophoresis and the like (see generally, Scopes, Protein Purification (Springer-Verlag, NY, 1982)).

VII. Pharmaceutical Compositions and Methods of Treatment.

Bifunctional molecules can be used for suppressing various undesirable immune response particularly those mediated by any of CD122, CD80 and CD86, and their ligands or receptors, interaction of which is inhibited by the present bifunctional molecules.

One category of immune disorders treatable by bifunctional molecules of the invention is transplant rejection. When allogeneic cells or organs (e.g., skin, kidney, liver, heart, lung, pancreas and bone marrow) are transplanted into a host (i.e., the donor and donee are different individual from the same species), the host immune system is likely to mount an immune response to foreign antigens in the transplant (host-versus-graft disease) leading to destruction of the transplanted tissue. The bifunctional molecules of the present invention are useful, inter alia, to block alloantigen-induced immune responses in the donee.

A related use for bifunctional molecules of the present invention is in modulating the immune response involved in "graft versus host" disease (GVHD). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants.

A further situation in which immune suppression is desirable is in treatment of autoimmune diseases such as type 1 diabetes, Crohn's disease, ulcerative colitis, multiple sclerosis, stiff person syndrome, rheumatoid arthritis, myasthenia gravis, lupus erythematosus, celiac disease, psoriasis, uveitis, alopecia areata, and primary biliary cirrhosis. In these autoimmune diseases, the body develops a cellular and/or humoral immune response against one of its own antigens leading to destruction of that antigen, and potentially crippling and/or fatal consequences. Autoimmune diseases are treated by administering a bifunctional molecule of the invention.

Other autoimmune diseases treatable by the bifunctional molecules of the invention include asthma, allergies, vitiligo, polymyositis, allergic dermatitis, and Behçet's disease. Other autoimmune diseases which can be treated include idiopathic thrombocytopenic purpura, Kawasaki disease, Guillain-Barre syndrome, chronic inflammatory demyelinating systemic lupus erythematosus, autoimmune neutropenia type 1 diabetes, acute disseminated encephalomyelitis, acute motor axonal neuropathy, Addison's disease, adiposis dolorosa, adult-onset Still's disease, ankylosing spondylitis, anti-glomerular basement membrane nephritis, anti-neutrophil cytoplasmic antibody-associated vasculitis, anti-N-methyl-D-aspartate receptor encephalitis, antiphospholipid syndrome, antisynthetase syndrome, aplastic anemia, autoimmune angioedema, autoimmune encephalitis, autoimmune enteropathy, autoimmune hemolytic anemia, autoimmune hepatitis, autoimmune inner ear disease, autoimmune lymphoproliferative syndrome, autoimmune oophoritis, autoimmune orchitis, autoimmune pancreatitis, autoimmune polyendocrine syndrome, autoimmune polyendocrine syndrome type 2, autoimmune polyendocrine syndrome type 3, autoimmune progesterone dermatitis, autoimmune retinopathy, autoimmune thrombocytopenic purpura, autoimmune thyroiditis, autoimmune urticaria, autoimmune uveitis, Balo concentric sclerosis, Behçet's disease, Bickerstaff's encephalitis, bullous pemphigoid, chronic fatigue syndrome, Churg-Strauss syndrome, cicatricial pemphigoid, Cogan syndrome, cold agglutinin disease, complex regional pain syndrome, CREST syndrome, dermatitis herpetiformis, dermatomyositis, discoid lupus erythematosus, endometriosis, enthesitis, enthesitis-related arthritis, eosinophilic esophagitis, eosinophilic fasciitis, epidermolysis bullosa acquisita, erythema nodosum, essential mixed cryoglobulinemia, Evans syndrome, Felty syndrome, fibromyalgia, gastritis, gestational pemphigoid, giant cell arteritis, Goodpasture syndrome, Graves' disease, Graves ophthalmopathy, Hashimoto's encephalopathy, Hashimoto thyroiditis, Henoch-Schonlein purpura, hidradenitis suppurativa, idiopathic dilated cardiomyopathy, idiopathic inflammatory demyelinating diseases, IgA nephropathy, IgG4-related systemic disease, inclusion body myositis, inflammatory bowel disease (IBD), intermediate uveitis, interstitial cystitis, juvenile arthritis, Kawasaki's disease, Lambert-Eaton myasthenic syndrome, leukocytoclastic vasculitis, lichen planus, lichen sclerosus, ligneous conjunctivitis, linear IgA disease, lupus nephritis, lupus vasculitis, Lyme disease, Meniere's disease, microscopic colitis, microscopic polyangiitis, mixed connective tissue disease, Mooren's ulcer, morphea, Mucha-Habermann disease, myocarditis, myositis, neuromyelitis optica, neuromyotonia, opsoclonus myoclonus syndrome, optic neuritis, Ord's thyroiditis, palindromic rheumatism, paraneoplastic cerebellar degeneration, Parry Romberg syndrome, Parsonage-Turner syndrome, pediatric autoimmune neuropsychiatric disorder associated with *Streptococcus*, pemphigus vulgaris, pernicious anemia, *Pityriasis lichenoides* et *Varioliformis acuta*, POEMS syndrome, polyarteritis nodosa, polymyalgia rheumatica, polymyositis, postmyocardial infarction syndrome, postpericardiotomy syndrome, primary biliary cirrhosis, primary immunodeficiency, primary sclerosing cholangitis, progressive inflammatory neuropathy, psoriatic arthritis, pure red cell aplasia, pyoderma gangrenosum, Raynaud's phenomenon, reactive arthritis, relapsing polychondritis, restless leg syndrome, retroperitoneal fibrosis, rheumatic fever, rheumatoid vasculitis, sarcoidosis, Schnitzler syndrome, scleroderma, Sjogren's syndrome, subacute bacterial endocarditis, Susac's syndrome, Sydenham chorea, sympathetic ophthalmia, systemic scleroderma, thrombocytopenia, Tolosa-Hunt syndrome, transverse myelitis, undifferentiated connective tissue disease, urticaria, urticarial vasculitis, and vasculitis.

Although immune disorders can be subdivided into categories as indicated above, the categories are not necessarily mutually exclusive, nor is treatment dependent on the category in which a disorder is placed.

Other disorders treatable by bifunctional molecules of the invention include cancers, particularly hematological malignancies, such as leukemia (e.g., T cell large granular lymphocyte leukemia) or lymphoma. Some such cancers show detectable levels of CD122, CD80 and/or CD86 measured at either the protein (e.g., by immunoassay using one of the exemplified bifunctional molecules) or mRNA level. Some such cancers show elevated levels of CD122, CD80 and/or CD86 relative to noncancerous tissue of the same type, preferably from the same subject. Optionally, a level of CD122, CD80 or CD86 in a cancer is measured before performing treatment.

Bifunctional molecules are administered in an effective regime meaning a dosage, route of administration and frequency of administration that delays the onset, reduces the severity, inhibits further deterioration, and/or ameliorates at least one sign or symptom of a disorder. If a subject is already suffering from a disorder, the regime can be referred to as a therapeutically effective regime. If a subject is at elevated risk of the disorder relative to the general population but is not yet experiencing symptoms, the regime can be referred to as a prophylactically effective regime. In some instances, therapeutic or prophylactic efficacy can be observed in an individual subject relative to historical controls or past experience in the same subject. In other instances, therapeutic or prophylactic efficacy can be demonstrated in a preclinical or clinical trial in a population of treated subjects relative to a control population of untreated subjects.

Exemplary dosage for a bifunctional molecule is 0.1-20 mg/kg, or 0.5-5 mg/kg body weight (e.g., 0.5, 1, 2, 3, 4 or 5 mg/kg) or 10-1500 mg as a fixed dosage. The dosage depends on the condition of the subject and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Administration into the systemic circulation by intravenous or subcutaneous administration is preferred. Intravenous administration can be, for example, by infusion over a period such as 30-90 min.

The frequency of administration depends on the half-life of the bifunctional molecule in the circulation, the condition of the subject and the route of administration among other factors. The frequency can be daily, weekly, monthly, quarterly, or at irregular intervals in response to changes in the subject's condition or progression of the disorder being treated. An exemplary frequency for intravenous administration is between weekly and quarterly over a continuous cause of treatment, although more or less frequent dosing is also possible. For subcutaneous administration, an exemplary dosing frequency is daily to monthly, although more or less frequent dosing is also possible.

The number of dosages administered depends on whether the disorder is acute or chronic and the response of the disorder to the treatment. For acute disorders or acute exacerbations of a chronic disorders between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, a bifunctional molecule can be administered at regular intervals, e.g., weekly, fortnightly, monthly, quarterly, every six months for at least 1, 5 or 10 years, or the life of the subject.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more pharmacologically acceptable carriers, diluents, excipients or auxiliaries. The formulation depends on the route of administration chosen. For injection, bifunctional molecules can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively, bifunctional molecules can be in lyophilized form for constitution with a suitable vehicle, e.g., sterile pyrogen-free water, before use.

Treatment with bifunctional molecules of the invention can be combined with other treatments effective against the disorder being treated. For treatment of immune disorders, conventional treatments include mast cell degranulation inhibitors, corticosteroids, nonsteroidal anti-inflammatory drugs, and stronger anti-inflammatory drugs such as azathioprine, cyclophosphamide, leukeran, FK506 and cyclosporine. Biologic anti-inflammatory agents, such as Tysabri® (natalizumab) or Humira® (adalimumab), can also be used. When used in treating cancer, the bifunctional molecules of the invention can be combined with chemotherapy, radiation, stem cell treatment, surgery or treatment with other biologics such as Herceptin® (trastuzumab) against the HER2 antigen, Avastin® (bevacizumab) against VEGF, or antibodies to the EGF receptor, such as (Erbitux®, cetuximab), and Vectibix® (panitumumab). Chemotherapy agents include chlorambucil, cyclophosphamide or melphalan, carboplatinum, daunorubicin, doxorubicin, idarubicin, and mitoxantrone, methotrexate, fludarabine, and cytarabine, etoposide or topotecan, vincristine and vinblastine.

VIII. Other Applications

The bifunctional molecules can be used for detecting CD122, CD80 and/or CD86 in the context of clinical diagnosis or treatment or in research. For example, the bifunctional molecules can be used to detect presence of CD122, CD80 and/or CD86 on T-cells as an indication a subject is suffering from an immune mediated disorder amenable to treatment. Expression of CD122, CD80 and/or CD86 on a cancer also provides an indication that the cancer is amenable to treatment with the bifunctional molecules of the present invention. The bifunctional molecules can also be sold as research reagents for laboratory research in detecting T-cells and their response to various stimuli. In such uses, bifunctional molecules can be labeled with fluorescent molecules, spin-labeled molecules, enzymes or radioisotopes, and can be provided in the form of kit with all the necessary reagents to perform the assay for CD122, CD80 or CD86. The bifunctional molecules can also be used to purify CD122, CD80 and/or CD86, e.g., by affinity chromatography.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

Example 1: General Methods and Materials

Gene cloning, mutagenesis, plasmid construction, ELISA, and flow cytometry were carried out following standard laboratory techniques such as those described by Green and Sambrook (Molecular Cloning, A Laboratory Manual, 4th ed., 2012, Cold Spring Harbor Laboratory Press, Cold Spring Harbor, NY), Greenfield (Antibodies, A Laboratory Manual, 2nd ed., 2014, Cold Spring Harbor Laboratory Press, Cold Spring Harbor, NY), Kostelny et al. (Int. J. Cancer 93:556-565, 2001), Cole et al. (J. Immunol. 159: 3613-3621, 1997) and Tsurushita et al. (Methods 36:69-83, 2005), and in vendors' protocols.

HuABC2 is a humanized anti-CD122 IgG1/kappa monoclonal antibody that (i) binds to the beta chain subunit of IL-2 and IL-15 receptors (also called CD122) and (ii) blocks the interaction of IL-2 and IL-15 with their respective receptors (U.S. Pat. No. 9,028,830). Amino acid sequence of the heavy chain variable region (VH) of HuABC2 is

```
                                           (SEQ ID NO: 1)
MKLWLNWVFLLTLLHGIQCEVQLVESGGGLVQPGGSLRLSCAASGFTFSD

FYMEWVRQAPGKGLEWIAASRNKANDYTTEYSASVKGRFIVSRDDSKNSL

YLQMNSLKTEDTAVYYCARSYYRYDGMDYWGQGTTVTVSS.
```

The mature HuABC2 VH starts at a glutamate residue of position 20 in SEQ ID NO:1.

Amino acid sequence of the mature light chain variable region (VL) of HuABC2 is

```
                                           (SEQ ID NO: 2)
MDFQVQIFSFLLISASVIVSRGEIVLTQSPATLSLSPGERATLSCSAISS

VSYMYWYQQKPGQAPRLLIYDTSNLVSGVPARFSGSGSGTDYTLTISSLE

PEDFAVYYCQQWNTYPYTFGGGTKVEIK.
```

The mature HuABC2 VL starts at a glutamate residue of position 23 in SEQ ID NO:2.

The schematic structure of the plasmid vector pHuABC2p for production of HuABC2 in mammalian cells is shown in FIG. 1A. Proceeding clockwise from the SalI site in the figure, pHuABC2p contains the heavy chain transcription unit starting with the human cytomegalovirus (CMV) major immediate early promoter and enhancer (CMV-P) to initiate transcription of the antibody heavy chain gene. The CMV promoter is followed by the VH exon encoding HuABC2 VH, a genomic sequence containing the human gamma-1 heavy chain constant region including the CH1, Hinge, CH2 and CH3 exons with the intervening introns, and the polyadenylation site following the CH3 exon. After the heavy chain gene sequence, the light chain transcription unit begins with the CMV promoter, followed by the exon encoding HuABC2 VL and a genomic sequence containing the human kappa chain constant region (Ck) exon with part of the intron preceding it, and the polyadenylation site following the Ck exon. The light chain gene is then followed by the SV40 early promoter (SV40-P), the puromycin N-acetyl-transferase gene (puro) for resistance to puromycin, and a segment containing the SV40 polyadenylation site (SV40-A). Finally, the plasmid contains a part of the plasmid pUC19, comprising the bacterial origin of replication (pUC ori) and beta-lactamase gene (β lactamase). Locations of restriction enzyme sites are shown in the figure. Arrows indicate orientation of transcription.

Amino acid sequences of the CH1, hinge, CH2, and CH3 regions of human gamma-1 heavy chain encoded in pHuABC2p are

```
                                           (SEQ ID NO: 3)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKV, (SEQ ID NO: 4)
EPKSCDKTHTCPPCP, (SEQ ID NO: 5)
APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAK,
and (SEQ ID NO: 6)
GQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKS

LSLSPGK,
``` respectively. Amino acid sequence of the Ck region encoded in pHuABC2p is

```
                                           (SEQ ID NO: 7)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC.
```

Amino acid sequence of mature heavy chain encoded in pHuABC2p is

```
                                           (SEQ ID NO: 8)
EVQLVESGGGLVQPGGSLRLSCAASGFTFSDFYMEWVRQAPGKGLEWIAA

SRNKANDYTTEYSASVKGRFIVSRDDSKNSLYLQMNSLKTEDTAVYYCAR

SYYRYDGMDYWGQGTTVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK
```

-continued
PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

K.

Amino acid sequence of mature light chain encoded in pHuABC2p is (SEQ ID NO: 9)
EIVLTQSPATLSLSPGERATLSCSAISSVSYMYWYQQKPGQAPRLLIYDT

SNLVSGVPARFSGSGSGTDYTLTISSLEPEDFAVYYCQQWNTYPYTFGGG

TKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC.

CHO-K1 cells stably transfected with pHuABC2p (CHO-K1/pHuABC2p) for expression of HuABC2 were grown in SFM4CHO media (HyClone Laboratories, Logan, UT). For purification of HuABC2, culture supernatants of CHO-K1/pHuABC2p cells were loaded onto a protein-A Sepharose® column (HiTrap® MabSelect SuRe™, GE Healthcare, Piscataway, NJ). The column was washed with PBS before HuABC2 was eluted with 0.1 M glycine-HCl buffer (pH 3.0) containing 0.1 M NaCl. After neutralization with 1 M Tris-HCl (pH 8.0), the buffer of eluted antibody was changed to PBS by dialysis. Antibody concentration was determined by measuring absorbance at 280 nm (1.4 OD=1 mg/ml).

Example 2: Bifunctional Molecules Binding to CD80, CD86 and CD122

Binding of CD80 or CD86 on antigen-presenting cells to CD28 on T cells leads to enhancement of the immune responses. CTLA-4 binds to CD80 and CD86 and blocks their interaction with CD28, which results in suppression of T cell activation (Esensten et al., Immunity 44:973-988, 2016).

To equip HuABC2 with the ability to block the function of an immune costimulatory molecule CD28, the CH3 exon in pHuABC2p was modified in such a way to encode the extracellular domain of human CTLA-4 (SEQ ID NO:10) fused at its N-terminal to the penultimate amino acid residue (Gly) of CH3 (CH3-CTLA4 fusion). A flexible polypeptide linker (SGGGGSG; SEQ ID NO:11) was placed between CH3 and CTLA-4 in CH3-CTLA4 fusion. Amino acid sequence of CH3-CTLA4 fusion is (SEQ ID NO: 12)
GQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKS

LSLSPGSGGGGSGMHVAQPAVVLASSRGIASFVCEYASPGKATEVRVTVL

RQADSQVTEVCAATYMMGNELTFLDDSICTGTSSGNQVNLTIQGLRAMDT

GLYICKVELMYPPPYYLGIGNGTQIYVIDPEPCPDSD.

In addition, leucine residues at positions 234 and 235 (EU numbering) in CH2 were both changed to alanine residues to eliminate binding to Fc gamma receptors (Hezareh et al., J. Virol. 75:12161-12168, 2001). The resulting expression vector derived from pHuABC2p was termed pHC624. The schematic structure of pHC624 is shown in FIG. 1B.

Amino acid sequence of the mature heavy chain of HuABC2 fused at the C-terminus to the linker (underlined) followed by the extracellular domain of CTLA-4 encoded in pHC624 is (SEQ ID NO: 13)
EVQLVESGGGLVQPGGSLRLSCAASGFTFSDFYMEWVRQAPGKGLEWIAA

SRNKANDYTTEYSASVKGRFIVSRDDSKNSLYLQMNSLKTEDTAVYYCAR

SYYRYDGMDYWGQGTTVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPEAAGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

SGGGGSGMHVAQPAVVLASSRGIASFVCEYASPGKATEVRVTVLRQADSQ

VTEVCAATYMMGNELTFLDDSICTGTSSGNQVNLTIQGLRAMDTGLYICK

VELMYPPPYYLGIGNGTQIYVIDPEPCPDSD.

Figure 2:
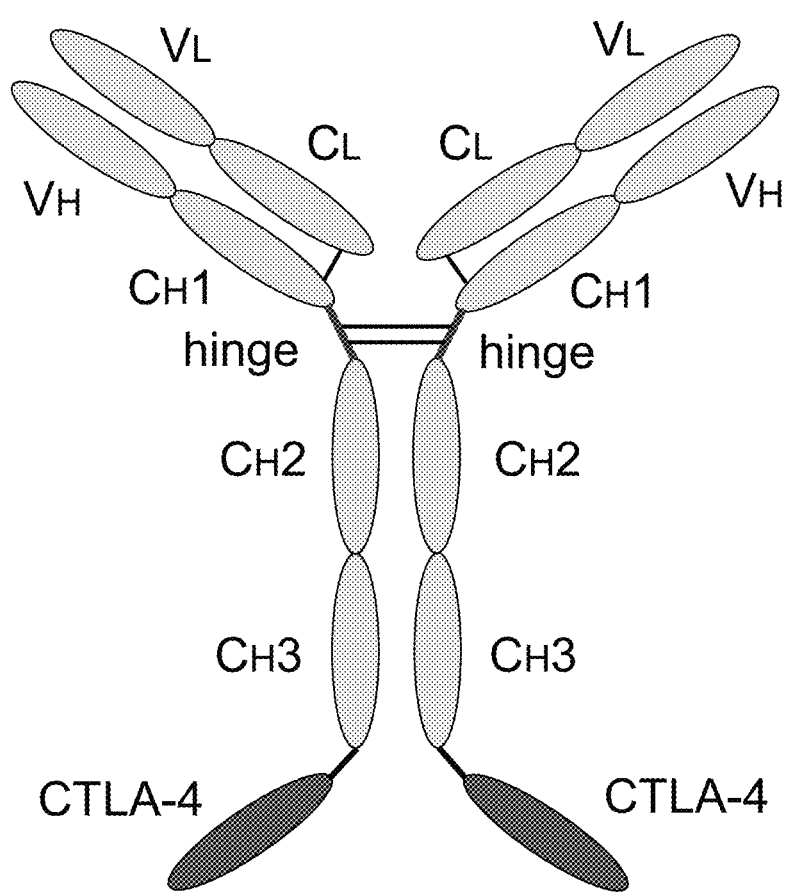
FIG. 2: Schematic structure of bifunctional molecules HuABC2-CTLA4 and HuABC2-CTLA4YE.
Figure 3:
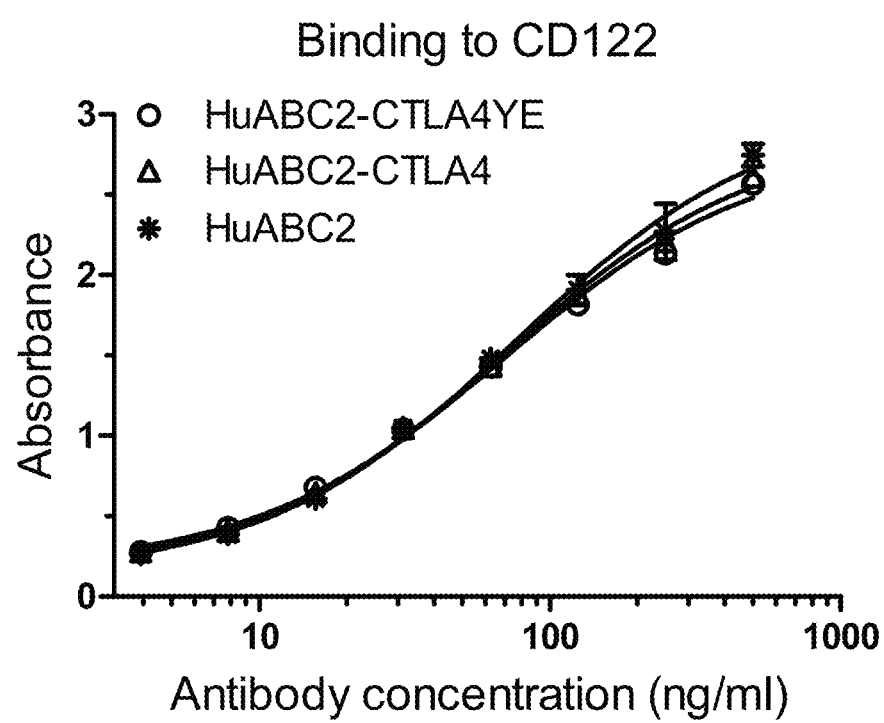
FIG. 3: Binding of HuABC2, HuABC2-CTLA4 and HuABC2-CTLA4YE to CD122. Average absorbance levels of duplicate analysis are shown with standard deviation bars.
Figure 4:
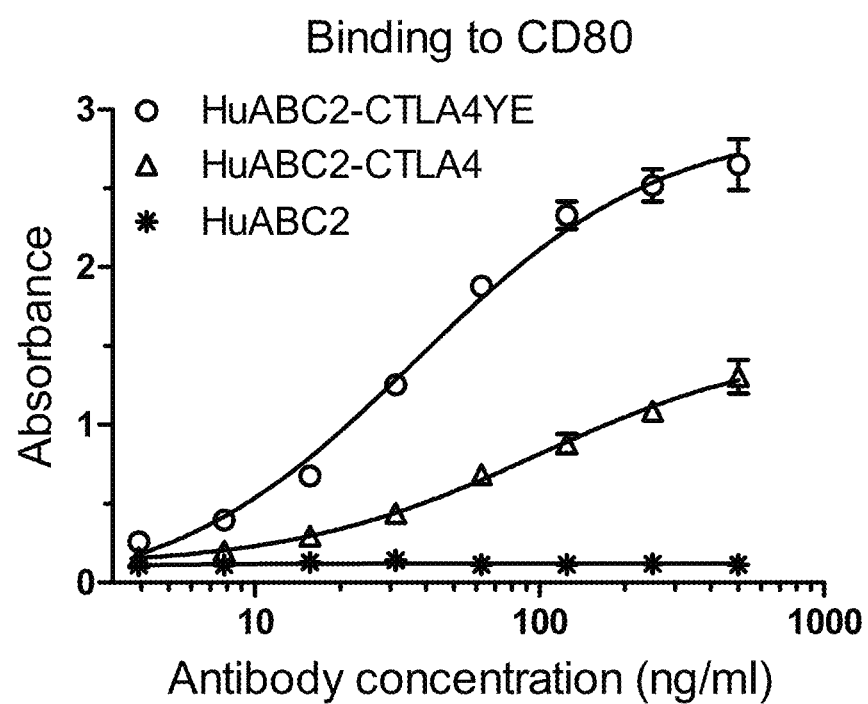
FIG. 4: Binding of HuABC2, HuABC2-CTLA4 and HuABC2-CTLA4YE to CD80. Average absorbance levels of duplicate analysis are shown with standard deviation bars.
Figure 5:
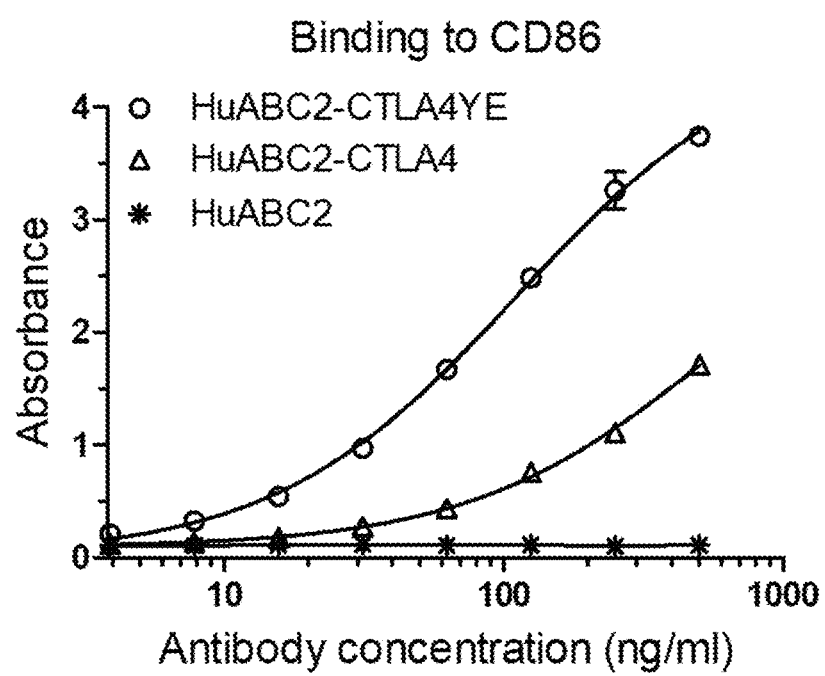
FIG. 5: Binding of HuABC2, HuABC2-CTLA4 and HuABC2-CTLA4YE to CD86. Average absorbance levels of duplicate analysis are shown with standard deviation bars.

Amino acid sequence of mature light chain encoded in pHC624 is same as the mature light chain sequence encoded in pHuABC2p (SEQ ID NO:9). Modified HuABC2 fused to CTLA-4 at the end of the heavy chain, which is encoded by pHC624, was termed HuABC2-CTLA4. The schematic structure of HuABC2-CTLA4 is shown in FIG. 2.

The extracellular domain of CTLA-4 (SEQ ID NO:10) was modified by substitution of two amino acid residues. One of them is a substitution of an alanine residue to a tyrosine reside at position 29 (A29Y) of SEQ ID NO:10. The other is a substitution of a leucine residue to a glutamate residue at position 104 (L104E) of SEQ ID NO:10. Amino acid sequence of the extracellular domain of the resulting modified CTLA-4 (variant CTLA-4) is (SEQ ID NO: 14)
MHVAQPAVVLASSRGIASFVCEYASPGKYTEVRVTVLRQADSQVTEVCAA

TYMMGNELTFLDDSICTGTSSGNQVNLTIQGLRAMDTGLYICKVELMYPP

PYYEGIGNGTQIYVIDPEPCPDSD.

The DNA fragment encoding the variant CTLA-4 was used to replace the region encoding the wild-type CTLA-4 in pHC624. The resulting expression vector was named pHC625 (also called pHC622). The schematic structure of pHC625 is shown in FIG. 16.

Amino acid sequence of the modified CH3-CTLA4 fusion encoded in pHC625 and pHC622 is (SEQ ID NO: 15)
GQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKS

LSLSPGSGGGGSGMHVAQPAVVLASSRGIASFVCEYASPGKYTEVRVTVL

-continued

RQADSQVTEVCAATYMMGNELTFLDDSICTGTSSGNQVNLTIQGLRAMDT

GLYICKVELMYPPPYYEGIGNGTQIYVIDPEPCPDSD.

The linker sequence is underlined.

Amino acid sequence of the mature heavy chain of HuABC2 fused at the C-terminus to the linker (underlined) followed by the extracellular domain of the variant CTLA-4 encoded in pHC625 and pHC622 is (SEQ ID NO: 16)
EVQLVESGGGLVQPGGSLRLSCAASGFTFSDFYMEWVRQAPGKGLEWIAA

SRNKANDYTTEYSASVKGRFIVSRDDSKNSLYLQMNSLKTEDTAVYYCAR

SYYRYDGMDYWGQGTTVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPEAAGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

<u>SGGGGSG</u>MHVAQPAVVLASSRGIASFVCEYASPGKYTEVRVTVLRQADSQ

VTEVCAATYMMGNELTFLDDSICTGTSSGNQVNLTIQGLRAMDTGLYICK

VELMYPPPYYEGIGNGTQIYVIDPEPCPDSD.

Amino acid sequence of mature light chain encoded in pHC625 and pHC622 is same as the mature light chain sequence encoded in pHuABC2p (SEQ ID NO:9). Modified HuABC2 fused to the variant CTLA-4 at the end of the heavy chain, which is encoded in pHC625 and pHC622, was termed HuABC2-CTLA4YE.

Example 3: Transient Expression and Characterization of Bifunctional Molecules Binding to CD80, CD86 and CD122

The expression vectors pHC624 and pHC625 were individually transfected into the human embryonic kidney cell line HEK293 by the procedure of Durocher et al. (Nucl. Acids Res. 30:e9 2002) for secretion of HuABC2-CTLA4 and HuABC2-CTLA4YE, respectively, in culture supernatants. HEK293 cells were grown in DME media containing 10% fetal bovine serum (FBS; HyClone, Logan, UT) at 37° C. in a 7.5% $CO_2$ incubator. Expression level of HuABC2-CTLA4 and HuABC2-CTLA4YE in culture supernatants was measured by sandwich ELISA. In a typical experiment, wells of an ELISA plate were coated with goat anti-human gamma heavy chain polyclonal antibody in PBS, washed with Wash Buffer (PBS containing 0.05% Tween 20), and blocked with Blocking Buffer (PBS containing 2% skim milk and 0.05% Tween 20). After washing the wells with Wash Buffer, test samples appropriately diluted in ELISA Buffer (PBS containing 1% skim milk and 0.025% Tween 20) were applied to the wells. Purified HuABC2 appropriately diluted in ELISA Buffer was used as a standard. After incubation for 1 hr and washing with Wash Buffer, bound antibodies were detected using HRP-conjugated goat anti-human kappa chain polyclonal antibody. After incubation for 30 min and washing with Wash Buffer, color development was initiated by adding ABTS substrate (Sigma-Aldrich, St. Louis, MO) and stopped with 2% oxalic acid. Absorbance was read at 405 nm.

Binding of HuABC2-CTLA4 and HuABC2-CTLA4YE to human CD122, CD80 and CD86 was analyzed by ELISA. Wells of an ELISA plate were coated with 1 μg/ml of either CD122 (Human IL-2R beta/CD122 Protein, Fc Tag; Cat. No. ILB-H5253, Acro Biosystems, Newark, DE), CD80 (Human B7-1/CD80 Protein, Mouse IgG2a Tag; Cat. No. B71-H52A4, Acro Biosystems) or CD86 (Human B7-2/CD86 Protein, Fc Tag; Cat. No. CD6-H5257, Acro Biosystems) in PBS. After blocking with Blocking Buffer and washing the wells with Wash Buffer, transiently expressed HuABC2-CTLA4 and HuABC2-CTLA4YE at 0.5 μg/ml and serial 2-fold dilutions in ELISA Buffer were applied to the wells in duplicates. Purified HuABC2 at 0.5 μg/mland serial 2-fold dilutions was used as a control. After incubation for 1 hr at room temperature and washing with Wash Buffer, bound antibodies were detected using HRP-conjugated goat anti-human kappa chain polyclonal antibody. After incubation for 30 min and washing with Wash Buffer, color development was initiated by adding ABTS substrate and stopped with 2% oxalic acid. Absorbance was read at 405 nm.

FIGS. 3, 4 and 5 show the results of the ELISA experiments for binding of HuABC2, HuABC2-CTLA4 and HuABC2-CTLA4YE to each of human CD122, CD80 and CD86. HuABC2, HuABC2-CTLA4 and HuABC2-CTLA4YE bound to CD122 in a dose-dependent manner (FIG. 3). No significant difference was noticed among their binding patterns to CD122. For CD80, HuABC2 showed only the background level of binding while HuABC2-CTLA4 and HuABC2-CTLA4YE bound to CD80 in a dose-dependent manner (FIG. 4). Similarly, for CD86, HuABC2 showed only the background level of binding while HuABC2-CTLA4 and HuABC2-CTLA4YE bound to CD86 in a dose-dependent manner (FIG. 5). Although both HuABC2-CTLA4 and HuABC2-CTLA4YE gained the ability to bind to CD80 and CD86 in addition to the HuABC2-derived ability to bind to CD122, HuABC2-CTLA4YE showed stronger binding to each of CD80 and CD86 than HuABC2-CTLA4 did (FIGS. 4 and 5).

Example 4: Fusion of CTLA-4 at the C-Terminus of HuABC2 Light Chain

To generate another form of HuABC2 fused to CTLA-4, the Ck exon in pHuABC2p (FIG. 1A) was modified to encode the extracellular domain of the variant form of human CTLA-4 (variant CTLA-4; SEQ ID NO:14) fused at its N-terminus to the last amino acid residue (Cys) of Ck (Ck-CTLA4YE fusion). A flexible polypeptide linker (SGGGGSG; SEQ ID NO:11) was placed between Ck and CTLA-4 in Ck-CTLA4YE fusion. The resulting expression vector derived from pHuABC2p was termed pHC623. Leucine residues at positions 234 and 235 (EU numbering) in CH2 of pHC623 were both changed to alanine residues to eliminate binding to Fc gamma receptors (Hezareh et al., J. Virol. 75:12161-12168, 2001). The schematic structure of pHC623 is shown in FIG. 6A.

Amino acid sequence of the Ck-CTLA4YE fusion encoded in pHC623 is (SEQ ID NO: 32)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC<u>SGGGGS</u>GMHVAQPAVVLASSRGIASFVCEYASPGKYTEVRVTV

LRQADSQVTEVCAATYMMGNELTFLDDSICTGTSSGNQVNLTIQGLRAMD

TGLYICKVELMYPPPYYEGIGNGTQIYVIDPEPCPDSD.

The linker sequence is underlined.

Amino acid sequence of the mature heavy chain encoded in pHC623 is (SEQ ID NO: 33)
EVQLVESGGGLVQPGGSLRLSCAASGFTFSDFYMEWVRQAPGKGLEWIAA

SRNKANDYTTEYSASVKGRFIVSRDDSKNSLYLQMNSLKTEDTAVYYCAR

SYYRYDGMDYWGQGTTVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPEAAGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

K.

Amino acid sequence of the mature light chain of HuABC2 fused at the C-terminus to the linker (underlined) followed by the extracellular domain of the variant CTLA-4 encoded in pHC623 is (SEQ ID NO: 34)
EIVLTQSPATLSLSPGERATLSCSAISSVSYMYWYQQKPGQAPRLLIYDT

SNLVSGVPARFSGSGSGTDYTLTISSLEPEDFAVYYCQQWNTYPYTFGGG

TKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC<u>SGGGGS</u>GMHVAQPAVVLASSRGIASFVCEYASPGKYT

EVRVTVLRQADSQVTEVCAATYMMGNELTFLDDSICTGTSSGNQVNLTIQ

GLRAMDTGLYICKVELMYPPPYYEGIGNGTQIYVIDPEPCPDSD.

Modified HuABC2 fused to the variant CTLA-4 at the end of the light chain, which is encoded in pHC623, was termed HuABC2-Ck-CTLA4YE. The schematic structure of HuABC2-Ck-CTLA4YE is shown in FIG. 7A.

Example 5: Fusion of CTLA-4 at the N-Terminus of HuABC2 Heavy Chain

An alternative form of HuABC2 fused to CTLA-4 was constructed by modifying the VH exon encoding HuABC2 VH in pHuABC2p. The variant CTLA-4 (SEQ ID NO:14) preceded by a synthetic signal peptide (MGWSWIFF-FLLSGTASVLS; SEQ ID NO:35) and followed by a flexible polypeptide linker (SGGGGSGGGGS; SEQ ID NO:36) was fused to the N-terminus of mature HuABC2 VH (SEQ ID NO:37) to generate CTLA-4-HuABC2 VH fusion (CTLA4YE-VH fusion). The amino acid sequence of the CTLA4YE-VH fusion is (SEQ ID NO: 38)
MGWSWIFFFLLSGTASVLSMHVAQPAVVLASSRGIASFVCEYASPGKYTE

VRVTVLRQADSQVTEVCAATYMMGNELTFLDDSICTGTSSGNQVNLTIQG

LRAMDTGLYICKVELMYPPPYYEGIGNGTQIYVIDPEPCPDSD<u>SGGGGSG</u>

<u>GGGS</u>EVQLVESGGGLVQPGGSLRLSCAASGFTFSDFYMEWVRQAPGKGLE

WIAASRNKANDYTTEYSASVKGRFIVSRDDSKNSLYLQMNSLKTEDTAVY

YCARSYYRYDGMDYWGQGTTVTVSS.

The linker sequence is underlined. Mature CTLA4YE-VH fusion starts at position 20 of SEQ ID NO:38.

The resulting expression vector derived from pHuABC2p was termed pHC640. Leucine residues at positions 234 and 235 (EU numbering) in CH2 of pHC640 are both changed to alanine residues to eliminate binding to Fc gamma receptors. The schematic structure of pHC640 is shown in FIG. 6B.

Amino acid sequence of the mature heavy chain of HuABC2 fused at the N-terminus to the extracellular domain of the variant CTLA-4 followed by the linker (underlined) encoded in pHC640 is (SEQ ID NO: 39)
MHVAQPAVVLASSRGIASFVCEYASPGKYTEVRVTVLRQADSQVTEVCAA

TYMMGNELTFLDDSICTGTSSGNQVNLTIQGLRAMDTGLYICKVELMYPP

PYYEGIGNGTQIYVIDPEPCPDSD<u>SGGGGSGGGGS</u>EVQLVESGGGLVQPG

GSLRLSCAASGFTFSDFYMEWVRQAPGKGLEWIAASRNKANDYTTEYSAS

VKGRFIVSRDDSKNSLYLQMNSLKTEDTAVYYCARSYYRYDGMDYWGQGT

TVTVSSASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKV

DKKVEPKSCDKTHTCPPCPAPEAAGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRDELTKN

QVSLTCLVKGFYPSDIAVEWESNGQPENNYKTTPPVLDSDGSFFLYSKLT

VDKSRWQQGNVFSCSVMHEALHNHYTQKSLSLSPGK.

Amino acid sequence of the mature light chain encoded in pHC640 is same as the mature light chain sequence encoded in pHuABC2p (SEQ ID NO:9).

Modified HuABC2 fused to the variant CTLA-4 at the N-terminus of mature heavy chain, which is encoded in pHC640, was termed HuABC2-CTLA4YE-VH. The schematic structure of HuABC2-CTLA4YE-VH is shown in FIG. 7B.

Example 6: Fusion of CTLA-4 at the N-Terminus of HuABC2 Light Chain

An additional form of HuABC2 fused to CTLA-4 was constructed by modifying the Vk exon encoding HuABC2 VL in pHuABC2p. The variant CTLA-4 (SEQ ID NO:14) preceded by a synthetic signal peptide (SEQ ID NO:35) and followed by a flexible polypeptide linker (SGGGGSGGGGS; SEQ ID NO:36) was fused to the N-terminus of mature HuABC2 VL (SEQ ID NO:40) to generate CTLA-4-HuABC2 VL fusion (CTLA4YE-Vk fusion). The amino acid sequence of the CTLA4YE-Vk fusion is (SEQ ID NO: 41)
MGWSWIFFFLLSGTASVLSMHVAQPAVVLASSRGIASFVCEYASPGKYTE

VRVTVLRQADSQVTEVCAATYMMGNELTFLDDSICTGTSSGNQVNLTIQG

LRAMDTGLYICKVELMYPPPYYEGIGNGTQIYVIDPEPCPDSDSGGGGSG

GGGSEIVLTQSPATLSLSPGERATLSCSAISSVSYMYWYQQKPGQAPRLL

IYDTSNLVSGVPARFSGSGSGTDYTLTISSLEPEDFAVYYCQQWNTYPYT

FGGGTKVEIK.

The linker sequence is underlined. Mature CTLA4YE-Vk fusion starts at position 20 of SEQ ID NO:41.

The resulting expression vector derived from pHuABC2p was termed pHC641. Leucine residues at positions 234 and 235 (EU numbering) in CH2 of pHC641 are both changed to alanine residues to eliminate binding to Fc gamma receptors. The schematic structure of pHC641 is shown in FIG. 6C.

Amino acid sequence of mature heavy chain encoded in pHC641 is same as the mature heavy chain sequence encoded in pHC623 (SEQ ID NO:33)

Amino acid sequence of the mature light chain of HuABC2 fused at the N-terminus to the extracellular domain of the variant CTLA-4 followed by the linker (underlined) encoded in pHC641 is (SEQ ID NO: 42)
MHVAQPAVVLASSRGIASFVCEYASPGKYTEVRVTVLRQADSQVTEVCAA

TYMMGNELTFLDDSICTGTSSGNQVNLTIQGLRAMDTGLYICKVELMYPP

PYYEGIGNGTQIYVIDPEPCPDSDSGGGGSGGGGSEIVLTQSPATLSLSP

GERATLSCSAISSVSYMYWYQQKPGQAPRLLIYDTSNLVSGVPARFSGSG

SGTDYTLTISSLEPEDFAVYYCQQWNTYPYTFGGGTKVEIKRTVAAPSVF

IFPPSDEQLKSGTASVVCLLNNFYPREAKVQWKVDNALQSGNSQESVTEQ

DSKDSTYSLSSTLTLSKADYEKHKVYACEVTHQGLSSPVTKSFNRGEC.

Modified HuABC2 fused to the variant CTLA-4 at the N-terminus of mature light chain, which is encoded in pHC641, was termed HuABC2-CTLA4YE-Vk. The schematic structure of HuABC2-CTLA4YE-Vk is shown in FIG. 7C.

Example 7: Expression and Purification of HuABC2 Fused to CTLA-4

CHO-K1 stable transfectants with each of the five expression vectors (pHuABC2p, pHC622, pHC623, pHC640 and pHC641) were generated as described above. Antibody expression in culture supernatants was analyzed by sandwich ELISA as described above. CHO-K1 stable transfectants producing high level of each of HuABC2, HuABC2-CTLA4YE (also called HuABC2-CH3-CTLA4YE), HuABC2-Ck-CTLA4YE, HuABC2-CTLA4YE-VH and HuABC2-CTLA4YE-Vk antibodies were expanded in SFM4CHO. HuABC2 and its CTLA-4 fusions were purified from culture supernatants by protein A column chromatography as described above.

Purified HuABC2, HuABC2-CH3-CTLA4YE, HuABC2-Ck-CTLA4YE, HuABC2-CTLA4YE-VH and HuABC2-CTLA4YE-Vk were characterized by SDS-PAGE under reducing conditions according to standard procedures. Each of these antibodies was found to be composed of two major polypeptides. Their approximate sizes were 50 kD and 25 kD for HuABC2, 65 kD and 25 kD for HuABC2-CH3-CTLA4YE, 50 kD and 40 kD for HuABC2-Ck-CTLA4YE, 65 kD and 25 kD for HuABC2-CTLA4YE-VH, and 50 kD and 40 kD for HuABC2-CTLA4YE-Vk.

Example 8: Binding of HuABC2 Fused to CTLA-4 to CD80, CD86 and CD122

To analyze the property of HuABC2-CH3-CTLA4YE, HuABC2-Ck-CTLA4YE, HuABC2-CTLA4YE-VH and HuABC2-CTLA4YE-Vk, two expression vectors (pFCm553 and pFCm554) were constructed for expression of recombinant human CD80 and CD86, respectively, on the cell surface.

The expression vector pFCm553 (FIG. 8A) has the same structure as pHuABC2p except that (a) the light chain transcription unit was removed and (b) the SpeI-EagI fragment encoding the heavy chain of HuABC2 was substituted with a DNA fragment encoding a synthetic signal peptide (SEQ ID NO:35) followed by the extra cellular region of human CD80 (SEQ ID NO:43), the FLAG polypeptide (DYKDDDDK; SEQ ID NO:44) and the GPI anchorage signal derived from human CD55 (PNKGSGTTSGT-TRLLSGHTCFTLTGLLGTLVTMGLLT; SEQ ID NO:45) (CD80-FLAG-GPI). The amino acid sequence of mature CD80-FLAG-GPI is (SEQ ID NO: 46)
VIHVTKEVKEVATLSCGHNVSVEELAQTRIYWQKEKKMVLTMMSGDMNIW

PEYKNRTIFDITNNLSIVILALRPSDEGTYECVVLKYEKDAFKREHLAEV

TLSVKADFPTPSISDFEIPTSNIRRIICSTSGGFPEPHLSWLENGEELNA

INTTVSQDPETELYAVSSKLDFNMTTNHSFMCLIKYGHLRVNQTFNWNTT

KQEHFPDNTGGGDYKDDDDKGGGPNKGSGTTSGTTRLLSGHTCFTLTGLL

GTLVTMGLLT.

In another expression vector pFCm554 (FIG. 8B), the CD80-coding region in pFCm553 is replaced by the coding region of the extracellular domain of human CD86 (SEQ ID NO:47) to express human CD86 fused to the FLAG peptide and GPI anchorage signal (CD86-FLAG-GPI). The amino acid sequence of mature CD86-FLAG-GPI is (SEQ ID NO: 48)
LKIQAYFNETADLPCQFANSQNQSLSELVVFWQDQENLVLNEVYLGKEKF

DSVHSKYMGRTSFDSDSVVTLRLHNLQIKDKGLYQCIIHHKKPTGMIRIH

QMNSELSVLANFSQPEIVPISNITENVYINLTCSSIHGYPEPKKMSVLLR

TKNSTIEYDGIMQKSQDNVTELYDVSISLSVSFPDVTSNMTIFCILETDK

TRLLSSPFSIELEDPQPPPDHTGGGDYKDDDDKGGGPNKGSGTTSGTTRL

LSGHTCFTLTGLLGTLVTMGLLT.

CHO-K1 stable transfectants expressing CD80-FLAG-GPI (CHO-K1/CD80) and CD86-FLAG-GPI (CHO-K1/CD86) were generated by electroporation with pFCm553 and pFCm554, respectively, as described above. Binding of HuABC2-CH3-CTLA4YE, HuABC2-Ck-CTLA4YE, HuABC2-CTLA4YE-VH and HuABC2-CTLA4YE-Vk to CHO-K1/CD80 and CHO-K1/CD86 cells was analyzed by flow cytometry. Belatacept (also known as LEA29Y and Nulojix; SEQ ID NO:49), which is a CTLA4-Ig fusion protein carrying a substitution of an alanine residue to a tyrosine residue at position 29 (A29Y) and another substitution of a leucine residue to a glutamate residue at position 104 (L104E) of SEQ ID NO:10 (Larsen et al., Am. J. Transplant. 5:443-453, 2005; Oshima et al., Protein Eng. Des. Sel. 29:159-167, 2016), was purchased from Creative Biomart (Cat. No. THP-0109, Shirley, NY) and used as a reference in the experiments.

Purified test samples (HuABC2-CH3-CTLA4YE, HuABC2-Ck-CTLA4YE, HuABC2-CTLA4YE-VH, and HuABC2-CTLA4YE-Vk) and belatacept, starting at 10 µg/ml and five steps of 4-fold serial dilutions, were incubated with CHO-K1/CD80 or CHO-K1/CD86 cells in FACS Buffer (PBS containing 0.5% BSA and 0.05% sodium azide) for 30 min at 4° C. After washing with FACS Buffer, cells were incubated with PE-labeled goat anti-human IgG antibody (SouthernBiotech, Birmingham, AL) in FACS Buffer for 20 min at 4° C. After washing and suspension in FACS Buffer, stained cells were subjected to flow cytometry.

The binding patterns of HuABC2-CH3-CTLA4YE, HuABC2-Ck-CTLA4YE, HuABC2-CTLA4YE-VH, HuABC2-CTLA4YE-Vk and belatacept to CHO-K1/CD80 cells are shown in FIG. 9A. While the binding of each of HuABC2-CTLA4YE-VH and HuABC2-CTLA4YE-Vk to CD80 was only slightly weaker than the binding of belatacept, the binding of HuABC2-CH3-CTLA4YE and HuABC2-Ck-CTLA4YE was a lot weaker than that of belatacept. For example, the mean channel fluorescence (MCF) values for binding to CHO-K1/CD80 cells at 625 ng/ml were 1,583 for belatacept, 425 for HuABC2-CH3-CTLA4YE, 307 for HuABC2-Ck-CTLA4YE, 1,313 for HuABC2-CTLA4YE-VH and 1,310 for HuABC2-CTLA4YE-Vk. Provided that the molecular weight of belatacept is approximately 90 kilodaltons (kD) according to the package insert of Nulojix (belatacept; Bristol Myers Squibb), which is roughly half of the molecular weight of HuABC2-CTLA4YE-VH and HuABC2-CTLA4YE-Vk (both approximately 180 kD), the binding of HuABC2-CTLA4YE-VH and HuABC2-CTLA4YE-Vk, in which CTLA-4 is fused to the N-terminus of heavy and light chains, respectively, to CD80 was comparable to that of belatacept on a molar basis. In contrast, the binding of HuABC2-CH3-CTLA4YE and HuABC2-Ck-CTLA4YE, in which CTLA-4 was fused to the C-terminus of heavy and light chains, respectively, was unexpectedly much weaker than that of belatacept.

The binding patterns of HuABC2-CH3-CTLA4YE, HuABC2-Ck-CTLA4YE, HuABC2-CTLA4YE-VH, HuABC2-CTLA4YE-Vk and belatacept to CHO-K1/CD86 cells are shown in FIG. 9B. Like the case with CHO-K1/CD80 cells, while the binding of each of HuABC2-CTLA4YE-VH and HuABC2-CTLA4YE-Vk to CD86 was only slightly weaker than the binding of belatacept, the binding of HuABC2-CH3-CTLA4YE and HuABC2-Ck-CTLA4YE was a lot weaker than the binding of belatacept. For example, the MCF values for binding to CHO-K1/CD86 cells at 625 ng/ml were 1,179 for belatacept, 221 for HuABC2-CH3-CTLA4YE, 13 for HuABC2-Ck-CTLA4YE, 1,288 for HuABC2-CTLA4YE-VH and 956 for HuABC2-CTLA4YE-Vk. The binding of HuABC2-CTLA4YE-VH and HuABC2-CTLA4YE-Vk to CD86 was comparable to the binding of belatacept on a molar basis, whereas the binding of HuABC2-CH3-CTLA4YE and HuABC2-Ck-CTLA4YE was again unexpectedly much weaker than that of belatacept.

Binding property of HuABC2-CH3-CTLA4YE, HuABC2-Ck-CTLA4YE, HuABC2-CTLA4YE-VH, HuABC2-CTLA4YE-Vk and belatacept was further examined with human Burkitt's lymphoma cell line Ramos by flow cytometry as described above. The result is shown in FIG. 9C. The MCF values for binding to Ramos cells at 625 ng/ml were 539 for belatacept, 63 for HuABC2-CH3-CTLA4YE, 60 for HuABC2-Ck-CTLA4YE, 611 for HuABC2-CTLA4YE-VH and 715 for HuABC2-CTLA4YE-Vk. As observed with CHO-K1/CD80 and CHO-K1/CD86 cells, the binding of HuABC2-CTLA4YE-VH and HuABC2-CTLA4YE-Vk to Ramos cells was comparable to the binding of belatacept, while the binding of HuABC2-CH3-CTLA4YE and HuABC2-Ck-CTLA4YE was much weaker than that of belatacept.

Example 9: Modification of the Linker Between CH3 and CTLA-4

HuABC2-CH3-CTLA4YE showed weak binding to CD80 and CD86 when compared to belatacept and HuABC2-CTLA4YE-VH (FIGS. 9A and B). To assess the influence of a flexible polypeptide linker between CH3 and CTLA-4 on binding to CD80 and CD86, two new expression vectors were generated by modifying the sequence of the polypeptide linker (SGGGGSG; SEQ ID NO:11) connecting CH3 and CTLA-4 in pHC625 encoding HuABC2-CH3-CTLA4YE. The sequence of the polypeptide linker between CH3 and CTLA-4 in one of the resulting vectors, pHC634, is SGGGGSGGGGS (SEQ ID NO:36). The modified HuABC2-CH3-CTLA4YE expressed from pHC634 was termed HuABC2-CH3-CTLA4YE-X. The sequence of the polypeptide linker between CH3 and CTLA-4 in the other resulting vector, pHC635, is SGGGGSGGGGSGGGGS (SEQ ID NO:50). The modified HuABC2-CH3-CTLA4YE expressed from pHC635 was termed HuABC2-CH3-CTLA4YE-Y.

Each of the three expression vectors (pHC625, pHC634 and pHC635) was transfected into HEK293 cells as described above. The expression level of HuABC2-CH3-CTLA4YE, HuABC2-CH3-CTLA4YE-X and HuABC2-CH3-CTLA4YE-Y in culture supernatants was measured by sandwich ELISA as described above. Binding of HuABC2-CH3-CTLA4YE, HuABC2-CH3-CTLA4YE-X and HuABC2-CH3-CTLA4YE-Y to each of CHO-K1/CD80 and CHO-K1/CD86 cells was analyzed by flow cytometry as described above. HuABC2-CH3-CTLA4YE, HuABC2-CH3-CTLA4YE-X and HuABC2-CH3-CTLA4YE-Y showed no clear difference in binding to CD80 and CD86.

Example 10: Binding to CD122

To assess the possibility that the attachment of CTLA-4 at the N-terminus of heavy or light chain of HuABC2 interferes with its antigen binding, the ability of HuABC2-CTLA4YE-VH and HuABC2-CTLA4YE-Vk to bind to CD122 was compared to that of HuABC2. An expression vector pFCm148 (FIG. 8C) has the same structure as pFCm553 (FIG. 8A) except that the coding regions of CD80 and puromycin N-acetyl-transferase are substituted by the extracellular domain of human CD122 (SEQ ID NO:51) and xanthine-guanine phosphoribosyltransferase (shown as gpt in FIG. 8C), respectively. The amino acid sequence of mature human CD122 fused to the FLAG peptide and GPI anchorage signal (CD122-FLAG-GPI) encoded in pFCm148 is (SEQ ID NO: 52)
AVNGTSQFTCFYNSRANISCVWSQDGALQDTSCQVHAWPDRRRWNQTCEL

LPVSQASWACNLILGAPDSQKLTTVDIVTLRVLCREGVRWRVMAIQDFKP

FENLRLMAPISLQVVHVETHRCNISWEISQASHYFERHLEFEARTLSPGH

TWEEAPLLTLKQKQEWICLETLTPDTQYEFQVRVKPLQGEFTTWSPWSQP

LAFRTKPAALGKDTTGGGDYKDDDDKGGGPNKGSGTTSGTTRLLSGHTCF

TLTGLLGTLVTMGLLT.

A mouse myeloma cell line NS0 was stably transfected by electroporation with pFCm148 and selected for expression of xanthine-guanine phosphoribosyltransferase according to standard procedures. An NS0 stable transfectant expressing CD122-FLAG-GPI on the surface (NS0/CD122) was used for the analysis of binding of HuABC2, HuABC2-CTLA4YE-VH and HuABC2-CTLA4YE-Vk to CD122.

Figure 10:
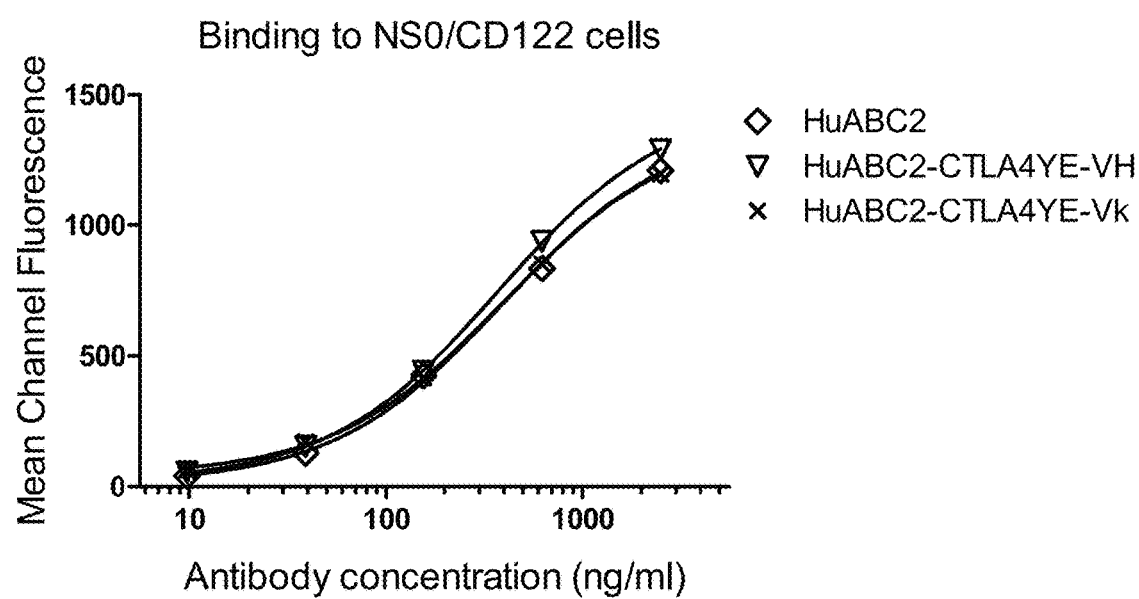
FIG. 10. Flow cytometry analysis of the binding of bifunctional molecules to NS0/CD122 cells

Each of HuABC2, HuABC2-CTLA4YE-VH and HuABC2-CTLA4YE-Vk, starting at 2.5 µg/ml and four steps of 4-fold serial dilutions, was incubated with NS0/CD122 cells in FACS Buffer for 30 min at 4° C. After washing with FACS Buffer, cells were incubated with PE-labeled goat anti-human IgG antibody for 20 min at 4° C. After washing and suspension in FACS Buffer, cells were subjected to flow cytometry. As shown in FIG. 10, HuABC2, HuABC2-CTLA4YE-VH and HuABC2-CTLA4YE-Vk showed no clear difference for binding to CD122. Thus, antigen binding of HuABC2 was not negatively affected by fusion of CTLA-4 to the N-terminus of its heavy or light chain.

Example 11: Immunosuppressive Activity of HuABC2 Fused to CTLA-4

The activity of HuABC2 fused to CTLA-4 to suppress immune responses was examined by a mixed lymphocyte reaction (MLR) using CD3+ T cells and allogenic monocyte-derived dendritic cells (Mo-DCs) (Latek et al., Transplantation, 87: 926-933, 2009; Goenka et al., J. Immunol, 206:1102-1113, 2021). CD3+ T cells were purified from human peripheral blood mononuclear cells (PBMC) using the MojoSort Human CD3 T Cell Isolation Kit (BioLegend, San Diego, CA) and labeled with 2.5 µM CellTrace Far Red (Thermo Fisher Scientific). To generate mature Mo-DCs, CD14+ monocytes were isolated from human PBMC of a different donor using CD14 MicroBeads, human (Miltenyi Biotec, Auburn, CA), cultured in RPMI 1640 medium supplemented with 10% FBS (Life Technologies, Grand Islands, NY), 10 mM HEPES, 1 mM sodium pyruvate, 250 IU/ml human IL-4 (BioLegend) and 800 IU/ml human GM-CSF (BioLegend) for 6 days at 37° C. in a 7.5% $CO_2$ incubator, and further grown for 1 day in RPMI 1640 medium supplemented with 10% FBS, 10 mM HEPES, 1 mM sodium pyruvate, 1,000 IU/ml human IL-6 (BioLegend), 200 IU/ml human IL-1β (BioLegend) and 1,000 IU/ml human TNF-α (BioLegend).

MLR was conducted by mixing CD3+ T cells labeled with CellTrace Far Red and allogeneic mature Mo-DCs at a 2:1 ratio in RPMI 1640 medium supplemented with 10% FBS, 10 mM HEPES, 1 mM sodium pyruvate in the presence or absence of 3 µg/ml of each test sample or their combination. After 6-day incubation at 37° C. in a 7.5% $CO_2$ incubator, cells were stained with Helix NP Green (BioLegend) and subjected to flow cytometry. Fluorescence levels of Helix NP Green and CellTrace Far Red were used to monitor viability and proliferation of cells, respectively. Mo-DCs, which were not stained by CellTrace Far Red and thus negative for its fluorescence, were excluded from the analysis. T cell proliferation was monitored by the level of fluorescence of CellTrace Far Red according to the User Guide of the CellTrace Far Red Cell Proliferation Kit (Thermo Fisher Scientific) and calculated by dividing the number of proliferating T cells by the number of total live T cells.

Figure 11:
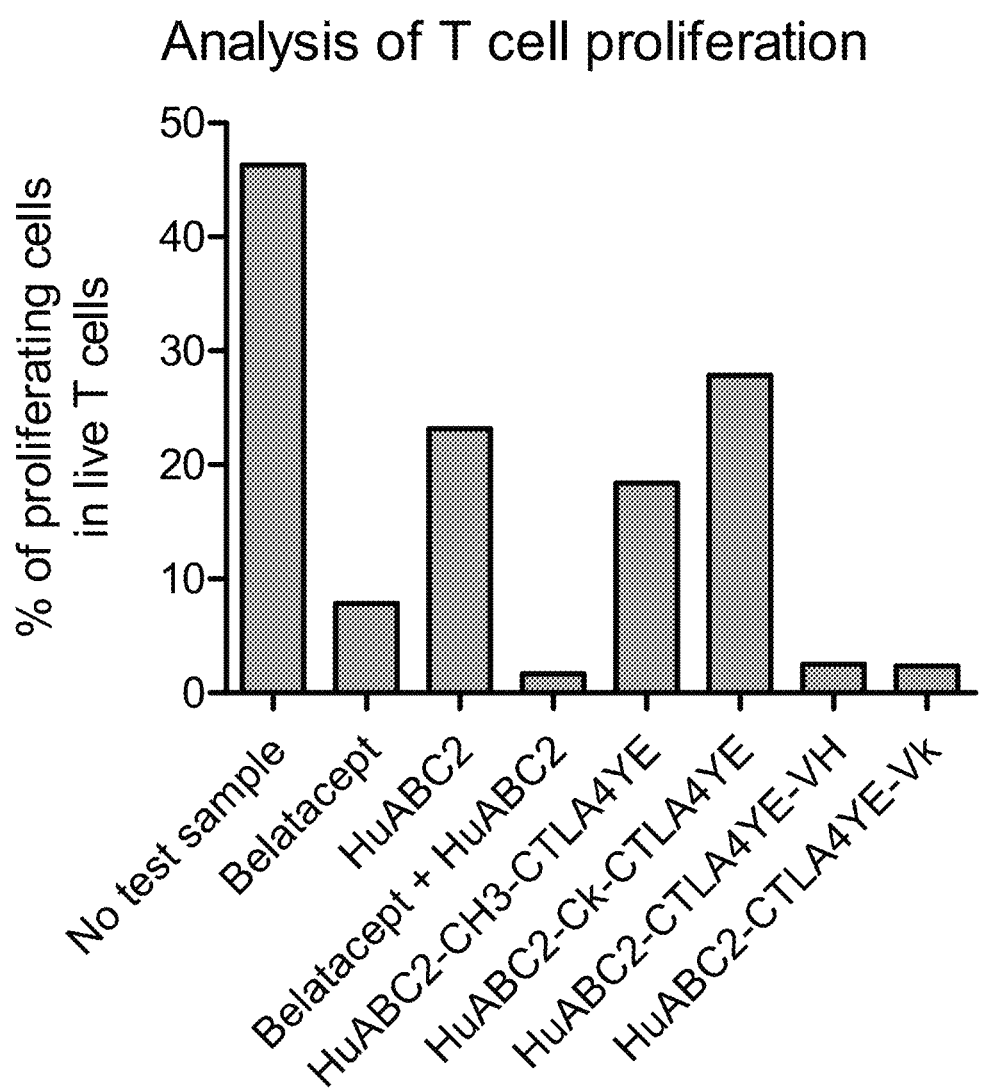
FIG. 11: Proliferation of human T cells in the mixed lymphocyte reaction.

The result of the analysis of T cell proliferation in MLR is shown in FIG. 11. The ratio of proliferating T cells in the live T cell population was 46.3% with no test sample, 7.9% with belatacept, 23.2% with HuABC2, 1.7% with a combination of belatacept and HuABC2, 18.4% with HuABC2-CH3-CTLA4YE, 27.9% with HuABC2-Ck-CTLA4YE, 2.5% with HuABC2-CTLA4YE-VH, and 2.4% with HuABC2-CTLA4-Vk. Both HuABC2-CTLA4YE-VH and HuABC2-CTLA4-Vk suppressed T cell proliferation more potently than each of belatacept and HuABC2, and nearly as efficiently as the combination of HuABC2 and belatacept. The activity of each of HuABC2-CH3-CTLA4YE and HuABC2-Ck-CTLA4YE to suppress T cell proliferation was much weaker than the activity of HuABC2-CTLA4YE-VH and HuABC2-CTLA4-Vk.

Figure 12:
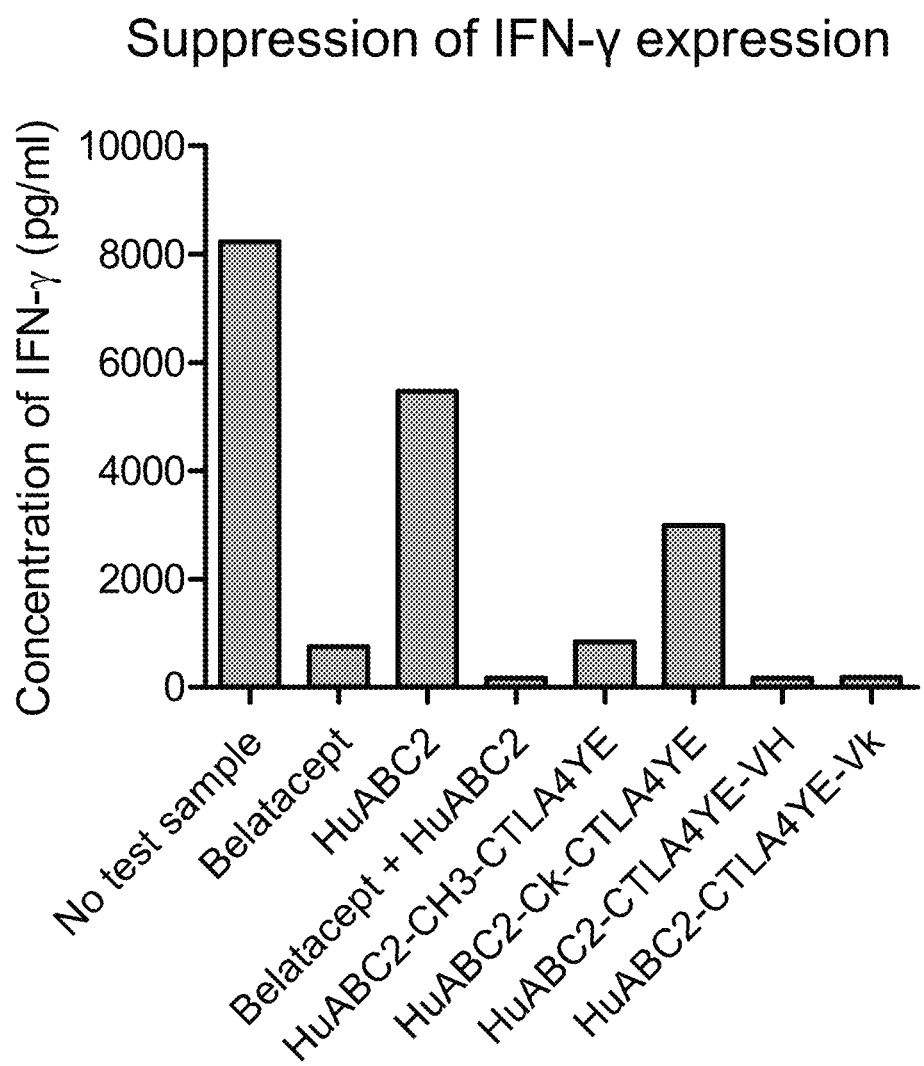
FIG. 12: Expression of IFN-γ in the mixed lymphocyte reaction.

The level of proinflammatory cytokine IFN-γ in MLR culture supernatants measured using the ELISA MAX Deluxe Set Human IFN-γ kit (BioLegend) was 8,217 pg/ml with no test sample, 744 pg/ml with belatacept, 5,459 pg/ml with HuABC2, 170 pg/ml with a combination of belatacept and HuABC2, 837 pg/ml with HuABC2-CH3-CTLA4YE, 2,984 pg/ml with HuABC2-Ck-CTLA4YE, 167 pg/ml with HuABC2-CTLA4YE-VH, and 182 pg/ml with HuABC2-CTLA4YE-Vk (FIG. 12). Both HuABC2-CTLA4YE-VH and HuABC2-CTLA4YE-Vk suppressed the production of IFN-γ as potently as the combination of HuABC2 and belatacept.

Example 12: HuABC101 Fused to CTLA-4

HuABC101, which is expressed from the vector pHuABC101 in mammalian cells, is a humanized anti-CD122 IgG1/kappa antibody comprising HuABC101 VH (SEQ ID NO:29) and HuABC101 VL (SEQ ID NO:30). The structure of pHuABC101 is same as pHuABC2p (FIG. 1A) except that the coding regions of HuABC2 VH, HuABC2 VL, and puromycin N-acetyl-transferase are replaced by HuABC101 VH, HuABC101 VL, and xanthine-guanine phosphoribosyltransferase, respectively.

Amino acid sequence of the mature heavy chain encoded in pHuABC101 is (SEQ ID NO: 53)
QVQLQESGPGLVKPSQTLSLTCTVSGYSITNDNHWWNWIRQHPGKGLEWM

GYIDSSGSSDNNPSLKSQITISRDTSKNQLSLKLSSVTAADTAVYYCARG

GGRDYYGMDYWGQGTTVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

-continued
NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

K.

Amino acid sequence of the mature light chain encoded in HuABC101 is DIVMTQSPDSLGVSLGERATIN-CRASQSVSTSSYSYVHWYQQKPGQPPKLLIKYASN-LESGVPDRFSGSGSGTDFTLTISS LQAEDVA-VYYCQHSWDIPFTFGQGTKLEIKRTVAAPSVFIFPPSD-EQLKSGTASVVCLLNNFYPREAKVQWKVDNALQS GNSQESVTEQDSKDSTYSLSSTLTLSKADYEKHKVY-ACEVTHQGLSSPVTKSFNRGEC (SEQ ID NO:54).

The variant CTLA-4 (SEQ ID NO:14) was fused to the N-terminus of mature HuABC101 VH in pHuABC101 to generate a new expression vector pHC642. The coding region of CTLA-4 fused to HuABC101 VH in pHC642 comprises, from the N- to C-terminus, a synthetic signal peptide (SEQ ID NO:35), variant CTLA-4 (SEQ ID NO:14), a flexible polypeptide linker (SGGGGSGGGGS; SEQ ID NO:36), and mature HuABC101 VH (SEQ ID NO:29) (CTLA4YE-HuABC101 VH fusion). The amino acid sequence of the CTLA4YE-HuABC101 VH fusion is (SEQ ID NO: 55)
MGWSWIFFFLLSGTASVLSMHVAQPAVVLASSRGIASFVCEYASPGKYTE

VRVTVLRQADSQVTEVCAATYMMGNELTFLDDSICTGTSSGNQVNLTIQG

LRAMDTGLYICKVELMYPPPYYEGIGNGTQIYVIDPEPCPDSDSGGGGSG

GGGSQVQLQESGPGLVKPSQTLSLTCTVSGYSITNDNHWWNWIRQHPGKG

LEWMGYIDSSGSSDNNPSLKSQITISRDTSKNQLSLKLSSVTAADTAVYY

CARGGGRDYYGMDYWGQGTTVTVSS.

The linker sequence is underlined. Mature CTLA4YE-HuABC101 VH fusion starts at position 20 of SEQ ID NO:55.

Amino acid sequence of the mature light chain encoded in pHC642 is same as the mature light chain sequence encoded in pHuABC101 (SEQ ID NO:54). Amino acid sequence of the mature heavy chain of HuABC101 fused at the N-terminus to the extracellular domain of the variant CTLA-4 followed by the linker (underlined) encoded in pHC642 is (SEQ ID NO: 56)
MHVAQPAVVLASSRGIASFVCEYASPGKYTEVRVTVLRQADSQVTEVCAA

TYMMGNELTFLDDSICTGTSSGNQVNLTIQGLRAMDTGLYICKVELMYPP

PYYEGIGNGTQIYVIDPEPCPDSDSGGGGSGGGGSQVQLQESGPGLVKPS

QTLSLTCTVSGYSITNDNHWWNWIRQHPGKGLEWMGYIDSSGSSDNNPSL

KSQITISRDTSKNQLSLKLSSVTAADTAVYYCARGGGRDYYGMDYWGQGT

TVTVSSASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKV

DKKVEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRDELTKN

-continued
QVSLTCLVKGFYPSDIAVEWESNGQPENNYKTTPPVLDSDGSFFLYSKLT

VDKSRWQQGNVFSCSVMHEALHNHYTQKSLSLSPGK.

Modified HuABC101 with fusion to CTLA-4 at the N-terminus of heavy chain, which was termed HuABC101-CTLA4YE-VH, is expressed from pHC642.

Another expression vector was constructed by fusing a flexible polypeptide linker (SEQ ID NO:11) followed by the variant CTLA-4 (SEQ ID NO:14) to the penultimate glycine residue of CH3 in pHuABC101. Amino acid sequence of the mature light chain encoded in the resulting vector pHC630 is same as the mature light chain sequence encoded in pHuABC101 (SEQ ID NO:54). Amino acid sequence of the mature heavy chain of HuABC101 fused at the C-terminus to the linker (underlined) followed by the extracellular domain of the variant CTLA-4 encoded in pHC630 is (SEQ ID NO: 57)
QVQLQESGPGLVKPSQTLSLTCTVSGYSITNDNHWWNWIRQHPGKGLEWM

GYIDSSGSSDNNPSLKSQITISRDTSKNQLSLKLSSVTAADTAVYYCARG

GGRDYYGMDYWGQGTTVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

SGGGGSGMHVAQPAVVLASSRGIASFVCEYASPGKYTEVRVTVLRQADSQ

VTEVCAATYMMGNELTFLDDSICTGTSSGNQVNLTIQGLRAMDTGLYICK

VELMYPPPYYEGIGNGTQIYVIDPEPCPDSD.

Modified HuABC101 with fusion to CTLA-4 at the C-terminus of heavy chain, which was termed HuABC101-CH3-CTLA4YE, is expressed from pHC630.

The two expression vectors (pHC642 and pHC630) were individually transfected into HEK293 cells as described above. Their expression level in culture supernatants was measured by sandwich ELISA as described above. Binding of transiently expressed HuABC101-CTLA4YE-VH and HuABC101-CH3-CTLA4YE to CD80 and CD86 was analyzed by flow cytometry as described above. Belatacept was used as a reference for binding to CD80 and CD86.

The MCF values for binding of HuABC101-CTLA4YE-VH, HuABC101-CH3-CTLA4YE and belatacept, each at 200 ng/ml, to CHO-K1/CD80 cells were 1163, 291 and 1876, respectively. The MCF values for binding of HuABC101-CTLA4YE-VH, HuABC101-CH3-CTLA4YE and belatacept, each at 200 ng/ml, to CHO-K1/CD86 cells were 745, 108 and 917, respectively. Binding of HuABC101-CH3-CTLA4YE to each of CD80 and CD86 was much weaker than the binding of HuABC101-CTLA4YE-VH. As observed with HuABC2 fused to CTLA-4, fusion of CTLA-4 to the C-terminus of heavy chain of HuABC101 unexpectedly reduced the binding to CD80 and CD86.

Example 13: HuABC77D Fused to CTLA-4

Mouse hybridoma producing an IgG/kappa monoclonal antibody ABC77 that binds to and blocks the function of human and cynomolgus CD122 was isolated at JN Biosciences (Mountain View, CA) following standard cell fusion techniques using GenomONE CF EX Cell Fusion Reagent (Cosmo Bio, Carlsbad, CA) as described in U.S. Pat. No. 9,028,830. Sequencing and humanization VH and VL of ABC77 were performed as described in Tsurushita et al. (Methods 36: 69-83, 2005).

Amino acid sequence of humanized ABC77 VH (HuABC77D VH) is (SEQ ID NO: 58)
MDFGLIFFIVALLKGVQCEVQLVESGGGLVQPGGSLRLSCAASGFDFSRY

WMSWVRQAPGKGLEWIGEINPDSSTINYAPSLKDRFTISRDNAKNSLYLQ

MNSLRAEDTAVYYCARHDYDEGIYFDYWGQGTTVTVSS.

Amino acid sequences of CDR1, 2 and 3 of HuABC77D VH based on the definition of Kabat et al. (supra) is RYWMS (SEQ ID NO:59), EINPDSSTINYAPSLKD (SEQ ID NO:60) and HDYDEGIYFDY (SEQ ID NO:61), respectively. Mature HuABC77D VH starts at position 19 of SEQ ID NO:58.

Amino acid sequence of humanized ABC77 VL (HuABC77D VL) is (SEQ ID NO: 62)
MDFQVQIFSFLLISASVIISRGDIQMTQSPSSLSASVGDRVTITCSASSR

VIYMHWYQQKPGKAPKRWIYDTSKLASGVPSRFSGSGSGTEFTLTISSLQ

PEDFATYYCQQWSSNPPTFGGGTKVEIK.

Amino acid sequences of CDR1, 2 and 3 of HuABC77D VL based on the definition of Kabat et al. (supra) is SASSRVIYMH (SEQ ID NO:63), DTSKLAS (SEQ ID NO:64) and QQWSSNPPT (SEQ ID NO:65), respectively. Mature HuABC77D VL starts at position 23 of SEQ ID NO:62.

The expression vector pHuABC77D is a derivative of pHuABC2p, in which the coding regions of HuABC2 VH and VL are replaced by those of HuABC77D VH and VL, respectively. Leucine residues at positions 234 and 235 (EU numbering) in CH2 of pHuABC77D were both changed to alanine residues to eliminate binding to Fc gamma receptors (Hezareh et al., J. Virol. 75:12161-12168, 2001).

Amino acid sequence of the mature heavy chain encoded in pHuABC77D is (SEQ ID NO: 66)
EVQLVESGGGLVQPGGSLRLSCAASGFDFSRYWMSWVRQAPGKGLEWIGE

INPDSSTINYAPSLKDRFTISRDNAKNSLYLQMNSLRAEDTAVYYCARHD

YDEGIYFDYWGQGTTVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPEAAGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK

Amino acid sequence of the mature light chain encoded in pHuABC77D is (SEQ ID NO: 67)
DIQMTQSPSSLSASVGDRVTITCSASSRVIYMHWYQQKPGKAPKRWIYDT

SKLASGVPSRFSGSGSGTEFTLTISSLQPEDFATYYCQQWSSNPPTFGGG

TKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC.

CHO-K1 cells stably transfected with pHuABC77D were generated and expanded in SFM4CHO media as described above. Humanized ABC77 IgG1/kappa antibody (HuABC77D) was purified from culture supernatants as described above. HuABC77D showed (i) specific binding to human and cynomolgus CD122 and (ii) blocking of the interaction of human CD122 with human IL-2 and IL-15.

The variant CTLA-4 (SEQ ID NO:14) was fused to the N-terminus of mature HuABC77D VH in pHuABC77D to generate a new expression vector pHC644. The coding region of CTLA-4 fused to HuABC77D VH in pHC644 comprises, from the N- to C-terminus, a synthetic signal peptide (SEQ ID NO:35), variant CTLA-4 (SEQ ID NO:14), a flexible polypeptide linker (SGGGGSGGGGS; SEQ ID NO:36), and mature HuABC77D VH (SEQ ID NO:68) (CTLA4YE-HuABC77D VH fusion). The amino acid sequence of mature CTLA4YE-HuABC77D VH fusion is (SEQ ID NO: 69)
MHVAQPAVVLASSRGIASFVCEYASPGKYTEVRVTVLRQADSQVTEVCAA

TYMMGNELTFLDDSICTGTSSGNQVNLTIQGLRAMDTGLYICKVELMYPP

PYYEGIGNGTQIYVIDPEPCPDSDSGGGGSGGGGSEVQLVESGGGLVQPG

GSLRLSCAASGFDFSRYWMSWVRQAPGKGLEWIGEINPDSSTINYAPSLK

DRFTISRDNAKNSLYLQMNSLRAEDTAVYYCARHDYDEGIYFDYWGQGTT

VTVSS.

The linker sequence is underlined.

Amino acid sequence of the mature light chain encoded in pHC644 is same as the mature light chain sequence encoded in pHuABC77D (SEQ ID NO:67). Amino acid sequence of the mature heavy chain of HuABC77D fused at the N-terminus to the extracellular domain of the variant CTLA-4 followed by the linker (underlined) encoded in pHC644 is (SEQ ID NO: 70)
MHVAQPAVVLASSRGIASFVCEYASPGKYTEVRVTVLRQADSQVTEVCAA

TYMMGNELTFLDDSICTGTSSGNQVNLTIQGLRAMDTGLYICKVELMYPP

PYYEGIGNGTQIYVIDPEPCPDSDSGGGGSGGGGSEVQLVESGGGLVQPG

GSLRLSCAASGFDFSRYWMSWVRQAPGKGLEWIGEINPDSSTINYAPSLK

DRFTISRDNAKNSLYLQMNSLRAEDTAVYYCARHDYDEGIYFDYWGQGTT

VTVSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTKVD

KKVEPKSCDKTHTCPPCPAPEAAGGPSVFLFPPKPKDTLMISRTPEVTCV

VVDVSHEDPEVKFNWYVDGVEVHNAKTKPREEQYNSTYRVVSVLTVLHQD

-continued
```
WLNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLTV

DKSRWQQGNVFSCSVMHEALHNHYTQKSLSLSPGK.
```

Modified HuABC77D with fusion to CTLA-4 at the N-terminus of heavy chain, which was termed HuABC77D-CTLA4YE-VH, is expressed from pHC644.

Another expression vector was constructed by fusing the variant CTLA-4 (SEQ ID NO:14) to the penultimate glycine residue of CH3 in pHuABC77D. Amino acid sequence of the mature light chain encoded in the resulting vector pHC645 is same as the mature light chain sequence encoded in pHuABC77D (SEQ ID NO:67). Amino acid sequence of the mature heavy chain of HuABC77D fused at the C-terminus to the linker (underlined) followed by the extracellular domain of the variant CTLA-4 encoded in pHC645 is

```
                                          (SEQ ID NO: 71)
EVQLVESGGGLVQPGGSLRLSCAASGFDFSRYWMSWVRQAPGKGLEWIGE

INPDSSTINYAPSLKDRFTISRDNAKNSLYLQMNSLRAEDTAVYYCARHD

YDEGIYFDYWGQGTTVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPEAAGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGS

GGGGSGMHVAQPAVVLASSRGIASFVCEYASPGKYTEVRVTVLRQADSQV

TEVCAATYMMGNELTFLDDSICTGTSSGNQVNLTIQGLRAMDTGLYICKV

ELMYPPPYYEGIGNGTQIYVIDPEPCPDSD.
```

Modified HuABC77D with fusion to CTLA-4 at the C-terminus of heavy chain, which was termed HuABC77D-CH3-CTLA4YE, is expressed from pHC645.

The two expression vectors (pHC644 and pHC645) were individually transfected into HEK293 cells as described above. Their expression level in culture supernatants was measured by sandwich ELISA as described above. Binding of HuABC77D-CH3-CTLA4YE and HuABC77D-CTLA4YE-VH to CHO-K1/CD80 and CHO-K1/CD86 cells was analyzed by flow cytometry as described above. Belatacept was used as a reference for binding to CD80 and CD86. The test samples were used at 500 ng/ml and four steps of 3-fold serial dilutions.

The results of binding to CHO-K1/CD80 and CHO-K1/CD86 cells are shown in FIGS. 13A and B, respectively. Belatacept and HuABC77D-CTLA4YE-VH showed the same level of binding to each of CD80 and CD86, whereas the binding of HuABC77D-CH3-CTLA4YE was much weaker when compared to the binding of belatacept and HuABC77D-CTLA4YE-VH. The MCF values for binding of belatacept, HuABC77D-CTLA4YE-VH and HuABC77D-CH3-CTLA4YE, each at 500 ng/ml, to CHO-K1/CD80 cells were 4390, 4594 and 1809, respectively. The MCF values for binding of belatacept, HuABC77D-CTLA4YE-VH and HuABC77D-CH3-CTLA4YE, each at 500 ng/ml, to CHO-K1/CD86 cells were 723, 794 and 118, respectively. As observed with HuABC2 and HuABC101, fusion of CTLA-4 to the C-terminus of heavy chain unexpectedly reduced the binding of HuABC77D to CD80 and CD86.

Binding of HuABC77D, HuABC77D-CTLA4YE-VH and HuABC77D-CH3-CTLA4YE to CD122 was analyzed by flow cytometry using NS0/CD122 cells as described above. No major difference was observed with the CD122 binding pattern among HuABC77D, HuABC77D-CTLA4YE-VH and HuABC77D-CH3-CTLA4YE. This result indicates that fusion of CTLA-4 at the N-terminus of HuABC77D heavy chain does not negatively affect antigen binding of HuABC77D.

```
Sequence listing
Amino acid sequence of HuABC2 VH
                                                         SEQ ID NO: 1
MKLWLNWVFLLTLLHGIQCEVQLVESGGGLVQPGGSLRLSCAASGFTFSDFYMEWVRQAPGKGLEWIAASRNKAND

YTTEYSASVKGRFIVSRDDSKNSLYLQMNSLKTEDTAVYYCARSYYRYDGMDYWGQGTTVTVSS

Amino acid sequence of HuABC2 VL
                                                         SEQ ID NO: 2
MDFQVQIFSFLLISASVIVSRGEIVLTQSPATLSLSPGERATLSCSAISSVSYMYWYQQKPGQAPRLLIYDTSNLVSGVPAR

FSGSGSGTDYTLTISSLEPEDFAVYYCQQWNTYPYTFGGGTKVEIK

Amino acid sequence of the CH1 region of human gamma-1 heavy chain encoded in
pHuABC2p
                                                         SEQ ID NO: 3
ASTKGPSVFPLAPSSKSTSGGTAALGCLVKDYFPEPVTVSWNSGALTSGVHTFPAVLQSSGLYSLSSVVTVPSSSLGTQTY

ICNVNHKPSNTKVDKKV

Amino acid sequence of the hinge region of human gamma-1 heavy chain encoded in
pHuABC2p
                                                         SEQ ID NO: 4
EPKSCDKTHTCPPCP
```

-continued

Amino acid sequence of the CH2 region of human gamma-1 heavy chain encoded in pHuABC2p

SEQ ID NO: 5

APELLGGPSVFLFPPKPKDTLMISRTPEVTCVVVDVSHEDPEVKFNWYVDGVEVHNAKTKPREEQYNSTYRVVSVLTVL

HQDWLNGKEYKCKVSNKALPAPIEKTISKAK

Amino acid sequence of the CH3 region of human gamma-1 heavy chain encoded in pHuABC2p

SEQ ID NO: 6

GQPREPQVYTLPPSRDELTKNQVSLTCLVKGFYPSDIAVEWESNGQPENNYKTTPPVLDSDGSFFLYSKLTVDKSRWQQ

GNVFSCSVMHEALHNHYTQKSLSLSPGK

Amino acid sequence of the Ck region encoded in pHuABC2p

SEQ ID NO: 7

TVAAPSVFIFPPSDEQLKSGTASVVCLLNNFYPREAKVQWKVDNALQSGNSQESVTEQDSKDSTYSLSSTLTLSKADYEK

HKVYACEVTHQGLSSPVTKSFNRGEC

Amino acid sequence of the mature heavy chain of HuABC2 encoded in pHuABC2p

SEQ ID NO: 8

EVQLVESGGGLVQPGGSLRLSCAASGFTFSDFYMEWVRQAPGKGLEWIAASRNKANDYTTEYSASVKGRFIVSRDDSK

NSLYLQMNSLKTEDTAVYYCARSYYRYDGMDYWGQGTTVTVSSASTKGPSVFPLAPSSKSTSGGTAALGCLVKDYFPEP

VTVSWNSGALTSGVHTFPAVLQSSGLYSLSSVVTVPSSSLGTQTYICNVNHKPSNTKVDKKVEPKSCDKTHTCPPCPAPE

LLGGPSVFLFPPKPKDTLMISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLSLSPGK

Amino acid sequence of the mature light chain of HuABC2 encoded in pHuABC2p

SEQ ID NO: 9

EIVLTQSPATLSLSPGERATLSCSAISSVSYMYWYQQKPGQAPRLLIYDTSNLVSGVPARFSGSGSGTDYTLTISSLEPEDF

AVYYCQQWNTYPYTFGGGTKVEIKRTVAAPSVFIFPPSDEQLKSGTASVVCLLNNFYPREAKVQWKVDNALQSGNSQE

SVTEQDSKDSTYSLSSTLTLSKADYEKHKVYACEVTHQGLSSPVTKSFNRGEC

Amino acid sequence of the extracellular domain of human CTLA-4

SEQ ID NO: 10

MHVAQPAVVLASSRGIASFVCEYASPGKATEVRVTVLRQADSQVTEVCAATYMMGNELTFLDDSICTGTSSGNQVNLT

IQGLRAMDTGLYICKVELMYPPPYYLGIGNGTQIYVIDPEPCPDSD

Amino acid sequence of the flexible polypeptide linker

SEQ ID NO: 11

SGGGGSG

Amino acid sequence of the fusion of CH3 to the linker and extracellular domain of CTLA-4 (CH3-CTLA4 fusion) encoded in pHC624

SEQ ID NO: 12

GQPREPQVYTLPPSRDELTKNQVSLTCLVKGFYPSDIAVEWESNGQPENNYKTTPPVLDSDGSFFLYSKLTVDKSRWQQ

GNVFSCSVMHEALHNHYTQKSLSLSPGSGGGGSGMHVAQPAVVLASSRGIASFVCEYASPGKATEVRVTVLRQADSQ

VTEVCAATYMMGNELTFLDDSICTGTSSGNQVNLTIQGLRAMDTGLYICKVELMYPPPYYLGIGNGTQIYVIDPEPCPDSD

Amino acid sequence of the mature heavy chain of HuABC2 fused at the C-terminus to the linker followed by the extracellular domain of CTLA-4 encoded in pHC624

SEQ ID NO: 13

EVQLVESGGGLVQPGGSLRLSCAASGFTFSDFYMEWVRQAPGKGLEWIAASRNKANDYTTEYSASVKGRFIVSRDDSK

NSLYLQMNSLKTEDTAVYYCARSYYRYDGMDYWGQGTTVTVSSASTKGPSVFPLAPSSKSTSGGTAALGCLVKDYFPEP

VTVSWNSGALTSGVHTFPAVLQSSGLYSLSSVVTVPSSSLGTQTYICNVNHKPSNTKVDKKVEPKSCDKTHTCPPCPAPE

AAGGPSVFLFPPKPKDTLMISRTPEVTCVVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKSLSLSPGSGGGGSGMHVAQPAVVLASSR

GIASFVCEYASPGKATEVRVTVLRQADSQVTEVCAATYMMGNELTFLDDSICTGTSSGNQVNLTIQGLRAMDTGLYICK

VELMYPPPYYLGIGNGTQIYVIDPEPCPDSD

-continued

Amino acid sequence of the extracellular domain of the variant human CTLA-4 carrying the A29Y and L104E mutations (variant CTLA-4)

SEQ ID NO: 14
MHVAQPAVVLASSRGIASFVCEYASPGKYTEVRVTVLRQADSQVTEVCAATYMMGNELTFLDDSICTGTSSGNQVNLT
IQGLRAMDTGLYICKVELMYPPPYYEGIGNGTQIYVIDPEPCPDSD

Amino acid sequence of CH3 fused at the C-terminus to the linker followed by the extracellular domain of the variant CTLA-4 encoded in pHC625 and pHC622

SEQ ID NO: 15
GQPREPQVYTLPPSRDELTKNQVSLTCLVKGFYPSDIAVEWESNGQPENNYKTTPPVLDSDGSFFLYSKLTVDKSRWQQ
GNVFSCSVMHEALHNHYTQKSLSLSPGSGGGGSGMHVAQPAVVLASSRGIASFVCEYASPGKYTEVRVTVLRQADSQ
VTEVCAATYMMGNELTFLDDSICTGTSSGNQVNLTIQGLRAMDTGLYICKVELMYPPPYYEGIGNGTQIYVIDPEPCPDSD

Amino acid sequence of the mature heavy chain of HuABC2 fused at the C-terminus to the linker followed by the extracellular domain of the variant CTLA-4 encoded in pHC625 and pHC622

SEQ ID NO: 16
EVQLVESGGGLVQPGGSLRLSCAASGFTFSDFYMEWVRQAPGKGLEWIAASRNKANDYTTEYSASVKGRFIVSRDDSK
NSLYLQMNSLKTEDTAVYYCARSYYRYDGMDYWGQGTTVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCPAPE
AAGGPSVFLFPPKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKSLSLSPGSGGGGSGMHVAQPAVVLASSR
GIASFVCEYASPGKYTEVRVTVLRQADSQVTEVCAATYMMGNELTFLDDSICTGTSSGNQVNLTIQGLRAMDTGLYICK
VELMYPPPYYEGIGNGTQIYVIDPEPCPDSD

ABC2 VH CDR1 amino acid sequence
SEQ ID NO: 17
DFYME

ABC2 VH CDR2 amino acid sequence
SEQ ID NO: 18
ASRNKANDYTTEYSASVKG

ABC2 VH CDR3 amino acid sequence
SEQ ID NO: 19
SYYRYDGMDY

ABC2 VL CDR1 amino acid sequence
SEQ ID NO: 20
SAISSVSYMY

ABC2 VL CDR2 amino acid sequence
SEQ ID NO: 21
DTSNLVS

ABC2 VL CDR3 amino acid sequence
SEQ ID NO: 22
QQWNTYPYT

ABC101 VH CDR1 amino acid sequence
SEQ ID NO: 23
NDNHWWN

ABC101 VH CDR2 amino acid sequence
SEQ ID NO: 24
YIDSSGSSDNNPSLKS

ABC101 VH CDR3 amino acid sequence
SEQ ID NO: 25
GGGRDYYGMDY

ABC101 VL CDR1 amino acid sequence
SEQ ID NO: 26
RASQSVSTSSYSYVH

ABC101 VL CDR2 amino acid sequence
SEQ ID NO: 27
YASNLES

ABC101 VL CDR3 amino acid sequence
SEQ ID NO: 28
QHSWDIPFT

Amino acid sequence of the mature HuABC101 VH
SEQ ID NO: 29
QVQLQESGPGLVKPSQTLSLTCTVSGYSITNDNHWWNWIRQHPGKGLEWMGYIDSSGSSDNNPSLKSQITISRDTSKN
QLSLKLSSVTAADTAVYYCARGGGRDYYGMDYWGQGTTVTVSS Amino acid sequence of the mature HuABC101 VL
SEQ ID NO: 30
DIVMTQSPDSLGVSLGERATINCRASQSVSTSSYSYVHWYQQKPGQPPKLLIKYASNLESGVPDRFSGSGSGTDFTLTISS
LQAEDVAVYYCQHSWDIPFTFGQGTKLEIK Amino acid sequence of the mature human CD122
SEQ ID NO: 31
AVNGTSQFTCFYNSRANISCVWSQDGALQDTSCQVHAWPDRRRWNQTCELLPVSQASWACNLILGAPDSQKLTTVD
IVTLRVLCREGVRWRVMAIQDFKPFENLRLMAPISLQVVHVETHRCNISWEISQASHYFERHLEFEARTLSPGHTWEEA
PLLTLKQKQEWICLETLTPDTQYEFQVRVKPLQGEFTTWSPWSQPLAFRTKPAALGKDTIPWLGHLLVGLSGAFGElILV
YLLINCRNTGPWLKKVLKCNTPDPSKFFSQLSSEHGGDVQKWLSSPFPSSSFSPGGLAPEISPLEVLERDKVTQLLLQQDK
VPEPASLSSNHSLTSCFTNQGYFFFHLPDALEIEACQVYFTYDPYSEEDPDEGVAGAPTGSSPQPLQPLSGEDDAYCTFPS
RDDLLLFSPSLLGGPSPPSTAPGGSGAGEERMPPSLQERVPRDWDPQPLGPPTPGVPDLVDFQPPPELVLREAGEEVP
DAGPREGVSFPWSRPPGQGEFRALNARLPLNTDAYLSLQELQGQDPTHLV Amino acid sequence of Ck fused to the linker followed by the extracellular
domain of the variant CTLA-4 (Ck-CTLA4YE fusion) encoded in pHC623
SEQ ID NO: 32
RTVAAPSVFIFPPSDEQLKSGTASVVCLLNNFYPREAKVQWKVDNALQSGNSQESVTEQDSKDSTYSLSSTLTLSKADYE
KHKVYACEVTHQGLSSPVTKSFNRGECSGGGGSGMHVAQPAVVLASSRGIASFVCEYASPGKYTEVRVTVLRQADSQV
TEVCAATYMMGNELTFLDDSICTGTSSGNQVNLTIQGLRAMDTGLYICKVELMYPPPYYEGIGNGTQIYVIDPEPCPDSD Amino acid sequence of the mature heavy chain of HuABC2 encoded in pHC623
SEQ ID NO: 33
EVQLVESGGGLVQPGGSLRLSCAASGFTFSDFYMEWVRQAPGKGLEWIAASRNKANDYTTEYSASVKGRFIVSRDDSK
NSLYLQMNSLKTEDTAVYYCARSYYRYDGMDYWGQGTTVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCPAPE
AAGGPSVFLFPPKPKDTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKSLSLSPGK Amino acid sequence of the mature light chain of HuABC2 fused at the C-terminus
to the linker followed by the extracellular domain of the variant CTLA-4 encoded
in pHC623
SEQ ID NO: 34
EIVLTQSPATLSLSPGERATLSCSAISSVSYMYWYQQKPGQAPRLLIYDTSNLVSGVPARFSGSGSGTDYTLTISSLEPEDF
AVYYCQQWNTYPYTFGGGTKVEIKRTVAAPSVFIFPPSDEQLKSGTASVVCLLNNFYPREAKVQWKVDNALQSGNSQE
SVTEQDSKDSTYSLSSTLTLSKADYEKHKVYACEVTHQGLSSPVTKSFNRGECSGGGGSGMHVAQPAVVLASSRGIASF
VCEYASPGKYTEVRVTVLRQADSQVTEVCAATYMMGNELTFLDDSICTGTSSGNQVNLTIQGLRAMDTGLYICKVELM
YPPPYYEGIGNGTQIYVIDPEPCPDSD Amino acid sequence of the synthetic signal peptide
SEQ ID NO: 35
MGWSWIFFFLLSGTASVLS Amino acid sequence of the flexible polypeptide linker
SEQ ID NO: 36
SGGGGSGGGGS Amino acid sequence of the mature HuABC2 VH
SEQ ID NO: 37

EVQLVESGGGLVQPGGSLRLSCAASGFTFSDFYMEWVRQAPGKGLEWIAASRNKANDYTTEYSASVKGRFIVSRDDSK

NSLYLQMNSLKTEDTAVYYCARSYYRYDGMDYWGQGTTVTVSS

Amino acid sequence of the mature HuABC2 VH fused at the N-terminus to the signal
peptide followed by the linker and extracellular domain of the variant CTLA-4
(CTLA4YE-VH fusion)
SEQ ID NO: 38

MGWSWIFFFLLSGTASVLSMHVAQPAVVLASSRGIASFVCEYASPGKYTEVRVTVLRQADSQVTEVCAATYMMGNEL

TFLDDSICTGTSSGNQVNLTIQGLRAMDTGLYICKVELMYPPPYYEGIGNGTQIYVIDPEPCPDSDSGGGGSGGGGSEV

QLVESGGGLVQPGGSLRLSCAASGFTFSDFYMEWVRQAPGKGLEWIAASRNKANDYTTEYSASVKGRFIVSRDDSKNS

LYLQMNSLKTEDTAVYYCARSYYRYDGMDYWGQGTTVTVSS

Amino acid sequence of the mature heavy chain of HuABC2 fused at the N-terminus
to the extracellular domain of the variant CTLA-4 followed by the linker encoded
in pHC640
SEQ ID NO: 39

MHVAQPAVVLASSRGIASFVCEYASPGKYTEVRVTVLRQADSQVTEVCAATYMMGNELTFLDDSICTGTSSGNQVNLT

IQGLRAMDTGLYICKVELMYPPPYYEGIGNGTQIYVIDPEPCPDSDSGGGGSGGGGSEVQLVESGGGLVQPGGSLRLSC

AASGFTFSDFYMEWVRQAPGKGLEWIAASRNKANDYTTEYSASVKGRFIVSRDDSKNSLYLQMNSLKTEDTAVYYCAR

SYYRYDGMDYWGQGTTVTVSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKTHTCPPCPAPEAAGGPSVFLFPPKPKDTLMISR

TPEVTCVVVDVSHEDPEVKFNWYVDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENNYKTTPPVLDSDGSFFLYSKLTVDK

SRWQQGNVFSCSVMHEALHNHYTQKSLSLSPGK

Amino acid sequence of the mature HuABC2 VL
SEQ ID NO: 40

EIVLTQSPATLSLSPGERATLSCSAISSVSYMYWYQQKPGQAPRLLIYDTSNLVSGVPARFSGSGSGTDYTLTISSLEPEDF

AVYYCQQWNTYPYTFGGGTKVEIK

Amino acid sequence of the mature HuABC2 VL fused at the N-terminus to the
extracellular domain of the variant CTLA-4 followed by the linker (CTLA4YE-Vk
fusion)
SEQ ID NO: 41

MHVAQPAVVLASSRGIASFVCEYASPGKYTEVRVTVLRQADSQVTEVCAATYMMGNELTFLDDSICTGTSSGNQVNLT

IQGLRAMDTGLYICKVELMYPPPYYEGIGNGTQIYVIDPEPCPDSDSGGGGSGGGGSEIVLTQSPATLSLSPGERATLSCS

AISSVSYMYWYQQKPGQAPRLLIYDTSNLVSGVPARFSGSGSGTDYTLTISSLEPEDFAVYYCQQWNTYPYTFGGGTKVEIK

Amino acid sequence of the mature light chain of HuABC2 fused at the N-terminus
to the extracellular domain of the variant CTLA-4 followed by the linker encoded
in pHC641
SEQ ID NO: 42

MHVAQPAVVLASSRGIASFVCEYASPGKYTEVRVTVLRQADSQVTEVCAATYMMGNELTFLDDSICTGTSSGNQVNLT

IQGLRAMDTGLYICKVELMYPPPYYEGIGNGTQIYVIDPEPCPDSDSGGGGSGGGGSEIVLTQSPATLSLSPGERATLSCS

AISSVSYMYWYQQKPGQAPRLLIYDTSNLVSGVPARFSGSGSGTDYTLTISSLEPEDFAVYYCQQWNTYPYTFGGGTKV

EIKRTVAAPSVFIFPPSDEQLKSGTASVVCLLNNFYPREAKVQWKVDNALQSGNSQESVTEQDSKDSTYSLSSTLTLSKA

DYEKHKVYACEVTHQGLSSPVTKSFNRGEC

Amino acid sequence of the extra cellular region of human CD80
SEQ ID NO: 43

VIHVTKEVKEVATLSCGHNVSVEELAQTRIYWQKEKKMVLTMMSGDMNIWPEYKNRTIFDITNNLSIVILALRPSDEGT

YECVVLKYEKDAFKREHLAEVTLSVKADFPTPSISDFEIPTSNIRRIICSTSGGFPEPHLSWLENGEELNAINTTVSQDPETEL

YAVSSKLDFNMTTNHSFMCLIKYGHLRVNQTFNWNTTKQEHFPDN

```
Amino acid sequence of the FLAG polypeptide
                                                                SEQ ID NO: 44
DYKDDDDK Amino acid sequence of the GPI anchorage signal derived from human CD55
                                                                SEQ ID NO: 45
PNKGSGTTSGTTRLLSGHTCFTLTGLLGTLVTMGLLT Amino acid sequence of the mature CD80-FLAG-GPI
                                                                SEQ ID NO: 46
VIHVTKEVKEVATLSCGHNVSVEELAQTRIYWQKEKKMVLTMMSGDMNIWPEYKNRTIFDITNNLSIVILALRPSDEGT YECVVLKYEKDAFKREHLAEVTLSVKADFPTPSISDFEIPTSNIRRIICSTSGGFPEPHLSWLENGEELNAINTTVSQDPETEL

YAVSSKLDFNMTTNHSFMCLIKYGHLRVNQTFNWNTTKQEHFPDNTGGGDYKDDDDKGGGPNKGSGTTSGTTRLLS

GHTCFTLTGLLGTLVTMGLLT

Amino acid sequence of the extra cellular region of human CD86
                                                                SEQ ID NO: 47
LKIQAYFNETADLPCQFANSQNQSLSELVVFWQDQENLVLNEVYLGKEKFDSVHSKYMGRTSFDSDSWTLRLHNLQIK DKGLYQCIIHHKKPTGMIRIHQMNSELSVLANFSQPEIVPISNITENVYINLTCSSIHGYPEPKKMSVLLRTKNSTIEYDGIM

QKSQDNVTELYDVSISLSVSFPDVTSNMTIFCILETDKTRLLSSPFSIELEDPQPPPDH

Amino acid sequence of the mature CD86-FLAG-GPI
                                                                SEQ ID NO: 48
LKIQAYFNETADLPCQFANSQNQSLSELVVFWQDQENLVLNEVYLGKEKFDSVHSKYMGRTSFDSDSWTLRLHNLQIK DKGLYQCIIHHKKPTGMIRIHQMNSELSVLANFSQPEIVPISNITENVYINLTCSSIHGYPEPKKMSVLLRTKNSTIEYDGIM

QKSQDNVTELYDVSISLSVSFPDVTSNMTIFCILETDKTRLLSSPFSIELEDPQPPPDHTGGGDYKDDDDKGGGPNKGSG

TTSGTTRLLSGHTCFTLTGLLGTLVTMGLLT

Amino acid sequence of belatacept
                                                                SEQ ID NO: 49
MHVAQPAVVLASSRGIASFVCEYASPGKYTEVRVTVLRQADSQVTEVCAATYMMGNELTFLDDSICTGTSSGNQVNLT IQGLRAMDTGLYICKVELMYPPPYYEGIGNGTQIYVIDPEPCPDSDQEPKSSDKTHTSPPSPAPELLGGSSVFLFPPKPKD

TLMISRTPEVTCVVVDVSHEDPEVKFNWYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSDIAVEWESNGQPENNYKTTPPVLDSDGSFFLY

SKLTVDKSRWQQGNVFSCSVMHEALHNHYTQKSLSLSPGK

Amino acid sequence of the polypeptide linker
                                                                SEQ ID NO: 50
SGGGGSGGGGSGGGGS Amino acid sequence of the extracellular domain of human CD122
                                                                SEQ ID NO: 51
AVNGTSQFTCFYNSRANISCVWSQDGALQDTSCQVHAWPDRRRWNQTCELLPVSQASWACNLILGAPDSQKLTTVD

IVTLRVLCREGVRWRVMAIQDFKPFENLRLMAPISLQVVHVETHRCNISWEISQASHYFERHLEFEARTLSPGHTWEEA

PLLTLKQKQEWICLETLTPDTQYEFQVRVKPLQGEFTTWSPWSQPLAFRTKPAALGKDT

Amino acid sequence of CD122-FLAG-GPI encoded in pFCm148
                                                                SEQ ID NO: 52
AVNGTSQFTCFYNSRANISCVWSQDGALQDTSCQVHAWPDRRRWNQTCELLPVSQASWACNLILGAPDSQKLTTVD

IVTLRVLCREGVRWRVMAIQDFKPFENLRLMAPISLQVVHVETHRCNISWEISQASHYFERHLEFEARTLSPGHTWEEA

PLLTLKQKQEWICLETLTPDTQYEFQVRVKPLQGEFTTWSPWSQPLAFRTKPAALGKDTTGGGDYKDDDDKGGGPNK

GSGTTSGTTRLLSGHTCFTLTGLLGTLVTMGLLT

Amino acid sequence of the mature heavy chain of HuABC101 encoded in pHuABC101
                                                                SEQ ID NO: 53
QVQLQESGPGLVKPSQTLSLTCTVSGYSITNDNHWWNWIRQHPGKGLEWMGYIDSSGSSDNNPSLKSQITISRDTSKN

QLSLKLSSVTAADTAVYYCARGGGRDYYGMDYWGQGTTVTVSSASTKGPSVFPLAPSSKSTSGGTAALGCLVKDYFPEP

VTVSWNSGALTSGVHTFPAVLQSSGLYSLSSVVTVPSSSLGTQTYICNVNHKPSNTKVDKKVEPKSCDKTHTCPPCPAPE

LLGGPSVFLFPPKPKDTLMISRTPEVTCVVVDVSHEDPEVKFNWYVDGVEVHNAKTKPREEQYNSTYRVVSVLTVLHQD
```

-continued

WLNGKEYKCKVSNKALPAPIEKTISKAKGQPREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLSLSPGK

Amino acid sequence of the mature light chain of HuABC101 encoded in pHuABC101
SEQ ID NO: 54
DIVMTQSPDSLGVSLGERATINCRASQSVSTSSYSYVHWYQQKPGQPPKLLIKYASNLESGVPDRFSGSGSGTDFTLTISS

LQAEDVAVYYCQHSWDIPFTFGQGTKLEIKRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSFNRGEC

Amino acid sequence of the mature HuABC101 VH fused at the N-terminus to the
extracellular domain of the variant CTLA-4 followed by the linker (CTLA4YE-
HuABC101 VH fusion)
SEQ ID NO: 55
MGWSWIFFFLLSGTASVLSMHVAQPAVVLASSRGIASFVCEYASPGKYTEVRVTVLRQADSQVTEVCAATYMMGNEL

TFLDDSICTGTSSGNQVNLTIQGLRAMDTGLYICKVELMYPPPYYEGIGNGTQIYVIDPEPCPDSDSGGGGSGGGGSQV

QLQESGPGLVKPSQTLSLTCTVSGYSITNDNHWWNWIRQHPGKGLEWMGYIDSSGSSDNNPSLKSQITISRDTSKNQL

SLKLSSVTAADTAVYYCARGGGRDYYGMDYWGQGTTVTVSS

Amino acid sequence of the mature heavy chain of HuABC101 fused at the N-terminus
to the extracellular domain of the variant CTLA-4 followed by the linker encoded
in pHC642
SEQ ID NO: 56
MHVAQPAVVLASSRGIASFVCEYASPGKYTEVRVTVLRQADSQVTEVCAATYMMGNELTFLDDSICTGTSSGNQVNLT

IQGLRAMDTGLYICKVELMYPPPYYEGIGNGTQIYVIDPEPCPDSDSGGGGSGGGGSQVQLQESGPGLVKPSQTLSLTC

TVSGYSITNDNHWWNWIRQHPGKGLEWMGYIDSSGSSDNNPSLKSQITISRDTSKNQLSLKLSSVTAADTAVYYCARG

GGRDYYGMDYWGQGTTVTVSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKTHTCPPCPAPELLGGPSVFLFPPKPKDTLMISR

TPEVTCVVVDVSHEDPEVKFNWYVDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENNYKTTPPVLDSDGSFFLYSKLTVDK

SRWQQGNVFSCSVMHEALHNHYTQKSLSLSPGK

Amino acid sequence of the mature heavy chain of HuABC101 fused at the C-terminus
to the linker followed by the extracellular domain of the variant CTLA-4 encoded
in pHC630
SEQ ID NO: 57
QVQLQESGPGLVKPSQTLSLTCTVSGYSITNDNHWWNWIRQHPGKGLEWMGYIDSSGSSDNNPSLKSQITISRDTSKN

QLSLKLSSVTAADTAVYYCARGGGRDYYGMDYWGQGTTVTVSSASTKGPSVFPLAPSSKSTSGGTAALGCLVKDYFPEP

VTVSWNSGALTSGVHTFPAVLQSSGLYSLSSVVTVPSSSLGTQTYICNVNHKPSNTKVDKKVEPKSCDKTHTCPPCPAPE

LLGGPSVFLFPPKPKDTLMISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLSLSPGSGGGGSGMHVAQPAVVLASSRGI

ASFVCEYASPGKYTEVRVTVLRQADSQVTEVCAATYMMGNELTFLDDSICTGTSSGNQVNLTIQGLRAMDTGLYICKVE

LMYPPPYYEGIGNGTQIYVIDPEPCPDSD

Amino acid sequence of HuABC77D VH
SEQ ID NO: 58
MDFGLIFFIVALLKGVQCEVQLVESGGGLVQPGGSLRLSCAASGFDFSRYWMSWVRQAPGKGLEWIGEINPDSSTINY

APSLKDRFTISRDNAKNSLYLQMNSLRAEDTAVYYCARHDYDEGIYFDYWGQGTTVTVSS

HuABC77D VH CDR1 amino acid sequences
SEQ ID NO: 59
RYWMS

HuABC77D VH CDR2 amino acid sequences
SEQ ID NO: 60
EINPDSSTINYAPSLKD

HuABC77D VH CDR3 amino acid sequences
SEQ ID NO: 61
HDYDEGIYFDY

Amino acid sequence of HuABC77D VL
SEQ ID NO: 62
MDFQVQIFSFLLISASVIISRGDIQMTQSPSSLSASVGDRVTITCSASSRVIYMHWYQQKPGKAPKRWIYDTSKLASGVPS
RFSGSGSGTEFTLTISSLQPEDFATYYCQQWSSNPPTFGGGTKVEIK HuABC77D VL CDR1 amino acid sequences
SEQ ID NO: 63
SASSRVIYMH HuABC77D VL CDR2 amino acid sequences
SEQ ID NO: 64
DTSKLAS HuABC77D VL CDR3 amino acid sequences
SEQ ID NO: 65
QQWSSNPPT Amino acid sequence of the mature heavy chain of HuABC77D encoded in pHuABC77D
SEQ ID NO: 66
EVQLVESGGGLVQPGGSLRLSCAASGFDFSRYWMSWVRQAPGKGLEWIGEINPDSSTINYAPSLKDRFTISRDNAKNS
LYLQMNSLRAEDTAVYYCARHDYDEGIYFDYWGQGTTVTVSSASTKGPSVFPLAPSSKSTSGGTAALGCLVKDYFPEPV
TVSWNSGALTSGVHTFPAVLQSSGLYSLSSVVTVPSSSLGTQTYICNVNHKPSNTKVDKKVEPKSCDKTHTCPPCPAPEA
AGGPSVFLFPPKPKDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK Amino acid sequence of the mature light chain of HuABC77D encoded in pHuABC77D
SEQ ID NO: 67
DIQMTQSPSSLSASVGDRVTITCSASSRVIYMHWYQQKPGKAPKRWIYDTSKLASGVPSRFSGSGSGTEFTLTISSLQPE
DFATYYCQQWSSNPPTFGGGTKVEIKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC Amino acid sequence of the mature HuABC77D VH
SEQ ID NO: 68
EVQLVESGGGLVQPGGSLRLSCAASGFDFSRYWMSWVRQAPGKGLEWIGEINPDSSTINYAPSLKDRFTISRDNAKNS
LYLQMNSLRAEDTAVYYCARHDYDEGIYFDYWGQGTTVTVSS Amino acid sequence of the mature HuABC77D VH fused at the N-terminus to the
extracellular domain of the variant CTLA-4 followed by the linker (CTLA4YE-
HuABC77D VH fusion)
SEQ ID NO: 69
MHVAQPAVVLASSRGIASFVCEYASPGKYTEVRVTVLRQADSQVTEVCAATYMMGNELTFLDDSICTGTSSGNQVNLT
IQGLRAMDTGLYICKVELMYPPPYYEGIGNGTQIYVIDPEPCPDSDSGGGGSGGGGSEVQLVESGGGLVQPGGSLRLSC
AASGFDFSRYWMSWVRQAPGKGLEWIGEINPDSSTINYAPSLKDRFTISRDNAKNSLYLQMNSLRAEDTAVYYCARHD
YDEGIYFDYWGQGTTVTVSS Amino acid sequence of the mature heavy chain of HuABC77D fused at the N-terminus
to the extracellular domain of the variant CTLA-4 followed by the linker encoded
in pHC644
SEQ ID NO: 70
MHVAQPAVVLASSRGIASFVCEYASPGKYTEVRVTVLRQADSQVTEVCAATYMMGNELTFLDDSICTGTSSGNQVNLT
IQGLRAMDTGLYICKVELMYPPPYYEGIGNGTQIYVIDPEPCPDSDSGGGGSGGGGSEVQLVESGGGLVQPGGSLRLSC
AASGFDFSRYWMSWVRQAPGKGLEWIGEINPDSSTINYAPSLKDRFTISRDNAKNSLYLQMNSLRAEDTAVYYCARHD
YDEGIYFDYWGQGTTVTVSSASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTCPPCPAPEAAGGPSVFLFPPKPKDTLMISRTP
EVTCVVVDVSHEDPEVKFNWYVDGVEVHNAKTKPREEQYNSTYRVVSVLTVLHQDWLNGKEYKCKVSNKALPAPIEKT
ISKAKGQPREPQVYTLPPSRDELTKNQVSLTCLVKGFYPSDIAVEWESNGQPENNYKTTPPVLDSDGSFFLYSKLTVDKSR
WQQGNVFSCSVMHEALHNHYTQKSLSLSPGK Amino acid sequence of the mature heavy chain of HuABC77D fused at the C-terminus to the linker followed by the extracellular domain of the variant CTLA-4 encoded in pHC645

SEQ ID NO: 71

EVQLVESGGGLVQPGGSLRLSCAASGFDFSRYWMSWVRQAPGKGLEWIGEINPDSSTINYAPSLKDRFTISRDNAKNS

LYLQMNSLRAEDTAVYYCARHDYDEGIYFDYWGQGTTVTVSSASTKGPSVFPLAPSSKSTSGGTAALGCLVKDYFPEPV

TVSWNSGALTSGVHTFPAVLQSSGLYSLSSVVTVPSSSLGTQTYICNVNHKPSNTKVDKKVEPKSCDKTHTCPPCPAPEA

AGGPSVFLFPPKPKDTLMISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLSLSPGSGGGGSGMHVAQPAVVLASSRGI

ASFVCEYASPGKYTEVRVTVLRQADSQVTEVCAATYMMGNELTFLDDSICTGTSSGNQVNLTIQGLRAMDTGLYICKVE

LMYPPPYYEGIGNGTQIYVIDPEPCPDSD

---

What is claimed is:

1. A bifunctional molecule comprising an antibody that binds to CD122 and inhibits its interaction with IL-2 and IL-15, comprising (a) a mature light chain linked to a CTLA-4 extracellular domain as a chain comprising SEQ ID NO:34 or 42 and a mature heavy chain comprising SEQ ID NO:8 or 33 provided the C-terminal lysine can be omitted, or (b) a mature heavy chain linked to a CTLA-4 extracellular domain as a chain comprising SEQ ID NO:39 provided the C-terminal lysine can be omitted, and a mature light chain comprising SEQ ID NO:9.

2. The bifunctional molecule of claim 1, in the form of a heterodimer comprising two copies of the heavy chain and two copies of the light chain.

3. A bifunctional molecule comprising a mature heavy chain linked to a CTLA-4 extracellular domain as a chain comprising SEQ ID NO:13 or 16 and a mature light chain comprising SEQ ID NO:9.

4. The bifunctional molecule of claim 1, wherein the mature light chain is linked to the CTLA-4 extracellular domain as the chain comprising SEQ ID NO:34 and the mature heavy chain comprises SEQ ID NO:8 or 33 provided the C-terminal lysine can be omitted.

5. The bifunctional molecule of claim 1, wherein the mature heavy chain is linked to the CTLA-4 extracellular domain as the chain comprising SEQ ID NO:39 provided the C-terminal lysine can be omitted, and the mature light chain comprises SEQ ID NO:9.

6. The bifunctional molecule of claim 1, wherein the mature light chain is linked to the CTLA-4 extracellular domain as the chain comprising SEQ ID NO:42, and the mature heavy chain comprises SEQ ID NO:8 or 33 provided the C-terminal lysine can be omitted.

7. A bifunctional molecule comprising a mature heavy chain linked to a CTLA-4 extracellular domain as a chain comprising SEQ ID NO:57 and a mature light chain comprising SEQ ID NO:54.

8. A bifunctional molecule comprising a mature heavy chain linked to a CLTA-4 extracellular domain as a chain comprising SEQ ID NO:56 provided the C-terminal lysine can be omitted, and the mature light chain comprises SEQ ID NO:54.

9. A bifunctional molecule comprising an antibody that binds to CD122 and inhibits its interaction with IL-2 and IL-15, wherein the antibody comprises a heavy chain comprising a mature heavy chain variable region linked to a heavy chain constant region, and a light chain comprising a mature light chain variable region linked to a light chain constant region, wherein the antibody is linked to a CTLA-4 extracellular domain having at least 90% sequence identity with SEQ ID NO:10 and the mature heavy chain variable region comprises three heavy chain CDRs comprising SEQ ID NOS:59-61 respectively and the mature light chain variable region comprises three light chain CDRs comprising SEQ ID NOS:63-65 respectively.

10. The bifunctional molecule of claim 9, wherein the mature heavy chain variable region comprises SEQ ID NO:58 and the mature light chain variable region comprises SEQ ID NO:62.

11. The bifunctional molecule of claim 9, wherein the mature heavy chain comprises SEQ ID NO:66 provided the C-terminal lysine can be omitted, and the mature light chain comprises SEQ ID NO:67.

12. The bifunctional molecule of claim 9, wherein the antibody is linked to the extracellular domain of CTLA-4 via a polypeptide linker.

13. The bifunctional molecule of claim 12, wherein the polypeptide linker comprises the amino acid sequence of SEQ ID NO:11, 36 or 50.

14. A bifunctional molecule comprising a mature heavy chain linked to a CTLA-4 extracellular domain as a chain comprising SEQ ID NO:71 and a mature light chain comprising SEQ ID NO:67.

15. The bifunctional molecule of claim 9, wherein the mature heavy chain is linked to the CTLA-4 extracellular domain as a chain comprising SEQ ID NO:70 provided the C-terminal lysine can be omitted, and the mature light chain comprises SEQ ID NO:67.

16. The bifunctional molecule of claim 9, wherein the antibody has human IgG1 kappa isotype.

17. The bifunctional molecule of claim 9, wherein the heavy chain constant region has one or more mutations to reduce effector function.

18. The bifunctional molecule of claim 17, wherein the mutations are L234A and L235A.

19. The bifunctional molecule of claim 9, wherein the extracellular domain of CTLA-4 comprises SEQ ID NO:10.

20. The bifunctional molecule of claim 9, wherein the extracellular domain of CTLA-4 comprises SEQ ID NO:14.

21. A pharmaceutical composition comprising a bifunctional molecule of claim 1 and a pharmaceutically acceptable carrier.

22. A method of treating a subject having an autoimmune disease, comprising administering an effective regime of the bifunctional molecule of claim 1 to the subject.

23. The method of claim 22, wherein the autoimmune disease is any of vitiligo, alopecia areata, type 1 diabetes, celiac disease, multiple sclerosis, polymyositis, allergic dermatitis, primary biliary cirrhosis, Behcet's disease, and ulcerative colitis.

24. A method of treating a subject having non-alcoholic steatohepatitis, comprising administering an effective regime of the bifunctional molecule of claim 1 to the subject.

25. A method of treating a subject having skin allograft rejection, comprising administering an effective regime of the bifunctional molecule of claim 1 to the subject.

* * * * *